(12) United States Patent
Hashey et al.

(10) Patent No.: US 11,278,613 B2
(45) Date of Patent: Mar. 22, 2022

(54) LYSSAVIRUS ANTIGEN CONSTRUCTS

(71) Applicant: GLAXOSMITHKLINE BIOLOGICALS SA, Rixensart (BE)

(72) Inventors: Kathryn Hashey, Washington, DC (US); Padma Malyala, Cambridge, MA (US); Marcelo Samsa, Rockville, MD (US); Olga Slack, Cambridge, MA (US); Dong Yu, Rockville, MD (US); Alan Stokes, Rockville, MD (US); Rashmi Jalah, Rockville, MD (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/630,951

(22) PCT Filed: Jul. 16, 2018

(86) PCT No.: PCT/IB2018/055258
§ 371 (c)(1),
(2) Date: Jan. 14, 2020

(87) PCT Pub. No.: WO2019/016680
PCT Pub. Date: Jan. 24, 2019

(65) Prior Publication Data
US 2020/0222526 A1 Jul. 16, 2020

Related U.S. Application Data

(60) Provisional application No. 62/533,312, filed on Jul. 17, 2017.

(51) Int. Cl.
*A61K 39/205* (2006.01)
*A61K 9/127* (2006.01)
*A61K 39/00* (2006.01)

(52) U.S. Cl.
CPC ............ *A61K 39/205* (2013.01); *A61K 9/127* (2013.01); *A61K 2039/53* (2013.01)

(58) Field of Classification Search
None
See application file for complete search history.

(56) References Cited

FOREIGN PATENT DOCUMENTS

| WO | 2015024665 A1 | 2/2015 |
| WO | 2018104911 A1 | 6/2018 |
| WO | 2018104919 A1 | 6/2018 |

OTHER PUBLICATIONS

GenBank Accession FJ577895, Rabies virus strain Flury-LEP-C, complete genome, 2010.*
International Search Report and Written Opinion for corresponding International Application No. PCT/IB2018/055258, dated Oct. 8, 2018 (15 pages).
Brito et al., Advances in Genetics, 89:179-233 (2015).
Brito et al., Molecular Therapy, 22: 2118-2129 (2014).
Saxena et al., Vaccine, 26: 6592-6601 (2008).
Saxena et al., Veterinary Microbiology, 136: 36-44 (2009).
Lutz et al., npj Vaccines, 2:29 (2017), doi:10.1038/s41541-017-0032-6. Epub Oct. 19, 2017.
Schnee et al., PLoS Neglected Tropical Diseases, 10:6 (2016) e0004746. https://doi.org/10.1371/journal.ontd.0004746. Epub Jun. 23, 2016.
Rabies vaccines: WHO position paper—Recommendations, Vaccine, 28(44): 7140-7142 (2010) doi: 10.1016/j.vaccine.2010.08. 082. Epub Sep. 8, 2010.

* cited by examiner

*Primary Examiner* — Benjamin P Blumel
(74) *Attorney, Agent, or Firm* — Birch, Stewart, Kolasch & Birch, LLP

(57) ABSTRACT

Nucleic acid based vaccine constructs encoding Lyssaviral antigens are useful in preventing and treating diseases. Self-amplifying RNA molecules encoding Lyssaviral antigens provide potent and long-lasting immunity.

11 Claims, 17 Drawing Sheets

Specification includes a Sequence Listing.

LYSSAVIRUS ANTIGEN CONSTRUCTS

CROSS-REFERENCE TO RELATED APPLICATIONS

This application is filed pursuant to 35 U.S.C. § 371 as a United States National Phase Application of International Patent Application Serial No. PCT/IB2018/055258 filed Jul. 16, 2018, which claims priority to U.S. Provisional Application No. 62/533,312 filed Jul. 17, 2017. The entire contents of each of the foregoing applications are hereby incorporated by reference.

STATEMENT REGARDING FEDERALLY SPONSORED RESEARCH

This invention was made with United States government support under Agreement No. HR0011-12-3-0001 awarded by DARPA. The government has certain rights in the invention.

FIELD OF THE INVENTION

This invention is in the field of treating and preventing viral diseases. In particular, the present invention relates to self-amplifying RNA molecules encoding a *Lyssavirus* antigen. It includes the use of *Lyssavirus* antigens for treating and preventing rabies.

BACKGROUND TO THE INVENTION

*Lyssavirus* is an enveloped, single-stranded RNA virus in the Rhabdoviridae family. Members of the *Lyssavirus* genus cause rabies and have the highest fatality rate of all known human viral pathogens. Rabies is transmitted via the saliva of infected mammals. A neurotropic virus, it enters the nervous system of its host, causing an encephalomyelitis that is almost invariably fatal. Currently there are about 60,000 rabies deaths worldwide yearly, mostly caused by dog bites in developing countries in Asia and Africa and by wildlife and bats in North America.

Rabies presents either in a furious or a paralytic form. The incubation period varies between about five days and several years but is typically between about 20 and 90 days. Clinical illness most often starts with prodromal complaints of malaise, anorexia, fatigue, headache and fever followed by pain or parathesia at the site of exposure. Anxiety, agitation or irritability may be prominent during this period, followed by hyperactivity, disorientation, seizures, hydrophobia, hypersalivation and, eventually, paralysis, coma and death.

Experimentally, RNA vaccines have been derived from sub-genomic replicons that lack viral structural proteins and express a heterologous antigen in place of the viral structural proteins. They can be produced in packaging cell lines that permit the expression of single-round of infectious particles carrying RNAs encoding the vaccine antigen. RNA amplification in the cytoplasm then produces multiple copies of antigen-encoding mRNAs and creates double stranded RNA intermediates, which are known to be potent stimulators of innate immunity. Thus, replicon RNA vaccines can achieve transient high levels of antigen production without the use of a live virus (Brito et al. (2015) Advances in Genetics 89:179-233).

While inserting RNA formulated merely with a buffer, i.e., naked RNA, into a cell can induce both gene expression and an immune response, the in vivo instability of naked RNA limits its potency as a vaccine. Furthermore, the hydrophilicity and strong negative charge of RNA impedes its uptake into cells. However, transfer into the cell cytoplasm can be facilitated. Synthetic delivery systems, such as lipid nanoparticles and cationic nanoemulsions have been demonstrated to effectively transfer nucleic acids, including self-amplifying RNA, into the cell cytoplasm, where it can amplify and express encoded antigens.

There remains a need for novel methods of immunizing against diseases, including diseases caused by Lyssaviruses, which are highly efficacious, safe, convenient, cost-effective, long-lasting and induce a broad spectrum of immune responses. Accordingly, there is a demand for vectors that can effectively deliver vaccine antigens, specifically, *Lyssavirus* antigens. While *Lyssavirus* prophylaxis is currently available, high numbers of doses are required both pre- and post-exposure, and compliance is low, which diminishes the medical benefit. There is a need for an improved *Lyssavirus* vaccine with a simplified administration schedule, increased safety and an enhanced manufacturing profile.

SUMMARY OF THE INVENTION

The present invention provides constructs useful as components of immunogenic compositions for the induction of an immune response in a subject against *Lyssavirus* diseases, methods for their use in treatment, and processes for their manufacture.

A first aspect of the invention provides a nucleic acid-based vaccine construct comprising or consisting of a nucleotide sequence encoding one or more polypeptide comprising or consisting of a full-length *Lyssavirus* protein, or an immunogenic fragment thereof. Alternatively or additionally, the *Lyssavirus* protein is selected from the group consisting of glycoprotein (G), RNA polymerase (L), matrix protein (M), nucleoprotein (N) and phosphoprotein (P).

Alternatively or additionally, the polypeptide comprises a full length *Lyssavirus* glycoprotein or immunogenic fragment thereof. Alternatively or additionally, the *Lyssavirus* glycoprotein is the Flury high egg passage ("HEP") rabies G protein designated AGN9427.1 in GenBank. In another preferred embodiment, the *Lyssavirus* glycoprotein is the Flury low egg passage ("LEP") rabies G protein designated GU565703.1 in GenBank. Alternatively or additionally, the *Lyssavirus* glycoprotein is a codon optimized version of Flury LEP rabies G protein. Alternatively or additionally, the *Lyssavirus* glycoprotein is a codon pair optimized version of Flury LEP rabies G protein.

A second aspect of the invention provides a vector comprising or consisting of the nucleic acid-based vaccine construct.

A third aspect of the invention provides a self-amplifying RNA molecule comprising or consisting of the nucleic acid-based vaccine construct. The self-amplifying RNA molecules of the invention are not encompassed in a virion and the constructs of the invention do not comprise a protein capsid. By avoiding the need to create a capsid, the invention does not require a packaging cell line, thus permitting easier up-scaling for commercial production and minimising the risk that dangerous infectious viruses will inadvertently be produced.

A fourth aspect of the invention provides a DNA molecule encoding the self-amplifying RNA molecule.

A fifth aspect of the invention provides a composition comprising or consisting of one or more of the constructs, vectors, or self-amplifying RNA molecules as described herein. Alternatively or additionally, the composition comprises or consists of an immunologically effective amount of one or more of the constructs, vectors, or self-amplifying RNA molecules.

Alternatively or additionally, the composition comprises or consists of an RNA-based vaccine.

A sixth aspect of the invention provides a method is provided for inducing an immune response against a Lyssaviral disease in a subject in need thereof, which comprises administering to the subject an immunologically effective amount of a composition comprising one or more of the constructs, vectors, or self-amplifying RNA molecules described herein.

A seventh embodiment of the invention provides a process for producing an RNA-based vaccine comprising a step of transcribing the vector or DNA molecule encoding a self-amplifying RNA molecule described herein to produce an RNA comprising a coding region for a *Lyssavirus* antigen.

An eighth aspect of the invention provides a composition produced by the process described herein.

A ninth aspect of the invention provides the use of the construct, vector, self-amplifying RNA molecule, or composition described herein for inducing an immune response against a disease caused by *Lyssavirus* in a subject is provided.

A tenth aspect of the invention provides the construct, vector, self-amplifying RNA molecule, or composition described herein for use in medicine.

An eleventh aspect of the invention provides the construct, vector, self-amplifying RNA molecule, or composition described herein for use in treating or preventing a disease caused by *Lyssavirus* in a subject (e.g., by inducing a protective immune response).

A twelfth aspect of the invention provides the use of the construct, vector, self-amplifying RNA molecule, or composition described herein in the manufacture of a medicament inducing an immune response against a Lyssaviral disease in a subject is provided.

A thirteenth aspect of the invention provides a human dose of the construct, vector, self-amplifying RNA molecule, or composition described herein in the amount of two micrograms or less that is immunogenic in humans.

DESCRIPTION OF THE DRAWINGS

FIG. 1B. Alignment of the DNA sequences of Constructs 1-4 (SEQ ID NOS. 2, 4, 6 and 8, respectively) This figure was originally in color and subsequently revised for black and white, where the specification refers to color related to this figure, the following key applies to this figure: Yellow=plain text; Blue=Italics; Green=underline; White=Bold.

The bottom panel shows the neutralizing anti-rabies antibody titers of four doses of Construct 4 formulated in LNP. 75 ug (triangles); 15 ug (inverted triangles); 3 ug (closed circles); RABAVERT (open circles). The upper dashed line indicates the protective threshold of immunogenicity and the lower dotted line at log 0.1 indicates the lower limits of quantitation (LLOQ).

Figure 7:
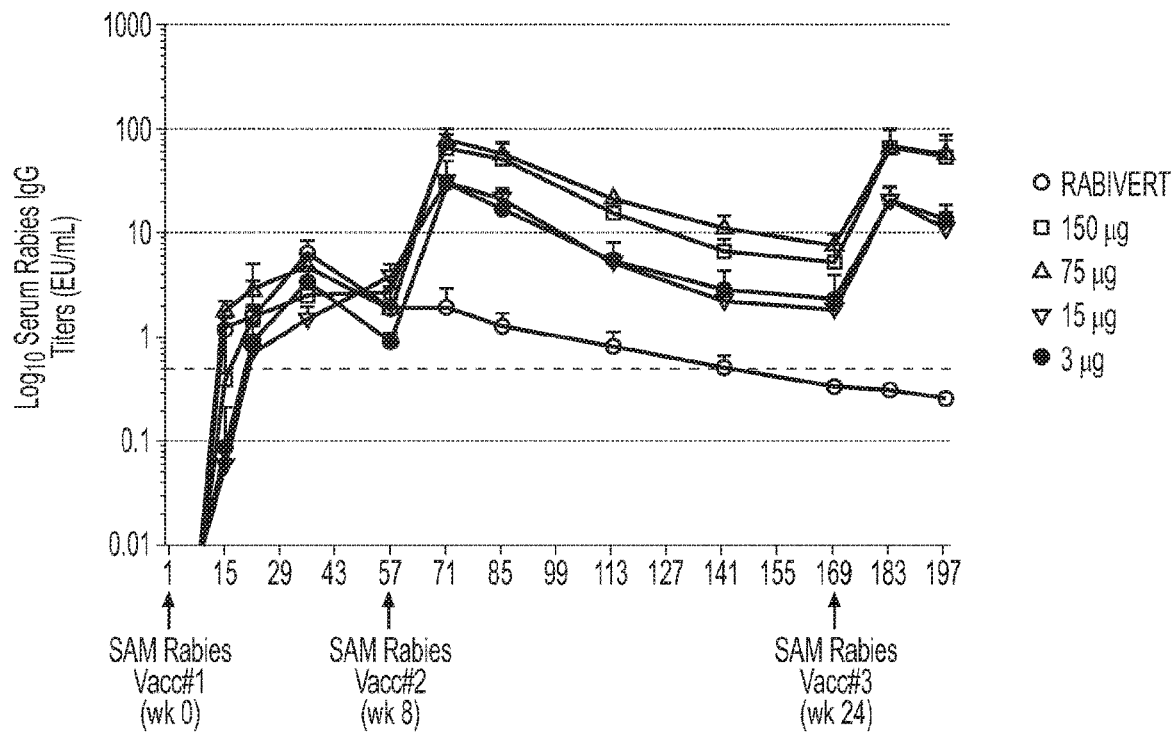
Figure 7:
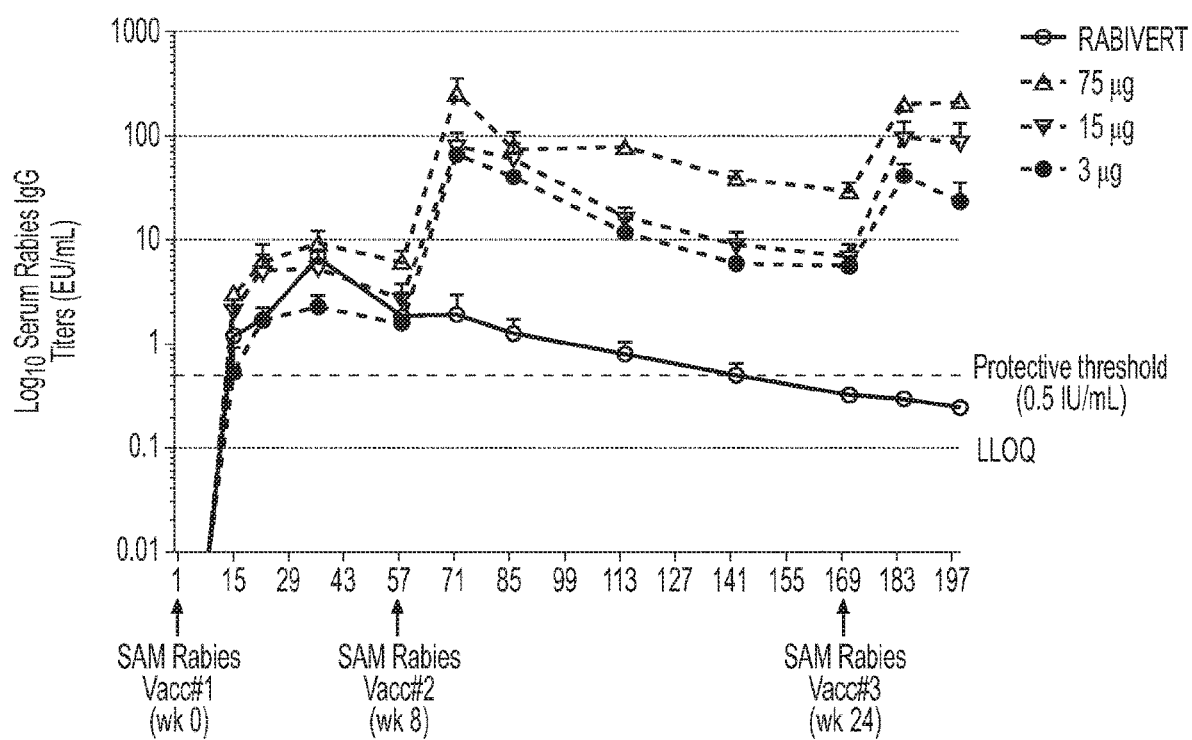

FIG. 7. IgG titers determined by ELISA in non-human primates of Construct 4 immunizations at weeks 0, 8 and 24 compared to a full human dose of RABAVERT immunizations at weeks 0, 1 and 3. The top panel shows the anti-rabies IgG titers of four doses of Construct 4 formulated in CNE. 150 ug (squares); 75 ug (triangles); 15 ug (inverted triangles); 3 ug (closed circles); RABAVERT (open circles). The upper dashed line indicates the protective threshold of immunogenicity and the lower dotted line at log 0.1 indicates the lower limits of quantitation (LLOQ).

The bottom panel shows the anti-rabies IgG titers of four doses of Construct 4 formulated in the RV39 LNP. 75 ug (triangles); 15 ug (inverted triangles); 3 ug (closed circles); RABAVERT (open circles). The upper dashed line indicates the protective threshold of immunogenicity and the lower dotted line at log 0.1 indicates the lower limits of quantitation (LLOQ).

Figure 8:
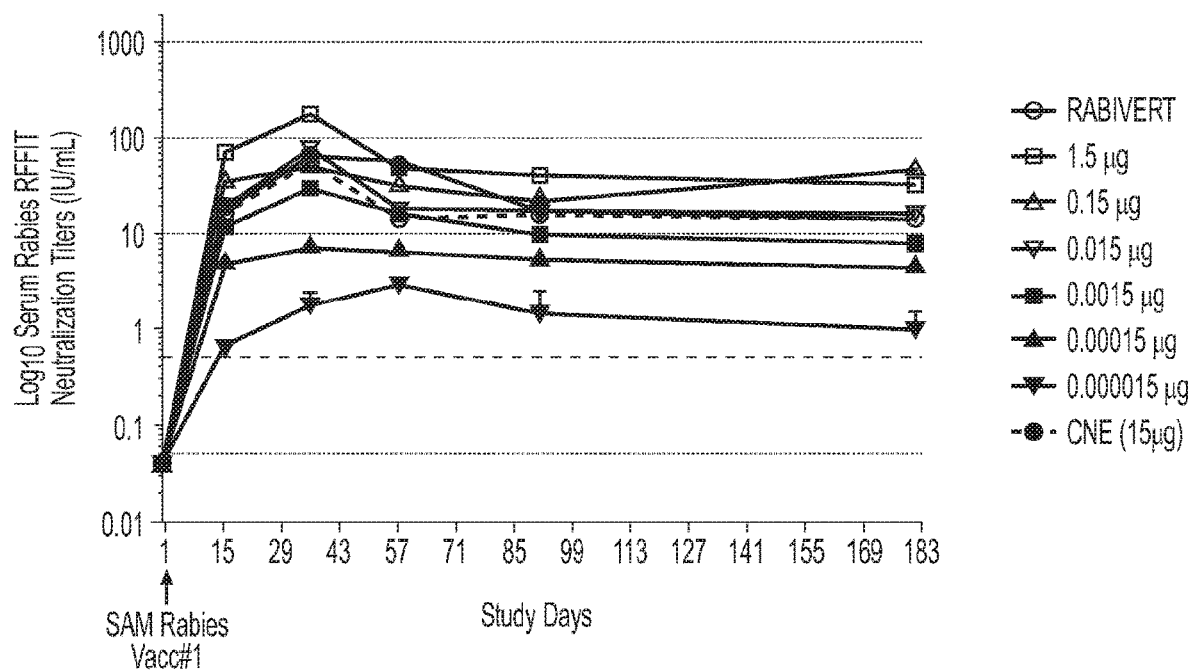
Figure 8:
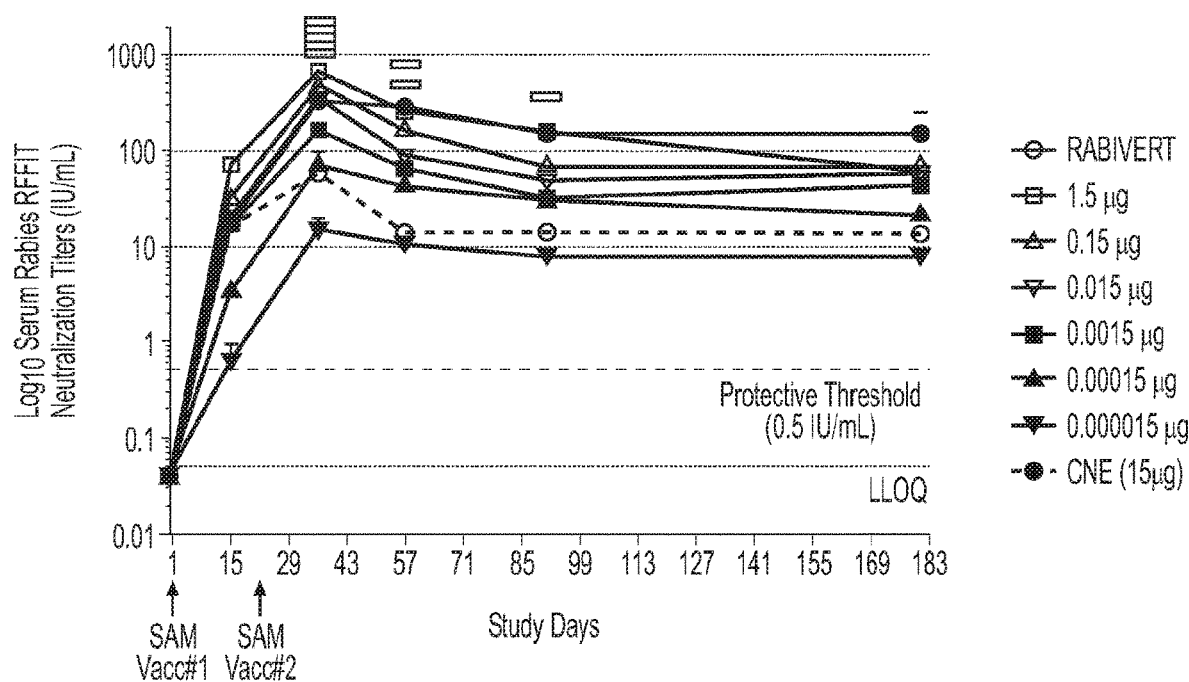

FIG. 8. Dose-response of neutralizing antibody titers determined by RFFIT in mice of Construct 4 in LNP at doses ranging from 15 pg to 1.5 ug or CNE 15 ug. The top panel shows the neutralizing antibody titers for six months following a single dose at day 1. The bottom panel shows the neutralizing antibody titers for six months following two doses at days 1 and 22. RABAVERT (open circles); LNP 1.5 ug (open squares); LNP 0.15 ug (open triangles); LNP 0.015 ug (open inverted triangles); LNP 0.0015 ug (closed squares); LNP 0.00015 ug (closed triangles); LNP 0.000015 ug (closed inverted triangles); CNE 15 ug (closed circles). The upper dashed line indicates the protective threshold of immunogenicity and the lower dotted line below log 0.1 indicates the lower limits of quantitation (LLOQ). The following observations were noted. Similar antibody levels as previous rabies SAM studies were induced with a dose response at lower RNA doses. A single immunization with a dose as low as 15 picograms induced substantial and stable levels of rabies neutralizing antibodies that were maintained over the six months' time tested in mice. The levels were boosted by the second immunization and remained significantly greater than three RABAVERT immunizations.

Figure 9:
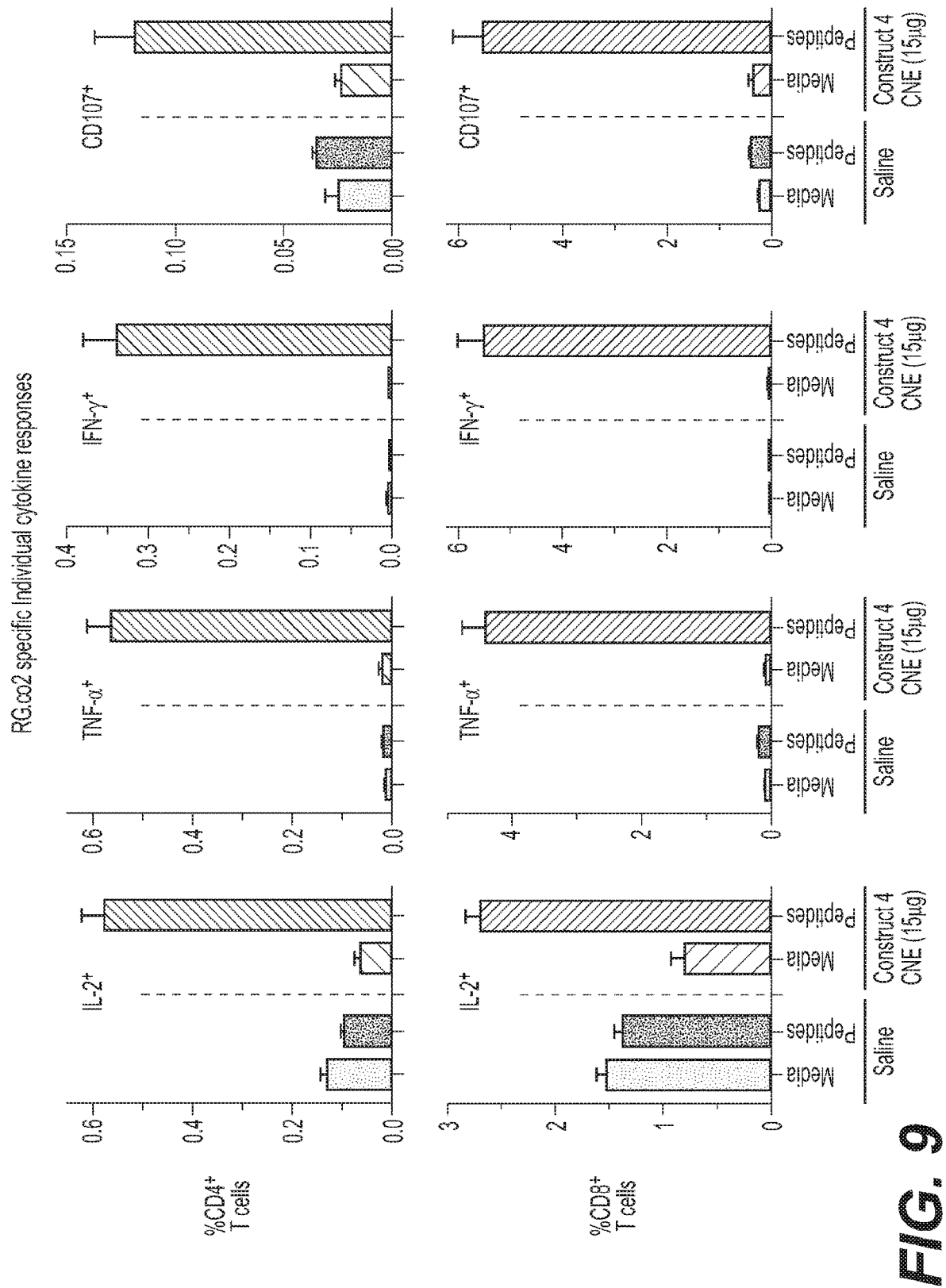

FIG. 9: Specific polyfunctional CD8+ T cell responses in mice by a single 15 ug dose of Construct 4 formulated in CNE. The Th1 cytokines IL-2, TNF alpha, interferon gamma and CD107a were stimulated by rabies antigenic peptides. Their expression in CD4+ and CD8+ T cells are shown in the top and bottom panels respectively. The vaccinated group (8 mice) was compared to a saline control group (5 mice). Cells from each group were exposed to either rabies antigenic peptides or a media control.

Figure 10:
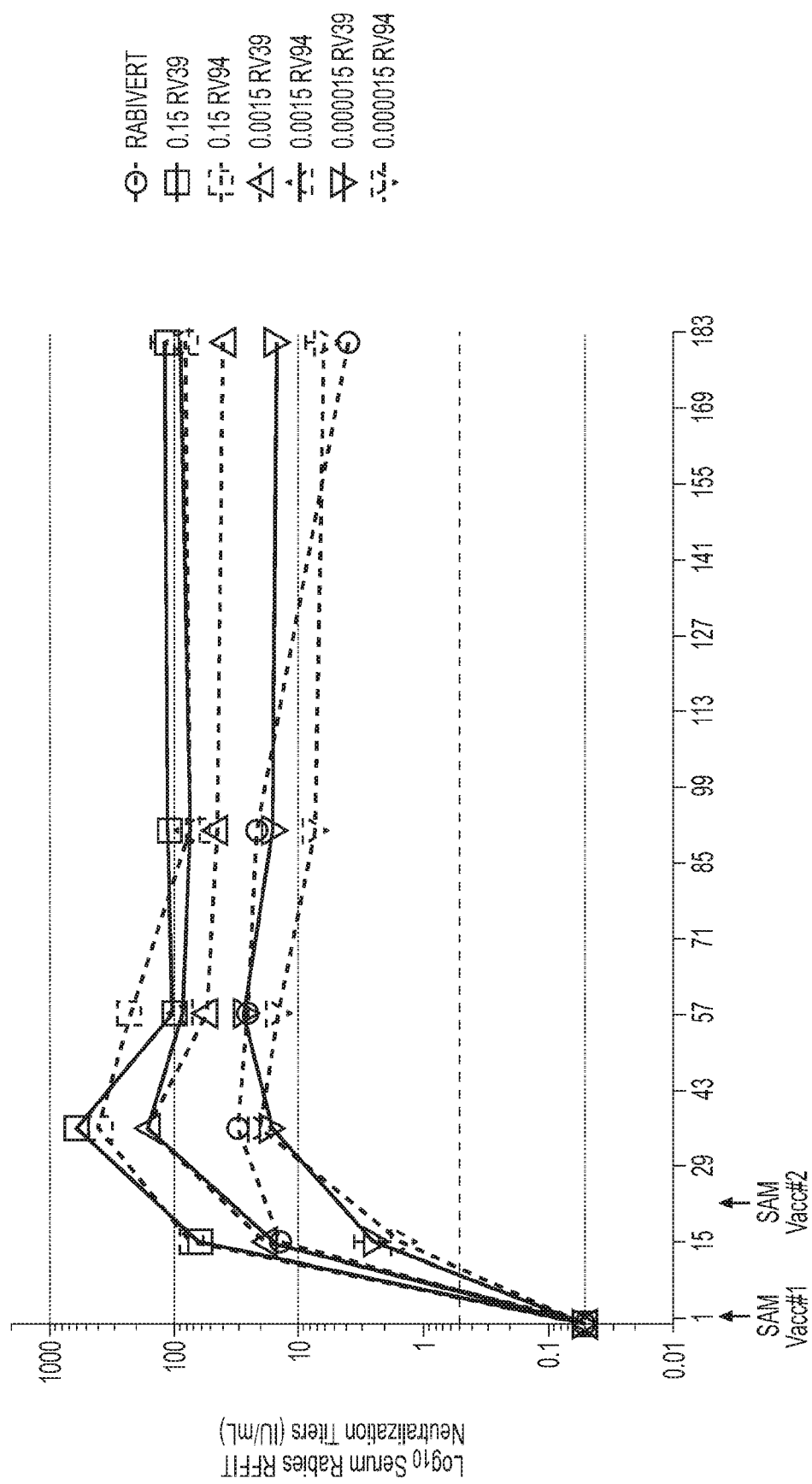

FIG. 10. Dose-response of neutralizing antibody titers determined by RFFIT in mice of Construct 4 at doses ranging from 15 pg to 0.15 ug in the six months following two doses (days 1 and 22). Construct 4 was formulated either with LNP RV39 or LNP RV94. RABAVERT (open circles); 0.15 ug RV39 (open squares); 0.15 ug RV94 (dashed squares); 0.0015 ug RV39 open triangles); 0.0015 ug RV94 (dashed triangles); 0.000015 ug RV39 (open inverted triangles); 0.000015 ug RV94 (dashed inverted triangles). It was observed that both RV39 and RV94 LNP formulations gave similar rabies nAb titers but with greater longevity observed for RV39.

Figure 11:
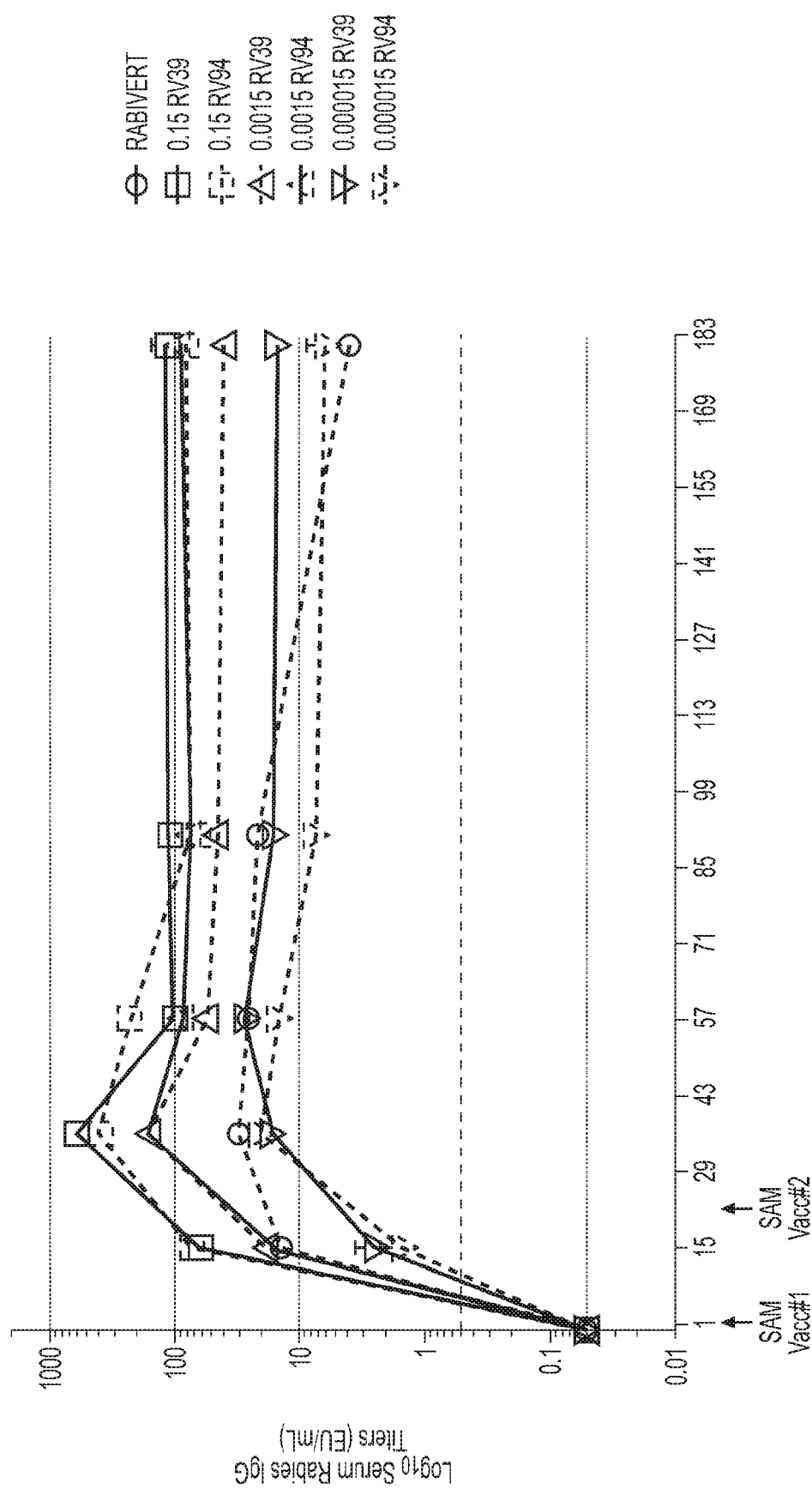

FIG. 11. Dose-response of IgG determined by ELISA in mice of Construct 4 at doses ranging from 15 pg to 0.15 ug for six months following two doses (days 1 and 22). Construct 4 was formulated either with LNP RV39 or LNP RV94. RABAVERT (open circles); 0.15 ug RV39 (open squares); 0.15 ug RV94 (dashed squares); 0.0015 ug RV39 (open triangles); 0.0015 ug RV94 (dashed triangles); 0.000015 ug RV39 (open inverted triangles); 0.000015 ug RV94 (dashed inverted triangles).

DESCRIPTION OF THE SEQUENCES

SEQ ID NO: 1—Vector Backbone—VEE TC83 (empty vector)
SEQ ID NO: 2—Construct 1 Coding Sequence
SEQ ID NO: 3—Construct 1 Amino Acid Sequence
SEQ ID NO: 4—Construct 2 Coding Sequence
SEQ ID NO: 5—Construct 2 Amino Acid Sequence
SEQ ID NO: 6—Construct 3 Coding Sequence
SEQ ID NO: 7—Construct 3 Amino Acid Sequence
SEQ ID NO: 8—Construct 4 Coding Sequence
SEQ ID NO: 9—Construct 4 Amino Acid Sequence

DETAILED DESCRIPTION OF THE INVENTION

Lyssavirus Vaccines

Lyssavirus, a genus in the Rhabdoviridae family, is an enveloped virus with a single-stranded antisense RNA genome. It is a neurotropic virus that spreads through the central nervous system causing severe inflammation of the brain and spinal cord. The RNA encodes five genes, a glycoprotein (G), a viral RNA polymerase (L), a matrix protein (M), a nucleoprotein (N) and a phosphoprotein (P). The G protein is a major target of protective neutralizing antibodies.

The Lyssavirus genus comprises seven genotypes, the following six of which have been associated with cases of human rabies: rabies virus (RABV, genotype 1), Mokola virus (genotype 3), Duvenhage virus (genotype 4), European bat Lyssavirus (genotype 5), European bat Lyssavirus 2 (genotype 6), and Australian bat Lyssavirus (genotype 7). Once symptoms develop, rabies is nearly one hundred percent fatal.

Vaccination is one of the most effective methods for preventing infectious diseases. However, a single administration of an antigen is often not sufficient to confer full immunity and/or a long-lasting response. Rabies currently requires multi-dose vaccination. Approaches to establishing strong and lasting immunity to specific pathogens include addition of adjuvants to vaccines and/or repeated vaccination, i.e. boosting an immune response by administration of one or more further doses of antigen. Such further administrations may be performed with the same vaccine (homologous boosting) or with a different vaccine (heterologous boosting). The most common approach for homologous boosting is not only to administer the same vaccine, but also to administer it in the same dose as the earlier administration.

Rabies vaccines are currently used primarily for post-exposure prophylaxis, only a small percentage of rabies vaccine doses are used for pre-exposure prophylaxis. The intervention schedule is defined by the World Health Organization based on the seriousness and the type of the wound via which the virus gains entry and may include additional treatment with anti-rabies immunoglobulin. Pre-exposure prophylaxis typically involves two to three visits for two to three intramuscular doses with boosters timed according to the exposure risk. Post-exposure prophylaxis typically involves three to five visits for four to five intramuscular doses or four visits for four intradermal doses. In some less-developed countries, immunization is still performed by propagating rabies virus in the brains of an infected animal, inactivating the virus and providing 14-21 daily injections given subcutaneously into the abdominal wall.

Several rabies vaccines are currently available for human use in both pre-exposure and post-exposure prophylaxis and are approved by regulatory agencies when administered in certain dosage regimens. IMOVAX (Sanofi Pasteur) is provided as freeze-dried rabies virus prepared from strain PM-1503-3M obtained from the Wistar Institute. It is harvested from infected human diploid cells then inactivated. Both pre- and post-exposure prophylaxis consists of three doses administered intramuscularly on days 0, 7 and 21 or 28. VERORAB (Sanofi Pasteur) is provided as freeze-dried rabies virus prepared from strain PM/WI 38 1503-3M obtained from the Wistar Institute. It is harvested from Vero cells then inactivated. Pre-exposure prophylaxis consists of three doses administered intramuscularly on days 0, 7 and 21 or 28. Post-exposure prophylaxis consists of five doses administered intramuscularly on days 0, 3, 7, 14 and 28. VAXIRAB/LYSSAVAC (Zydus Cadila/Novavax is provided as freeze-dried rabies virus prepared from the Pitman Moore strain of the rabies virus. It is produced in duck embryo cells then inactivated. Pre-exposure prophylaxis consists of three doses administered intramuscularly on days 0, 7 and 21 or 28. Post-exposure prophylaxis consists of five doses administered intramuscularly on days 0, 3, 7, 14 and 28. Post-exposure prophylaxis can also be administered intradermally, injected at each of two sites on days 0, 3, 7 and 28. RABAVERT (GSK) is provided as a freeze-dried rabies virus prepared from the Flury LEP (low egg passage) strain. It is grown in primary cultures of chicken fibroblasts then inactivated. Pre-exposure prophylaxis consists of three doses administered intramuscularly on days 0, 7 and 21 or 28. Post-exposure prophylaxis consists of five doses administered intramuscularly on days 0, 3, 7, 14 and 28.

The rabies viral strain Flury LEP present in RABAVERT was obtained from the American Type Culture Collection as the 59$^{th}$ egg passage. The growth medium for the propagation of the virus is a synthetic cell culture medium with the addition of human albumin, processed bovine gelatin (polygeline) and antibiotics. The virus is inactivated with beta-propiolactone and further processed by zonal centrifugation in a sucrose density gradient. The vaccine is lyophilized after addition of a stabilizer solution of buffered polygeline and potassium glutamate. The potency of one dose (1.0 ml) RABAVERT is approximately 2.5 IU rabies antigen.

Nucleic acid-based rabies vaccines have been attempted in the past but have proven inferior to RABAVERT. A rabies DNA vaccine encoding the glycoprotein gene and a rabies self-amplifying RNA vaccine encoding the glycoprotein gene were directly compared to RABAVERT. Mice vaccinated with RABAVERT demonstrated a more robust T cell proliferative response, increased cytokine production and higher antibody titers than those vaccinated with either a Sindbis virus RNA replicon expressing rabies G protein or a DNA vaccine expressing rabies G protein. The Sindbis viral replicon vaccine was also inferior to RABAVERT in protecting against a rabies challenge (Saxena et al. (2009) Veterinary Microbiol. 136:36).

Antigens, Variants, Fragments and Constructs

The present invention provides constructs useful as components of immunogenic compositions for the induction of an immune response in a subject against diseases caused by Lyssaviruses. These constructs are useful for the expression of antigens, methods for their use in treatment, and processes for their manufacture. A "construct" is a genetically engineered molecule. A "nucleic acid construct" refers to a genetically engineered nucleic acid and may comprise DNA, RNA, or non-naturally occurring nucleic acid monomers.

In some embodiments, the constructs disclosed herein encode wild-type polypeptide sequences of a *Lyssavirus*, a variant, or a fragment thereof. The constructs may further encode a polypeptide sequence heterologous to the polypeptide sequences of a *Lyssavirus*. In some embodiments, the constructs encode wild-type, variants and/or fragments of polypeptide sequences of a *Lyssavirus* protein of the CVS11, CVS-N2C, Evelyn Rokitniki Abelseth (ERA), Flury, Pitman Moore or Wistar strains. Such antigens may be derived from the rabies viral glycoprotein (G), RNA polymerase (L), matrix protein (M), nucleoprotein (N) and phosphoprotein (P).

A "variant" of a polypeptide sequence includes amino acid sequences having one or more amino acid additions, substitutions and/or deletions when compared to the reference sequence. The variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to SEQ ID NO: 3, SEQ ID NO: 5, SEQ ID NO: 7 or SEQ ID NO: 9. Alternatively, or in addition to, a fragment of a polypeptide may comprise an immunogenic fragment (i.e. an epitope-containing fragment) of the full-length polypeptide which may comprise or consist of a contiguous amino acid sequence of at least 8, at least 9, at least 10, at least 11, at least 12, at least 13, at least 14, at least 15, at least 16, at least 17, at least 18, at least 20, or more amino acids which is identical to a contiguous amino acid sequence of the full-length polypeptide.

Where a *Lyssavirus* G antigen is a variant of a wild-type *Lyssavirus* glycoprotein, the variant may comprise or consist of an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to SEQ ID NO: 3, SEQ ID NO: 5, SEQ ID NO: 7 or SEQ ID NO: 9. Alternatively, or in addition, a fragment of a polypeptide may comprise an immunogenic fragment (i.e. an epitope-containing fragment) of the full-length polypeptide which may comprise or consist of a contiguous amino acid sequence of at least 8, at least 9, at least 10, at least 11, at least 12, at least 13, at least 14, at least 15, at least 16, at least 17, at least 18, at least 20, or more amino acids which is identical to a contiguous amino acid sequence of the full-length polypeptide.

As used herein, the term "antigen" refers to a molecule containing one or more epitopes (e.g., linear, conformational or both) that will stimulate a host's immune system to make a humoral and/or cellular antigen-specific immunological response (i.e. an immune response which specifically recognizes a naturally occurring polypeptide). An "epitope" is that portion of an antigen that determines its immunological specificity.

T- and B-cell epitopes can be identified empirically (e.g. using PEPSCAN or similar methods). They can also be predicted by known methods (e.g. using the Jameson-Wolf antigenic index, matrix-based approaches, TEPITOPE, neural networks, OptiMer & EpiMer, ADEPT, Tsites, hydrophilicity or antigenic index.

Alternatively or additionally, the constructs herein encode a *Lyssavirus* G antigen. By "*Lyssavirus* G antigen" is intended the amino acid sequence, or a nucleotide sequence encoding the amino acid sequence, of a wild-type *Lyssavirus* glycoprotein, variant, or fragment thereof. FIG. 1 identifies the nucleic acid coding sequences of several full-length *Lyssavirus* G protein variants.

Alternatively or additionally, the cross-protective breadth of a vaccine construct can be increased by comprising a medoid sequence of an antigen. By "medoid" is meant a sequence with a minimal dissimilarity to other sequences. Alternatively or additionally, a vector of the invention comprises a medoid sequence of the rabies G glycoprotein or immunogenic fragment thereof. Alternatively or additionally, a self-amplifying RNA construct of the invention comprises a medoid sequence of the rabies G glycoprotein. Alternatively or additionally, the medoid sequence is derived from a natural viral strain with the highest average percent of amino acid identity among all rabies G protein sequences annotated in the NCBI database. Alternatively or additionally, the medoid sequence of the rabies G glycoprotein is NCBI strain AGN94271.

As a result of the redundancy in the genetic code, a polypeptide can be encoded by a variety of different nucleic acid sequences. Coding is biased to use some synonymous codons, i.e., codons that encode the same amino acid, more than others. By "codon optimized" it is intended that modifications in the codon composition of a recombinant nucleic acid are made without altering the amino acid sequence. Codon optimization has been used to improve mRNA expression in different organisms by using organism-specific codon-usage frequencies.

In addition to, and independently from, codon bias, some synonymous codon pairs are used more frequently than others. This codon pair bias means that some codon pairs are overrepresented and others are underrepresented. Codon pair deoptimization has been used to reduce viral virulence. For example, it has been reported that polioviruses modified to contain underrepresented codon pairs demonstrated a decreased translation efficiency and were attenuated compared to wild type poliovirus (WO 2008/121992; Coleman et al. (2008) Science 320:1784). Coleman et al. demonstrated that engineering a synthetic attenuated virus by codon pair deoptimization can produce viruses that encode the same amino acid sequences as wild type but use different pairwise arrangements of synonymous codons. Viruses attenuated by codon pair deoptimization generated up to 1000-fold fewer plaques compared to wild type, produced fewer viral particles and required about 100 times as many viral particles to form a plaque.

In contrast, polioviruses modified to contain codon pairs that are overrepresented in the human genome acted in a manner similar to wild type RNA and generated plaques identical in size to wild type RNA (Coleman et al. (2008) Science 320:1784). This occurred despite the fact that the virus with overrepresented codon pairs contained a similar number of mutations as the virus with underrepresented codon pairs and demonstrated enhanced translation compared to wild type. This observation suggests that codon pair optimized constructs would be expected to act in a manner similar to their non-codon pair optimized counterparts and would not be expected to provide a functional advantage.

Alternatively or additionally, a construct of the invention comprises a codon optimized nucleic acid sequence. Alternatively or additionally, a self-amplifying RNA construct of the invention comprises a codon optimized sequence of the rabies glycoprotein or an immunogenic derivative or fragment thereof. Alternatively or additionally, a self-amplifying RNA construct of the invention comprises a codon optimized sequence of the Flury LEP wild type rabies glycoprotein or an immunogenic derivative or fragment thereof.

Alternatively or additionally, a construct of the invention comprises a codon pair optimized nucleic acid sequence. Alternatively or additionally, a self-amplifying RNA construct of the invention comprises or consists of a codon pair optimized sequence of the rabies glycoprotein or an immunogenic derivative or fragment thereof. Alternatively or additionally, a self-amplifying RNA construct of the invention comprises or consists of a codon pair optimized sequence of the Flury LEP wild type rabies glycoprotein or an immunogenic derivative or fragment thereof.

Alternatively or additionally, the constructs herein encode a *Lyssavirus* L antigen. By "*Lyssavirus* L antigen" is intended the amino acid sequence, or a nucleotide sequence encoding the amino acid sequence, of a known wild-type *Lyssavirus* RNA polymerase, variant, or fragment thereof. Thus, where a *Lyssavirus* L antigen is a variant of a wild-type *Lyssavirus* RNA polymerase, the variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide. Alternatively, or in addition, a fragment of a polypeptide may comprise an immunogenic fragment (i.e. an epitope-containing fragment) of the full-length polypeptide which may comprise a contiguous amino acid sequence of at least 8, at least 9, at least 10, at least 11, at least 12, at least 13, at least 14, at least 15, at least 16, at least 17, at least 18, at least 20, or more amino acids which is identical to a contiguous amino acid sequence of the full-length polypeptide.

Alternatively or additionally, the constructs herein encode a *Lyssavirus* M antigen. By "*Lyssavirus* M antigen" is intended the amino acid sequence, or a nucleotide sequence encoding the amino acid sequence, of a known wild-type *Lyssavirus* matrix protein, variant, or fragment thereof. Thus, where a *Lyssavirus* M antigen is a variant of a wild-type *Lyssavirus* matrix protein, the variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide. Alternatively, or in addition, a fragment of a polypeptide may comprise an immunogenic fragment (i.e. an epitope-containing fragment) of the full-length polypeptide which may comprise a contiguous amino acid sequence of at least 8, at least 9, at least 10, at least 11, at least 12, at least 13, at least 14, at least 15, at least 16, at least 17, at least 18, at least 20, or more amino acids which is identical to a contiguous amino acid sequence of the full-length polypeptide.

Alternatively or additionally, the constructs herein encode a *Lyssavirus* N antigen. By "*Lyssavirus* N antigen" is intended the amino acid sequence, or a nucleotide sequence encoding the amino acid sequence, of a wild-type *Lyssavirus* nucleoprotein, variant, or fragment thereof. Thus, where a *Lyssavirus* N antigen is a variant of a wild-type *Lyssavirus* nucleoprotein, the variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide. Alternatively, or in addition, a fragment of a polypeptide may comprise an immunogenic fragment (i.e. an epitope-containing fragment) of the full-length polypeptide which may comprise a contiguous amino acid sequence of at least 8, at least 9, at least 10, at least 11, at least 12, at least 13, at least 14, at least 15, at least 16, at least 17, at least 18, at least 20, or more amino acids which is identical to a contiguous amino acid sequence of the full-length polypeptide.

Alternatively or additionally, the constructs herein encode a *Lyssavirus* P antigen. By "*Lyssavirus* P antigen" is intended the amino acid sequence, or a nucleotide sequence encoding the amino acid sequence, of a known wild-type *Lyssavirus* phosphoprotein, variant, or fragment thereof. Thus, where a *Lyssavirus* P antigen is a variant of a wild-type *Lyssavirus* phosphoprotein, the variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide.

Alternatively, or in addition, a fragment of a polypeptide may comprise an immunogenic fragment (i.e. an epitope-containing fragment) of the full-length polypeptide which may comprise a contiguous amino acid sequence of at least 8, at least 9, at least 10, at least 11, at least 12, at least 13, at least 14, at least 15, at least 16, at least 17, at least 18, at least 20, or more amino acids which is identical to a contiguous amino acid sequence of the full-length polypeptide.

Alternatively or additionally, a construct encodes more than one component of a polypeptide. The components are juxtaposed immediately next to the adjacent component, i.e., without any intervening amino acids. Alternatively or additionally, a linker group of 1, 2, 3, 4, or 5 amino acids is present between one or more of the polypeptide components.

Alternatively or additionally, the construct comprises an RNA nucleic acid sequence comprising one or more antigens. Multiple antigens can be co-delivered by the constructs of the invention. Constructs of the invention comprise or consist of recombinant polycistronic nucleic acid molecules that contain a first sequence encoding a first *Lyssavirus* antigen and, optionally, a second antigen, which may or may not be a *Lyssavirus* antigen. If desired, one or more additional sequences, encoding additional antigens, for example a third antigen, a fourth antigen, a fifth antigen, etc. can be present in the recombinant RNA. Alternatively or additionally, constructs of the invention can be polycistronic.

Polypeptides

By "polypeptide" is meant a plurality of covalently linked amino acid residues defining a sequence and linked by amide bonds. The term is used interchangeably with peptide. The term peptide also embraces post-translational modifications introduced by chemical or enzyme-catalyzed reactions, as are known in the art. The term can refer to a variant or fragment of a polypeptide.

Alternatively or additionally, a polypeptide herein is in a non-naturally occurring form (e.g. a recombinant or modified form). Polypeptides of the invention may have covalent modifications at the C-terminus and/or N-terminus. They can also take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). The polypeptides can be naturally or non-naturally glycosylated (i.e. the polypeptide may have a glycosylation pattern that differs from the glycosylation pattern found in the corresponding naturally occurring polypeptide).

Non-naturally occurring forms of polypeptides herein may comprise one or more heterologous amino acid sequences (e.g. another antigen sequence, another signal sequence, a detectable tag, or the like) in addition to *Lyssavirus* antigen sequence. For example, a polypeptide herein may be a fusion protein. Alternatively, or in addition, the amino acid sequence or chemical structure of the polypeptide may be modified (e.g. with one or more non-natural amino acids, by covalent modification, and/or or by having a different glycosylation pattern, for example, by the removal or addition of one or more glycosyl groups) compared to a naturally-occurring polypeptide sequence.

Alternatively or additionally, the construct encodes a polypeptide having a sequence selected from the group consisting of SEQ ID NO: 3, SEQ ID NO: 5, SEQ ID NO: 7 and SEQ ID NO: 9. Alternatively or additionally, the construct encodes a polypeptide which is at least 70%, at least 75%, at least 80%, at least 85%, at least 90%, at least 95%, at least 96%, at least 97%, at least 98%, or at least 99% identical to a sequence selected from the group consisting of SEQ ID NO: 3, SEQ ID NO: 5, SEQ ID NO: 7 and SEQ ID NO: 9. Alternatively or additionally, the construct encodes a polypeptide which comprises a fragment of a full-length sequence selected from the group consisting of SEQ ID NO: 3, SEQ ID NO: 5, SEQ ID NO: 7 and SEQ ID NO: 9, wherein the fragment comprises a contiguous stretch of the amino acid sequence of the full-length sequence up to 1, 10, 25, 50, 100, 200, 400, 450 or 475 amino acids shorter than full-length sequence.

Nucleic Acids

The term "nucleic acid" means a polymeric form of nucleotides of any length, which contain deoxyribonucleotides, ribonucleotides, and/or their analogs. It includes DNA, RNA and DNA/RNA hybrids. It also includes DNA or RNA analogs, such as those containing modified backbones (e.g. peptide nucleic acids (PNAs) or phosphorothioates) or modified bases. Thus the nucleic acid of the disclosure includes mRNA, DNA, cDNA, recombinant nucleic acids, branched nucleic acids, plasmids, vectors, etc. Where the nucleic acid takes the form of RNA, it may or may not have a 5' cap.

The present inventors disclose herein nucleic acids comprising one or more nucleic acid sequence which encodes a *Lyssavirus* antigen. A nucleic acid, as disclosed herein, can take various forms (e.g. single-stranded, double-stranded, vector, etc.). Nucleic acids may be circular or branched, but will typically be linear.

The nucleic acids used herein are preferably provided in purified or substantially purified form i.e., substantially free from other nucleic acids (e.g. free from naturally-occurring nucleic acids), particularly from other *Lyssavirus* or host cell nucleic acids, typically being at least about 50% pure (by weight), and usually at least about 90% pure.

Nucleic acids may be prepared in many ways e.g., by chemical synthesis (e.g., phosphoramidite synthesis of DNA) in whole or in part, by digesting longer nucleic acids using nucleases (e.g., restriction enzymes), by joining shorter nucleic acids or nucleotides (e.g., using ligases or polymerases), from genomic or cDNA libraries.

The nucleic acids herein comprise a sequence which encodes at least one *Lyssavirus* antigen. Typically, the nucleic acids of the invention will be in recombinant form, i.e., a form which does not occur in nature. For example, the nucleic acid may comprise one or more heterologous nucleic acid sequences (e.g., a sequence encoding another antigen and/or a control sequence such as a promoter or an internal ribosome entry site) in addition to the sequence encoding the *Lyssavirus* antigen. The nucleic acid may be part of a vector, i.e., part of a nucleic acid construct designed for transduction/transfection of one or more cell types. Vectors may be, for example, expression vectors which are designed to express a nucleotide sequence in a host cell, or viral vectors which are designed to result in the production of a recombinant virus or virus-like particle.

Alternatively, or in addition, the sequence or chemical structure of the nucleic acid may be modified compared to a naturally-occurring sequence which encodes a *Lyssavirus* antigen. The sequence of the nucleic acid molecule may be modified, e.g. to increase the efficacy of expression or replication of the nucleic acid, or to provide additional stability or resistance to degradation. Alternatively or additionally, a vaccine construct of the invention is resistant to RNAse digestion in an in vitro assay.

The nucleic acid encoding the polypeptides described above may be modified to increase translation efficacy and/or half-life. For example, the nucleic acid may be codon optimized or codon-pair optimized. A poly A tail (e.g., of about 30, about 40 or about 50 adenosine residues or more) may be attached to the 3' end of the RNA to increase its half-life. The 5' end of the RNA may be capped with a modified ribonucleotide with the structure m7G (5')ppp (5')N(cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methytransferase, which catalyzes the construction of N7-monomethylated cap 0 structures). Cap 0 structure plays an important role in maintaining the stability and translational efficacy of the RNA molecule. The 5' cap of the RNA molecule may be further modified by a 2'-O-Methyltransferase which results in the generation of a cap 1 structure (m7Gppp [m2'-O] N), which may further increase translation efficacy.

The nucleic acids may comprise one or more nucleotide analogs or modified nucleotides. As used herein, "nucleotide analog" or "modified nucleotide" refers to a nucleotide that contains one or more chemical modifications (e.g., substitutions) in or on the nitrogenous base of the nucleoside (e.g., cytosine (C), thymine (T), uracil (U), adenine (A) or guanine (G)). A nucleotide analog can contain further chemical modifications in or on the sugar moiety of the nucleoside (e.g., ribose, deoxyribose, modified ribose, modified deoxyribose, six-membered sugar analog, or open-chain sugar analog), or in or on the phosphate moiety. Many modified nucleosides and modified nucleotides are commercially available.

Modified nucleobases which can be incorporated into modified nucleosides and nucleotides and be present in the RNA molecules include: m5C (5-methylcytidine); m5U (5-methyluridine); m6A (N6-methyladenosine); s2U (2-thiouridine); Um (2'-O-methyluridine); mlA (1-methyladenosine); m2A (2-methyladenosine); Am (2-1-O-methyl-adenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); mil (1-methylinosine); m'Im (I,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); mIG (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethy 1 aminomethyl-2-L-Omethyl uridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,0-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); £5Cm (5-formyl-2'-O-methylcytidine); mlGm (1,2'-O-dimethylguanosine); m'Am (1,2-O-dimethyl adenosine) irinomethyluridine); tm5s2U (S-taurinomethyl-2-thiouridine)); iniG-14 (4-demethyl guanosine); imG2 (isoguanosine); ac6A (N6-acetyladenosine); hypoxanthine; inosine; 8-oxo-adenine; 7-substituted derivatives thereof, dihydrouracil; pseudouracil; 2-thiouracil; 4-thiouracil; 5-aminouracil; 5-(Ci-Ce)-alkyluracil; 5-methyluracil; 5-(C2—C6)-alkenyluracil; 5-(C2-Ce)-alkynyluracil; 5-(hydroxymethyl)uracil; 5-chlorouracil; 5-fluorouracil; 5-bromouracil; 5-hydroxycytosine; 5-(Ci-C6)-alkylcytosine; 5-methylcytosine; 5-(C2—C6)-alkenylcytosine; 5-(C2—C6)-alkynylcytosine; 5-chlorocytosine; 5-fluorocytosine; 5-bromocytosine; N2-dimethylguanine; 7-deazaguanine; 8-azaguanine; 7-deaza-7-substituted guanine; 7-deaza-7-(C2—C6)alkynylguanine; 7-deaza-8-substituted guanine; 8-hydroxyguanine; 6-thioguanine; 8-oxoguanine; 2-aminopurine; 2-amino-6-chloropurine; 2,4-diaminopurine; 2,6-diaminopurine; 8-azapurine; substituted 7-deazapurine; 7-deaza-7-substituted purine; 7-deaza-8-substituted purine; hydrogen (abasic residue); m5C; m5U; m6A; s2U; W; or 2'-O-methyl-U. Many of these modified nucleobases and their corresponding ribonucleosides are available from commercial suppliers.

Alternatively or additionally, the construct comprises a DNA nucleic acid sequence selected from the group consisting of SEQ ID NO: 2, SEQ ID NO: 4, SEQ ID NO: 6 and SEQ ID NO: 8. Alternatively or additionally, the construct comprises a nucleic acid sequence which is at least 70%, at least 75%, at least 80%, at least 85%, at least 90%, at least 95%, at least 96%, at least 97%, at least 98%, or at least 99% identical to a sequence selected from the group consisting of SEQ ID NO: 2, SEQ ID NO: 4, SEQ ID NO: 6 and SEQ ID NO: 8. Alternatively or additionally, the construct comprises a nucleic acid sequence which comprises a fragment of a full-length sequence selected from the group consisting of SEQ ID NO: 2, SEQ ID NO: 4, SEQ ID NO: 6 and SEQ ID NO: 8, wherein the fragment comprises a contiguous stretch of the nucleic acid sequence of the full-length sequence up to 1, 10, 25, 50, 100, 200, 300, 400, 450 or 475 nucleic acids shorter than the full-length sequence.

Nucleic Acid Based Vaccines

The present invention discloses compositions comprising a nucleic acid sequence which encodes a polypeptide comprising a *Lyssavirus* antigen, variant or fragment thereof. Such compositions may be a nucleic acid-based vaccine. A further composition comprising a nucleic acid sequence which encodes one or more additional *Lyssavirus* antigens may also be provided as a nucleic acid-based vaccine. Alternatively or additionally, a composition comprises a nucleic acid sequence encoding a *Lyssavirus* antigen from a first *Lyssavirus* strain and an additional nucleic acid sequence encoding an additional *Lyssavirus* antigen from one or more other strains of *Lyssavirus*. Alternatively or additionally, a composition comprises a nucleic acid sequence encoding a *Lyssavirus* antigen and an additional

*Lyssavirus* antigen. Alternatively, an additional non-*Lyssavirus* antigen may be encoded.

The nucleic acid may, for example, be RNA (i.e., an RNA-based vaccine) or DNA (i.e., a DNA-based vaccine, such as a plasmid DNA vaccine). Alternatively or additionally, the nucleic acid-based vaccine is an RNA-based vaccine. Alternatively or additionally, the RNA-based vaccine comprises a self-amplifying RNA molecule. The self-amplifying RNA molecule may be an alphavirus-derived RNA replicon.

As used herein, the term "alphavirus" has its conventional meaning in the art and includes various species such as Venezuelan equine encephalitis virus (VEE e.g., Trinidad donkey, TC83CR, etc.), Semliki Forest virus (SFV), Sindbis virus, Ross River virus, Western equine encephalitis virus, Eastern equine encephalitis virus, Chikungunya virus, S.A. AR86 virus, Everglades virus, Mucambo virus, Barmah Forest virus, Middelburg virus, Pixuna virus, O'nyong-nyong virus, Getah virus, Sagiyama virus, Bebaru virus, Mayaro virus, Una virus, Aura virus, Whataroa virus, Banbanki virus, Kyzylagach virus, Highlands J virus, Fort Morgan virus, Ndumu virus, and Buggy Creek virus. The term alphavirus may also include chimeric alphaviruses that contain genome sequences from more than one alphavirus.

An "alphavirus replicon particle" (VRP) or "replicon particle" is an alphavirus replicon packaged with alphavirus structural proteins.

An "alphavirus replicon" (or "replicon") is an RNA molecule which can direct its own amplification in vivo in a target cell. The replicon encodes the polymerase(s) which catalyzes RNA amplification and contains cis RNA sequences required for replication which are recognized and utilized by the encoded polymerase(s). An alphavirus replicon typically contains the following ordered elements: 5' viral sequences required in cis for replication, sequences which encode biologically active alphavirus nonstructural proteins (nsP1, nsP2, nsP3, nsP4), 3' viral sequences required in cis for replication, and a polyadenylate tract. An alphavirus replicon also may contain one or more viral subgenomic "junction region" promoters directing the expression of heterologous nucleotide sequences, which may be modified in order to increase or reduce viral transcription of the subgenomic fragment and heterologous sequence(s) to be expressed.

"Self-amplifying RNA," and "RNA replicon" are used interchangeably to mean RNA with the ability to replicate itself. The self-amplifying RNA molecules of the invention comprise mRNA encoding one or more antigens. This mRNA can replace nucleic acid sequences encoding structural proteins required for the production of infectious virus. The RNA can be produced in vitro by enzymatic transcription, thereby avoiding manufacturing issues associated with cell culture production of vaccines. After immunization with a self-amplifying RNA molecule of the invention, replication and amplification of the RNA molecule occur in the cytoplasm of the transfected cell and the nucleic acid is not integrated into the genome. As the RNA does not integrate into the genome and transform the target cell, self-amplifying RNA vaccines do not pose the safety hurdles faced by recombinant DNA vaccines.

Self-amplifying RNA molecules are known in the art and can be produced by using replication elements derived from, e.g., alphaviruses, and substituting structural viral proteins with a nucleotide sequence encoding a protein of interest. A self-amplifying RNA molecule is typically a plus-strand molecule which can be directly translated after delivery to a cell. This translation provides an RNA-dependent RNA polymerase which then produces both antisense and sense transcripts from the delivered RNA. Thus, the delivered RNA leads to the production of multiple daughter RNAs. These daughter RNAs, as well as collinear subgenomic transcripts, may be translated themselves to provide in situ expression of an encoded antigen (e.g., a *Lyssavirus* antigen), or may be transcribed to provide further transcripts with the same sense as the delivered RNA, which are then translated to provide in situ expression of the antigen. The overall result of this sequence of transcriptions is a huge amplification in the number of the introduced replicon RNAs and so the encoded antigen becomes a major polypeptide product of the cells.

One suitable system for achieving self-replication in this manner is to use an alphavirus-based replicon. These replicons are plus-stranded RNAs which lead to the translation of a replicase (or replicase-transcriptase) following their delivery to a cell. The replicase is translated as a polyprotein which auto-cleaves to provide a replication complex which creates genomic-strand copies of the plus-strand delivered RNA. These minus-strand transcripts can themselves be transcribed to give further copies of the plus-stranded parent RNA and also to give a subgenomic transcript which encodes the antigen. Translation of the subgenomic transcript leads to in situ expression of the antigen by the infected cell. Suitable alphavirus replicons can use a replicase from a Sindbis virus, a Semliki forest virus, an eastern equine encephalitis virus, a Venezuelan equine encephalitis virus, etc. Mutant or wild-type virus sequences can be used e.g. the attenuated TC83 mutant of VEEV has been used in replicons.

Self-amplifying RNAs contain the basic elements of mRNA, i.e., a cap, 5'UTR, 3'UTR and a poly(A) tail. They additionally comprise a large open reading frame (ORF) that encodes non-structural viral genes and one or more subgenomic promoter. The nonstructural genes, which include a polymerase, form intracellular RNA replication factories and transcribe the subgenomic RNA at high levels. This mRNA encoding the vaccine antigen(s) is amplified in the cell, resulting in high levels of mRNA and antigen expression.

Alternatively or additionally, the self-amplifying RNA molecule described herein encodes (i) an RNA-dependent RNA polymerase which can transcribe RNA from the self-amplifying RNA molecule and (ii) a *Lyssavirus* antigen. The polymerase can be an alphavirus replicase e.g., comprising one or more of the non-structural alphavirus proteins nsP1, nsP2, nsP3 and nsP4.

Whereas natural alphavirus genomes encode structural virion proteins in addition to the non-structural replicase polyprotein, alternatively or additionally, the self-amplifying RNA molecules do not encode alphavirus structural proteins. Thus, the self-amplifying RNA can lead to the production of genomic RNA copies of itself in a cell, but not to the production of RNA-containing virions. The inability to produce these virions means that, unlike a wild-type alphavirus, the self-amplifying RNA molecule cannot perpetuate itself in infectious form. The alphavirus structural proteins which are necessary for perpetuation in wild-type viruses are absent from self-amplifying RNAs of the present disclosure and their place is taken by gene(s) encoding the immunogen of interest, such that the subgenomic transcript encodes the immunogen rather than the structural alphavirus virion proteins.

Thus a self-amplifying RNA molecule useful with the invention may have two open reading frames. The first open reading frame encodes a replicase; the second open reading frame encodes an antigen. Alternatively or additionally, the RNA may have one or more additional (e.g. downstream) open reading frames, e.g. to encode further antigen(s) or to encode accessory polypeptides.

Alternatively or additionally, the self-amplifying RNA molecule disclosed herein has a 5' cap (e.g. a 7-methylguanosine). This cap can enhance in vivo translation of the RNA. Alternatively or additionally, the 5' sequence of the self-amplifying RNA molecule must be selected to ensure compatibility with the encoded replicase.

A self-amplifying RNA molecule may have a 3' poly-A tail. It may also include a poly-A polymerase recognition sequence (e.g. AAUAAA) near its 3' end.

Self-amplifying RNA molecules can have various lengths but they are typically 5000-25000 nucleotides long. Self-amplifying RNA molecules will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

The self-amplifying RNA can conveniently be prepared by in vitro transcription (IVT). IVT can use a cDNA template created and propagated in plasmid form in bacteria, or created synthetically, for example by gene synthesis and/or polymerase chain-reaction (PCR) engineering methods. For example, a DNA-dependent RNA polymerase, such as the bacteriophage T7, T3 or SP6 RNA polymerases, can be used to transcribe the self-amplifying RNA from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

The self-amplifying RNA can include, in addition to any 5' cap structure, one or more nucleotides having a modified nucleobase. An RNA used with the invention ideally includes only phosphodiester linkages between nucleosides, but in some embodiments it can contain phosphoramidate, phosphorothioate, and/or methylphosphonate linkages.

The self-amplifying RNA molecule may encode a single heterologous polypeptide antigen (i.e., a *Lyssavirus* antigen) or, optionally, two or more heterologous polypeptide antigens linked together in a way that each of the sequences retains its identity (e.g., linked in series) when expressed as an amino acid sequence. The heterologous polypeptides generated from the self-amplifying RNA may then be produced as a fusion polypeptide or engineered in such a manner as to result in separate polypeptide or peptide sequences.

The self-amplifying RNA molecules described herein may be engineered to express multiple nucleotide sequences, from two or more open reading frames, thereby allowing co-expression of proteins, such as one, two or more *Lyssavirus* antigens (e.g. one, two or *Lyssavirus* antigens) together with cytokines or other immunomodulators, which can enhance the generation of an immune response. Such a self-amplifying RNA molecule might be particularly useful, for example, in the production of various gene products (e.g., proteins) at the same time, for example, as a bivalent or multivalent vaccine.

If desired, the self-amplifying RNA molecules can be screened or analyzed to confirm their therapeutic and prophylactic properties using various in vitro or in vivo testing methods that are known to those of skill in the art. For example, the Rapid Fluorescent Focus Inhibition Test (RFFIT) can measure the level of rabies virus neutralizing activity. Vaccines comprising a self-amplifying RNA molecule can be tested for their effect on the induction of proliferation or on the effector function of a particular lymphocyte type of interest, e.g., B cells, T cells, T cell lines or T cell clones. For example, spleen cells from immunized mice can be isolated and the capacity of cytotoxic T lymphocytes to lyse autologous target cells that contain a self-amplifying RNA molecule encoding a *Lyssavirus* antigen. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

Self-amplifying RNA molecules that encode a *Lyssavirus* antigen can also be tested for ability to induce humoral immune responses, as evidenced, for example, by induction of B cell production of antibodies specific for a *Lyssavirus* antigen of interest. These assays can be conducted using, for example, peripheral B lymphocytes from immunized individuals.

Such assay methods are known to those of skill in the art. Other assays that can be used to characterize the self-amplifying RNA molecules can involve detecting expression of the encoded *Lyssavirus* antigen by the target cells. For example, fluorescent activated cell sorting (FACS) can be used to detect antigen expression on the cell surface or intracellularly. Another advantage of FACS selection is that one can sort for different levels of expression, as sometimes a lower expression may be desired. Other suitable methods for identifying cells which express a particular antigen involve panning using monoclonal antibodies on a plate or capture using magnetic beads coated with monoclonal antibodies.

Alternatively or additionally, a DNA sequence encoding a self-amplifying RNA molecule is provided, and can be selected, from the group consisting of SEQ ID NO: 2, SEQ ID NO: 4, SEQ ID NO: 6 and SEQ ID NO: 8. Alternatively or additionally, DNA sequence encoding a self-amplifying RNA molecule comprises a sequence which is at least 70%, at least 75%, at least 80%, at least 85%, at least 90%, at least 95%, at least 96%, at least 97%, at least 98%, or at least 99% identical to a sequence selected from the group consisting of SEQ ID NO: 2, SEQ ID NO: 4, SEQ ID NO: 6 and SEQ ID NO: 8. Alternatively or additionally, the DNA sequence encoding a self-amplifying RNA molecule comprises or consists of a fragment of a full-length sequence selected from the group consisting of SEQ ID NO: 2, SEQ ID NO: 4, SEQ ID NO: 6 and SEQ ID NO: 8 wherein the fragment comprises or consists of a contiguous stretch of the nucleic acid sequence of the full-length sequence up to 1, 10, 25, 50, 100, 200, 300, 400, 450 or 475 nucleic acids shorter than full-length sequence.

Lipid-Based Delivery Systems

The nucleic acid-based vaccines of the invention may comprise a non-viral delivery system, e.g., a lipid-based delivery system. These systems can efficiently deliver a self-amplifying RNA vaccine to the interior of a cell, where it can then replicate and express the encoded antigen(s).

The delivery system may have adjuvant effects which enhance the immunogenicity of the encoded *Lyssavirus* antigen. For example, the nucleic acid molecule may be encapsulated in liposomes or non-toxic biodegradable polymeric microparticles. Alternatively or additionally, the nucleic acid-based vaccine comprises a lipid nanoparticle (LNP) delivery system. Alternatively or additionally, the nucleic molecule may be delivered as a cationic nanoemulsion (CNE). Alternatively or additionally, the nucleic acid-based vaccine may comprise a naked nucleic acid, such as naked RNA (e.g. mRNA), but lipid-based delivery systems are preferred.

"Lipid nanoparticles (LNPs)" are non-virion liposome particles in which a nucleic acid molecule (e.g. RNA) can be encapsulated. LNP delivery systems and non-toxic biodegradable polymeric microparticles, and methods for their preparation are known in the art. The particles can include some external RNA (e.g. on the surface of the particles), but at least half of the RNA (and preferably all of it) is encapsulated. Liposomal particles can, for example, be formed of a mixture of zwitterionic, cationic and anionic lipids which can be saturated or unsaturated, for example 1,2-distearoyl-sn-glycero-3-phosphocholine (DSPC) (zwitterionic, saturated), 1,2-dilinoleyoxy-3-dimethylaminopropane (DlinDMA) (cationic, unsaturated), and/or 1,2-dimyristoyl-rac-glycerol (DMG) (anionic, saturated). Preferred LNPs for use with the invention include a zwitterionic lipid which can form liposomes, optionally in combination with at least one cationic lipid (such as N-[1-(2,3-Dioleoyloxy)propyl]-N,N,N-trimethylammonium methylsulfate (DOTAPBis(2-methacryloyl)oxyethyl disulfide (DSDMA), 2,3-Dioleyloxy-1-(dimethylamino)propane (DODMA), 1,2-dilinoleyoxy-3-dimethylaminopropane (DLinDMA), N,N-dimethyl-3-aminopropane (DLenDMA), etc.). A mixture of DSPC, DlinDMA, PEG-DMG and cholesterol is particularly effective. Alternatively or additionally, the LNPs are RV01 liposomes.

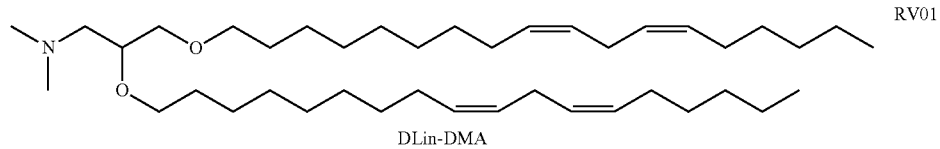 [SMILES: CCCCC/C=C\C/C=C\CCCCCCCCOCC(CN(C)C)OCCCCCCCC/C=C\C/C=C\CCCCC]

RV01

DLin-DMA

Alternatively or additionally, the LNP comprises neutral lipids, cationic lipids, cholesterol and polyethylene glycol (PEG) and forms nanoparticles that encompass the self-amplifying RNA. In some embodiments, the cationic lipids herein comprise the structure of Formula I:

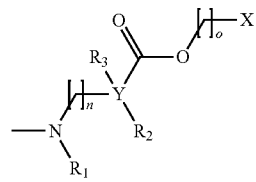

Formula I wherein n=an integer from 1 to 3 and
(i) $R_1$ is $CH_3$, $R_2$ and $R_3$ are both H, and Y is C; or
(ii) $R_1$ and $R_2$ are collectively $CH_2$—$CH_2$ and together with the nitrogen form a five-, six-, or seven-membered heterocycloalkyl, $R_3$ is $CH_3$, and Y is C; or
(iii) $R_1$ is $CH_3$, $R_2$ and $R_3$ are both absent, and Y is O;
wherein o is 0 or 1;

wherein X is:
(i)

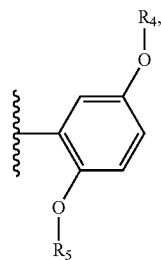

wherein $R_4$ and $R_5$ are independently a $C_{10-20}$ hydrocarbon chain having one or two cis alkene groups at either or both of the omega 6 and 9 positions; or
(ii) —CH(—$R_6$)—$R_7$, wherein
(1) $R_6$ is —$(CH_2)_p$—O—C(O)—$R_8$ or —$C_p$—$R_8$;
(2) $R_7$ is —$(CH_2)_{p'}$—O—C(O)—$R_8'$ or —$C_p$—$R_8'$,
(3) p and p' are independently 0, 1, 2, 3 or 4; and
(4) $R_8$ and $R_{8'}$ are independently a
(A) —$C_{8-20}$ hydrocarbon chain having one or two cis alkene groups at either or both of the omega 6 and 9 positions;
(B) —$C_{1-3}$—C(—O—$C_{6-12}$)—O—$C_{6-12}$ saturated or unsaturated hydrocarbon chain;
(C) —$C_{6-16}$ saturated hydrocarbon chain;
(D) —C(—$C_{6-16}$)—$C_{6-16}$ saturated or unsaturated hydrocarbon chain;
(E) —C[—C—O—C(O)—$C_{4-12}$]—C—O—C(O)—$C_{4-12}$ saturated or unsaturated hydrocarbon chain; and
(F) —$C_{6-16}$ saturated or unsaturated hydrocarbon chain.

In an embodiment, $R_1$ is $CH_3$, $R_2$ and $R_3$ are both H, and Y is C. In some embodiments, $R_1$ and $R_2$ are collectively $CH_2$—$CH_2$ and together with the nitrogen form a five-, six-, or seven-membered heterocycloalkyl, $R_3$ is $CH_3$, and Y is C. In some embodiments, $R_1$ is $CH_3$, $R_2$ and $R_3$ are both absent, and Y is O.

In an embodiment, X is

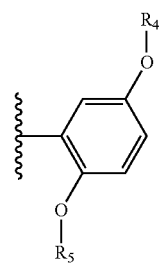

wherein $R_4$ and $R_5$ are independently a $C_{10-20}$ hydrocarbon chain having one or two cis alkene groups at either or both of the omega 6 and 9 positions.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{8-20}$ hydrocarbon chain having one or two cis alkene groups at either or both of the omega 6 and 9 positions; and $R_8'$ is a $-C_{8-20}$ hydrocarbon chain having one or two cis alkene groups at either or both of the omega 6 and 9 positions.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{8-20}$ hydrocarbon chain having one or two cis alkene groups at either or both of the omega 6 and 9 positions; and $R_8'$ is a $-C_{1-3}-C(-O-C_{6-12})-O-C_{6-12}$ saturated or unsaturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{8-20}$ hydrocarbon chain having one or two cis alkene groups at either or both of the omega 6 and 9 positions; and $R_8'$ is a $-C_{6-16}$ saturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{8-20}$ hydrocarbon chain having one or two cis alkene groups at either or both of the omega 6 and 9 positions; and $R_8'$ is a $-C(-C_{6-16})-C_{6-16}$ saturated or unsaturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{8-20}$ hydrocarbon chain having one or two cis alkene groups at either or both of the omega 6 and 9 positions; and $R_8'$ is a $-C[-C-O-C(O)-C_{4-12}]-C-O-C(O)-C_{4-12}$ saturated or unsaturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{8-20}$ hydrocarbon chain having one or two cis alkene groups at either or both of the omega 6 and 9 positions; and $R_8'$ is a $-C_{6-16}$ saturated or unsaturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{1-3}-C(-O-C_{6-12})-O-C_{6-12}$ saturated or unsaturated hydrocarbon chain; and $R_8'$ is a $-C_{8-20}$ hydrocarbon chain having one or two cis alkene groups at either or both of the omega 6 and 9 positions.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{1-3}-C(-O-C_{6-12})-O-C_{6-12}$ saturated or unsaturated hydrocarbon chain; and $R_8'$ is a $-C_{1-3}-C(-O-C_{6-12})-O-C_{6-12}$ saturated or unsaturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{1-3}-C(-O-C_{6-12})-O-C_{6-12}$ saturated or unsaturated hydrocarbon chain; and $R_8'$ is a $-C_{6-16}$ saturated or unsaturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{1-3}-C(-O-C_{6-12})-O-C_{6-12}$ saturated or unsaturated hydrocarbon chain; and $R_8'$ is a $-C[-C-O-C(O)-C_{4-12}]-C-O-C(O)-C_{4-12}$ saturated or unsaturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{1-3}-C(-O-C_{6-12})-O-C_{6-12}$ saturated or unsaturated hydrocarbon chain; and $R_8'$ is a $-C_{6-16}$ saturated or unsaturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{6-16}$ saturated hydrocarbon chain; and $R_8'$ is a $-C_{8-20}$ hydrocarbon chain having one or two cis alkene groups at either or both of the omega 6 and 9 positions.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{6-16}$ saturated hydrocarbon chain; and $R_8'$ is a $-C_{1-3}-C(-O-C_{6-12})-O-C_{6-12}$ saturated or unsaturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{6-16}$ saturated hydrocarbon chain; and $R_8'$ is a $-C_{6-16}$ saturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{6-16}$ saturated hydrocarbon chain; and $R_8'$ is a $-C(-C_{6-16})-C_{6-16}$ saturated or unsaturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{6-16}$ saturated hydrocarbon chain; and $R_8'$ is a $-C[-C-O-C(O)-C_{4-12}]-C-O-C(O)-C_{4-12}$ saturated or unsaturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; $R_8$ is a $-C_{6-16}$ saturated hydrocarbon chain; and $R_8'$ is a $-C_{6-16}$ saturated or unsaturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; and $R_8$ is a $-C(-C_{6-16})-C_{6-16}$ saturated or unsaturated hydrocarbon chain; and $R_8'$ is a $-C_{8-20}$ hydrocarbon chain having one or two cis alkene groups at either or both of the omega 6 and 9 positions.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; and $R_8$ is a $-C(-C_{6-16})-C_{6-16}$ saturated or unsaturated hydrocarbon chain; and $R_8'$ is a $-C_{1-3}-C(-O-C_{6-12})-O-C_{6-12}$ saturated or unsaturated hydrocarbon chain.

In an embodiment, X is $-CH(-R_6)-R_7$, $R_6$ is $-(CH_2)_p-O-C(O)-R_8$, $R_7$ is $-(CH_2)_{p'}-O-C(O)-R_8'$, p and p' are independently 0, 1, 2, 3 or 4; and $R_8$ is a $-C(-C_{6-16})-C_{6-16}$ saturated or unsaturated hydrocarbon chain; and $R_8'$ is a $-C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —$C_{6-16}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —$C_{6-16}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —$C_{6-16}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —$C_{6-16}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —$C_{6-16}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_{p'}$—O—C(O)—$R_8$', p and p' are independently 0, 1, 2, 3 or 4; and $R_8$ is a —$C_{6-16}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{6-16}$ saturated hydrocarbon chain.

In an embodiment, X is —CH(—$R_6$)—$R_7$, $R_6$ is —$(CH_2)_p$—O—C(O)—$R_8$', $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$', $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8'$ is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; $R_8$ is —$C_{1-3}$—C(—O—$C_{6-12}$)—O—$C_{6-12}$ saturated or unsaturated hydrocarbon chain; and $R_8'$ is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8'$ is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8'$ is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8'$ is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8'$ is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; $R_8$ is a —$C_{6-16}$ saturated hydrocarbon chain; and $R_8'$ is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; $R_8$ is a —$C_{6-16}$ saturated hydrocarbon chain; and $R_8'$ is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; $R_8$ is a —$C_{6-16}$ saturated hydrocarbon chain; and $R_8'$ is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; $R_8$ is a —$C_{6-16}$ saturated hydrocarbon chain; and $R_8'$ is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; $R_8$ is a —$C_{6-16}$ saturated hydrocarbon chain; and $R_8'$ is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; $R_8$ is a —$C_{6-16}$ saturated hydrocarbon chain; and $R_8'$ is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C(—$C_{6-16}$)—$C_{6-16}$ saturated or unsaturated hydrocarbon chain; and $R_8'$ is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C(—$C_{6-16}$)—$C_{6-16}$ saturated or unsaturated hydrocarbon chain; and $R_8'$ is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C(—$C_{6-16}$)—$C_{6-16}$ saturated or unsaturated hydrocarbon chain; and $R_8'$ is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C(—$C_{6-16}$)—$C_{6-16}$ saturated or unsaturated hydrocarbon chain; and $R_8'$ is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C(—$C_{6-16}$)—$C_{6-16}$ saturated or unsaturated hydrocarbon chain; and $R_8'$ is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8'$ is a —C(—$C_{6-16}$)—$C_{6-16}$ saturated or unsaturated hydrocarbon chain; and $R_8'$ is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8'$ is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8'$ is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8'$ is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8'$ is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8'$ is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8'$ is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —$C_{6-16}$ saturated or unsaturated hydrocarbon chain; and $R_8'$ is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —$C_{6-16}$ saturated or unsaturated hydrocarbon chain; and $R_8'$ is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —$C_{6-16}$ saturated or unsaturated hydrocarbon chain; and $R_8'$ is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —$C_{6-16}$ saturated or unsaturated hydrocarbon chain; and $R_8'$ is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —$C_{6-16}$ saturated or unsaturated hydrocarbon chain; and $R_8'$ is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —$C_{6-16}$ saturated or unsaturated hydrocarbon chain; and $R_8'$ is a —$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{8-20}$ hydrocarbon chain having one or two cis alkene groups at either or both of the omega 6 and 9 positions; and $R_8'$ is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{8-20}$ hydrocarbon chain having one or two cis alkene groups at either or both of the omega 6 and 9 positions; and $R_8'$ is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{8-20}$ hydrocarbon chain having one or two cis alkene groups at either or both of the omega 6 and 9 positions; and $R_8'$ is a —$C_{6-16}$ saturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{8-20}$ hydrocarbon chain having one or two cis alkene groups at either or both of the omega 6 and 9 positions; and $R_8'$ is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{8-20}$ hydrocarbon chain having one or two cis alkene groups at either or both of the omega 6 and 9 positions; and $R_8'$ is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{8-20}$ hydrocarbon chain having one or two cis alkene groups at either or both of the omega 6 and 9 positions; and $R_8'$ is a —$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8'$ is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8'$ is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8'$ is a —$C_{6-16}$ saturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8'$ is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8'$ is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8'$ is a —$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{6-16}$ saturated hydrocarbon chain; and $R_8'$ is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{6-16}$ saturated hydrocarbon chain; and $R_8'$ is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{6-16}$ saturated hydrocarbon chain; and $R_8'$ is a —$C_{6-16}$ saturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{6-16}$ saturated hydrocarbon chain; and $R_8'$ is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a —$C_{6-16}$ saturated hydrocarbon chain; and $R_8'$ is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8'$, p and p' are independently 0, 1, 2, 3 or 4; $R_8$ is a $—C_{6-16}$ saturated hydrocarbon chain; and $R_8'$ is a $—C_{6-16}$ saturated or unsaturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C(—C_{6-16})—C_{6-16}$ saturated or unsaturated hydrocarbon chain; and $R_8'$ is a $—C_{8-20}$ hydrocarbon chain having one or two cis alkene groups at either or both of the omega 6 and 9 positions.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C(—C_{6-16})—C_{6-16}$ saturated or unsaturated hydrocarbon chain; and $R_8'$ is a $—C_{1-3}—C(—O—C_{6-12})—O—C_{6-12}$ saturated or unsaturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C(—C_{6-16})—C_{6-16}$ saturated or unsaturated hydrocarbon chain; and $R_8'$ is a $—C_{6-16}$ saturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C(—C_{6-16})—C_{6-16}$ saturated or unsaturated hydrocarbon chain; and $R_8'$ is a $—C(—C_{6-16})—C_{6-16}$ saturated or unsaturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C(—C_{6-16})—C_{6-16}$ saturated or unsaturated hydrocarbon chain; and $R_8'$ is a $—C[—C—O—C(O)—C_{4-12}]—C—O—C(O)—C_{4-12}$ saturated or unsaturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C(—C_{6-16})—C_{6-16}$ saturated or unsaturated hydrocarbon chain; and $R_8'$ is a $—C_{6-16}$ saturated or unsaturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8'$ is a $—C[—C—O—C(O)—C_{4-12}]—C—O—C(O)—C_{4-12}$ saturated or unsaturated hydrocarbon chain; and $R_8'$ is a $—C_{8-20}$ hydrocarbon chain having one or two cis alkene groups at either or both of the omega 6 and 9 positions.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C[—C—O—C(O)—C_{4-12}]—C—O—C(O)—C_{4-12}$ saturated or unsaturated hydrocarbon chain; and $R_8'$ is a $—C_{1-3}—C(—O—C_{6-12})—O—C_{6-12}$ saturated or unsaturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C[—C—O—C(O)—C_{4-12}]—C—O—C(O)—C_{4-12}$ saturated or unsaturated hydrocarbon chain; and $R_8'$ is a $—C_{6-16}$ saturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C[—C—O—C(O)—C_{4-12}]—C—O—C(O)—C_{4-12}$ saturated or unsaturated hydrocarbon chain; and $R_8'$ is a $—C(—C_{6-16})—C_{6-16}$ saturated or unsaturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C[—C—O—C(O)—C_{4-12}]—C—O—C(O)—C_{4-12}$ saturated or unsaturated hydrocarbon chain; and $R_8'$ is a $—C_{6-16}$ saturated or unsaturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C_{6-16}$ saturated or unsaturated hydrocarbon chain; and $R_8'$ is a $—C_{8-20}$ hydrocarbon chain having one or two cis alkene groups at either or both of the omega 6 and 9 positions.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C_{6-16}$ saturated or unsaturated hydrocarbon chain; and $R_8'$ is a $—C_{1-3}—C(—O—C_{6-12})—O—C_{6-12}$ saturated or unsaturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C_{6-16}$ saturated or unsaturated hydrocarbon chain; and $R_8'$ is a $—C_{6-16}$ saturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C_{6-16}$ saturated or unsaturated hydrocarbon chain; and $R_8'$ is a $—C(—C_{6-16})—C_{6-16}$ saturated or unsaturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C_{6-16}$ saturated or unsaturated hydrocarbon chain; and $R_8'$ is a $—C[—C—O—C(O)—C_{4-12}]—C—O—C(O)—C_{4-12}$ saturated or unsaturated hydrocarbon chain.

In an embodiment, X is $—CH(—R_6)—R_7$, $R_6$ is $—C_p—R_8$, $R_7$ is $—(CH_2)_{p'}—O—C(O)—R_8'$, p and p' are independently 0, 1, 2, 3 or 4; and $R_8$ is a $—C_{6-16}$ saturated or unsaturated hydrocarbon chain; and $R_8'$ is a $—C_{6-16}$ saturated or unsaturated hydrocarbon chain.

In an embodiment, X is $—CH(—R_6)—R_7$, $R_6$ is $—C_p—R_8$, $R_7$ is $—C_{p'}—R_8'$, p and p' are independently 0, 1, 2, 3 or 4; $R_8$ is a $—C_{8-20}$ hydrocarbon chain having one or two cis alkene groups at either or both of the omega 6 and 9 positions; and $R_8'$ is a $—C_{8-20}$ hydrocarbon chain having one or two cis alkene groups at either or both of the omega 6 and 9 positions.

In an embodiment, X is $—CH(—R_6)—R_7$, $R_6$ is $—C_p—R_8$, $R_7$ is $—C_{p'}—R_8'$, p and p' are independently 0, 1, 2, 3 or 4; $R_8$ is a $—C_{8-20}$ hydrocarbon chain having one or two cis alkene groups at either or both of the omega 6 and 9 positions; and $R_8'$ is a $—C_{1-3}—C(—O—C_{6-12})—O—C_{6-12}$ saturated or unsaturated hydrocarbon chain.

In an embodiment, X is $—CH(—R_6)—R_7$, $R_6$ is $—C_p—R_8$, $R_7$ is $—C_{p'}—R_8'$, p and p' are independently 0, 1, 2, 3 or 4; $R_8$ is a $—C_{8-20}$ hydrocarbon chain having one or two cis alkene groups at either or both of the omega 6 and 9 positions; and $R_8'$ is a $—C_{6-16}$ saturated hydrocarbon chain.

In an embodiment, X is $—CH(—R_6)—R_7$, $R_6$ is $—C_p—R_8$, $R_7$ is $—C_{p'}—R_8'$, p and p' are independently 0, 1, 2, 3 or 4; $R_8$ is a $—C_{8-20}$ hydrocarbon chain having one or two cis alkene groups at either or both of the omega 6 and 9 positions; and $R_8'$ is a $—C(—C_{6-16})—C_{6-16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; $R_8$ is a —$C_{8\text{-}20}$ hydrocarbon chain having one or two cis alkene groups at either or both of the omega 6 and 9 positions; and $R_8'$ is a —C[—C—O—C(O)—$C_{4\text{-}12}$]—C—O—C(O)—$C_{4\text{-}12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; $R_8$ is a —$C_{8\text{-}20}$ hydrocarbon chain having one or two cis alkene groups at either or both of the omega 6 and 9 positions; and $R_8'$ is a —$C_{6\text{-}16}$ saturated or unsaturated hydrocarbon chain.

In an embodiment, X is —CH(—$R_6$)—$R_7$, $R_6$ is —$C_p$—$R_8$, $R_7$—$C_{p'}$—$R_8'$, p and p' are independently 0, 1, 2, 3 or 4; $R_a$ is a —$C_{1\text{-}3}$—C(—O—$C_{6\text{-}12}$)—O—$C_{6\text{-}12}$ saturated or unsaturated hydrocarbon chain; and $R_8'$ is a —$C_{8\text{-}20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; $R_8$ is —$C_{1\text{-}3}$—C(—O—$C_{6\text{-}12}$)—O—$C_{6\text{-}12}$ saturated or unsaturated hydrocarbon chain; and $R_8'$ is a —$C_{1\text{-}3}$—C(—O—$C_{6\text{-}12}$)—O—$C_{6\text{-}12}$ saturated or unsaturated hydrocarbon chain.

In an embodiment, X is —CH(—$R_6$)—$R_7$, $R_6$ is —$C_p$—$R_8$, $R_7$—$C_{p'}$—$R_8'$, p and p' are independently 0, 1, 2, 3 or 4; $R_8$ is a —$C_{1\text{-}3}$—C(—O—$C_{6\text{-}12}$)—O—$C_{6\text{-}12}$ saturated or unsaturated hydrocarbon chain; and $R_8'$ is a —$C_{6\text{-}16}$ saturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; $R_8$ is a —$C_{1\text{-}3}$—C(—O—$C_{6\text{-}12}$)—O—$C_{6\text{-}12}$ saturated or unsaturated hydrocarbon chain; and $R_8'$ is a —C(—$C_{6\text{-}16}$)—$C_{6\text{-}16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; $R_8$ is a —$C_{1\text{-}3}$—C(—O—$C_{6\text{-}12}$)—O—$C_{6\text{-}12}$ saturated or unsaturated hydrocarbon chain; and $R_8'$ is a —C[—C—O—C(O)—$C_{4\text{-}12}$]—C—O—C(O)—$C_{4\text{-}12}$ saturated or unsaturated hydrocarbon chain.

In an embodiment, X is —CH(—$R_6$)—$R_7$, $R_6$ is —$C_p$—$R_8$, $R_7$—$C_{p'}$—$R_8'$, p and p' are independently 0, 1, 2, 3 or 4; $R_8$ is a —$C_{1\text{-}3}$—C(—O—$C_{6\text{-}12}$)—O—$C_{6\text{-}12}$ saturated or unsaturated hydrocarbon chain; and $R_8'$ is a —$C_{6\text{-}16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; $R_8$ is a —$C_{6\text{-}16}$ saturated hydrocarbon chain; and $R_8'$ is a —$C_{8\text{-}20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; $R_8$ is a —$C_{6\text{-}16}$ saturated hydrocarbon chain; and $R_8'$ is a —$C_{1\text{-}3}$—C(—O—$C_{6\text{-}12}$)—O—$C_{6\text{-}12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; $R_8$ is a —$C_{6\text{-}16}$ saturated hydrocarbon chain; and $R_8'$ is a —$C_{6\text{-}16}$ saturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; $R_8$ is a —$C_{6\text{-}16}$ saturated hydrocarbon chain; and $R_8'$ is a —C(—$C_{6\text{-}16}$)—$C_{6\text{-}16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; $R_8$ is a —$C_{6\text{-}16}$ saturated hydrocarbon chain; and $R_8'$ is a —C[—C—O—C(O)—$C_{4\text{-}12}$]—C—O—C(O)—$C_{4\text{-}12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; $R_8$ is a —$C_{6\text{-}16}$ saturated hydrocarbon chain; and $R_8'$ is a —$C_{6\text{-}16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; and $R_8$ is a —C(—$C_{6\text{-}16}$)—$C_{6\text{-}16}$ saturated or unsaturated hydrocarbon chain; and $R_8'$ is a —$C_{8\text{-}20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; and $R_8$ is a —C(—$C_{6\text{-}16}$)—$C_{6\text{-}16}$ saturated or unsaturated hydrocarbon chain; and $R_8'$ is a —$C_{1\text{-}3}$—C(—O—$C_{6\text{-}12}$)—O—$C_{6\text{-}12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; and $R_8$ is a —C(—$C_{6\text{-}16}$)—$C_{6\text{-}16}$ saturated or unsaturated hydrocarbon chain; and $R_8'$ is a —$C_{6\text{-}16}$ saturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; and $R_8$ is a —C(—$C_{6\text{-}16}$)—$C_{6\text{-}16}$ saturated or unsaturated hydrocarbon chain; and $R_8'$ is a —C(—$C_{6\text{-}16}$)—$C_{6\text{-}16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; and $R_8$ is a —C(—$C_{6\text{-}16}$)—$C_{6\text{-}16}$ saturated or unsaturated hydrocarbon chain; and $R_8'$ is a —C[—C—O—C(O)—$C_{4\text{-}12}$]—C—O—C(O)—$C_{4\text{-}12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; and $R_8$ is a —C(—$C_{6\text{-}16}$)—$C_{6\text{-}16}$ saturated or unsaturated hydrocarbon chain; and $R_8'$ is a —$C_{6\text{-}16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; and $R_8$ is a —C[—C—O—C(O)—$C_{4\text{-}12}$]—C—O—C(O)—$C_{4\text{-}12}$ saturated or unsaturated hydrocarbon chain; and $R_8'$ is a —$C_{8\text{-}20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$—$C_{p'}$—$R_8'$, p and p' are independently 0, 1, 2, 3 or 4; and $R_8$ is a —C[—C—O—C(O)—$C_{4\text{-}12}$]—C—O—C(O)—$C_{4\text{-}12}$ saturated or unsaturated hydrocarbon chain; and $R_8'$ is a —$C_{1\text{-}3}$—C(—O—$C_{6\text{-}12}$)—O—$C_{6\text{-}12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; and $R_8$ is a —C[—C—O—C(O)—$C_{4\text{-}12}$]—C—O—C(O)—$C_{4\text{-}12}$ saturated or unsaturated hydrocarbon chain; and $R_8'$ is a —$C_{6\text{-}16}$ saturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; and $R_8$ is a —C[—C—O—C(O)—$C_{4\text{-}12}$]—C—O—C(O)—$C_{4\text{-}12}$ saturated or unsaturated hydrocarbon chain; and $R_8'$ is a —C(—$C_{6\text{-}16}$)—$C_{6\text{-}16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8'$, p and p' are independently 0, 1, 2, 3 or 4; and $R_8$ is a —C[—C—O—C(O)—$C_{4\text{-}12}$]—C—O—C(O)—$C_{4\text{-}12}$ saturated or unsaturated hydrocarbon chain; and $R_8'$ is a —C[—C—O—C(O)—C$_{4-12}$]—C—O—C(O)—C$_{4-12}$ saturated or unsaturated hydrocarbon chain.

In an embodiment, X is —CH(—R$_6$)—R$_7$, R$_6$ is —C$_p$—R$_8$, R$_7$—C$_{p'}$—R$_8'$, p and p' are independently 0, 1, 2, 3 or 4; and R$_8$ is a —C[—C—O—C(O)—C$_{4-12}$]—C—O—C(O)—C$_{4-12}$ saturated or unsaturated hydrocarbon chain; and R$_8'$ is a —C$_{6-16}$ saturated or unsaturated hydrocarbon chain.

In an embodiment, X is —CH(—R$_6$)—R$_7$, R$_6$ is —C$_p$—R$_8$, R$_7$ is —C$_{p'}$—R$_8'$, p and p' are independently 0, 1, 2, 3 or 4; and R$_8$ is a —C$_{6-16}$ saturated or unsaturated hydrocarbon chain; and R$_8'$ is a —C$_{8-20}$ hydrocarbon chain having one or two cis alkene groups at either or both of the omega 6 and 9 positions.

In an embodiment, X is —CH(—R$_6$)—R$_7$, R$_6$ is —C$_p$—R$_8$, R$_7$ is —C$_{p'}$—R$_8'$, p and p' are independently 0, 1, 2, 3 or 4; and R$_8$ is a —C$_{6-16}$ saturated or unsaturated hydrocarbon chain; and R$_8'$ is a —C$_{1-3}$—C(—O—C$_{6-12}$)—O—C$_{6-12}$ saturated or unsaturated hydrocarbon chain.

In an embodiment, X is —CH(—R$_6$)—R$_7$, R$_6$ is —C$_p$—R$_8$, R$_7$—C$_{p'}$—R$_8'$, p and p' are independently 0, 1, 2, 3 or 4; and R$_8$ is a —C$_{6-16}$ saturated or unsaturated hydrocarbon chain; and R$_8'$ is a —C$_{6-16}$ saturated hydrocarbon chain.

In an embodiment, X is —CH(—R$_6$)—R$_7$, R$_6$ is —C$_p$—R$_8$, R$_7$ is —C$_{p'}$—R$_8'$, p and p' are independently 0, 1, 2, 3 or 4; and R$_8$ is a —C$_{6-16}$ saturated or unsaturated hydrocarbon chain; and R$_8'$ is a —C(—C$_{6-16}$)—C$_{6-16}$ saturated or unsaturated hydrocarbon chain.

In an embodiment, X is —CH(—R$_6$)—R$_7$, R$_6$ is —C$_p$—R$_8$, R$_7$ is —C$_{p'}$—R$_8'$, p and p' are independently 0, 1, 2, 3 or 4; and R$_8$ is a —C$_{6-16}$ saturated or unsaturated hydrocarbon chain; and R$_8'$ is a —C[—C—O—C(O)—C$_{4-12}$]—C—O—C(O)—C$_{4-12}$ saturated or unsaturated hydrocarbon chain.

In an embodiment, X is —CH(—R$_6$)—R$_7$, R$_6$ is —C$_p$—R$_8$, R$_7$ is —C$_{p'}$—R$_8'$, p and p' are independently 0, 1, 2, 3 or 4; and R$_8$ is a —C$_{6-16}$ saturated or unsaturated hydrocarbon chain; and R$_8'$ is a —C$_{6-16}$ saturated or unsaturated hydrocarbon chain.

In an embodiment, an exemplary cationic lipid is RV28 having the following structure:

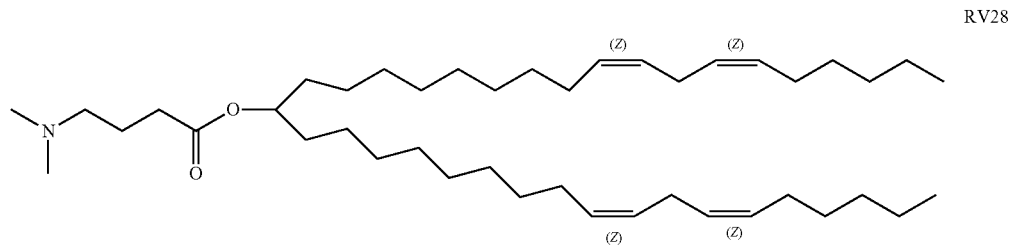 [SMILES: CCCCC/C=C\C/C=C\CCCCCCCCC(CCCCCCCC/C=C\C/C=C\CCCCC)OC(=O)CCCN(C)C]

RV28

In an embodiment, an exemplary cationic lipid is RV31 having the following structure:

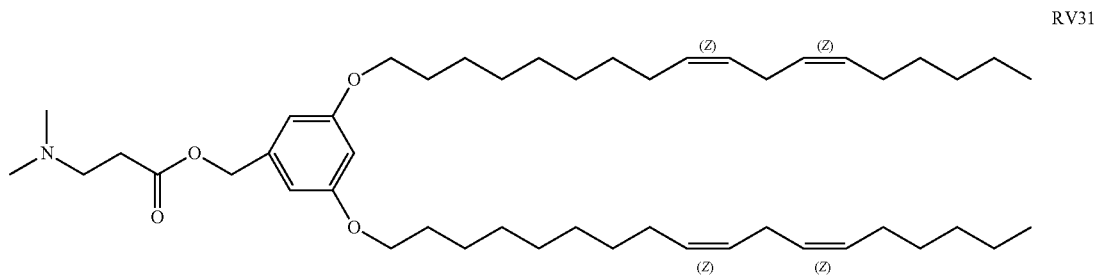 [SMILES: CCCCC/C=C\C/C=C\CCCCCCCCOc1cc(COC(=O)CCN(C)C)cc(OCCCCCCCC/C=C\C/C=C\CCCCC)c1]

RV31

In an embodiment, an exemplary cationic lipid is RV33 having the following structure:

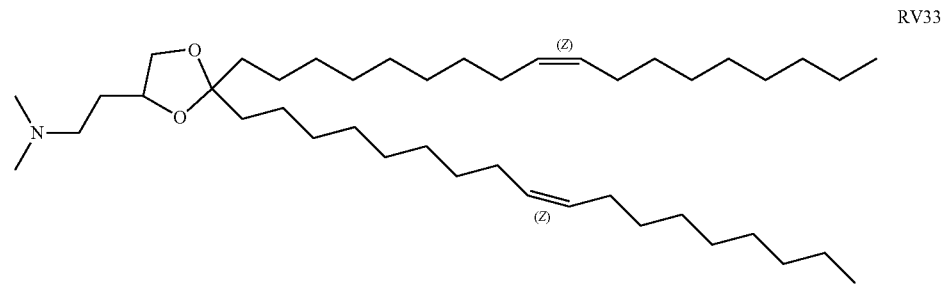 [SMILES: CCCCCCCC/C=C\CCCCCCCCC1(CCCCCCCC/C=C\CCCCCCCC)OCC(CCN(C)C)O1]

RV33

In an embodiment, an exemplary cationic lipid is RV37 having the following structure:

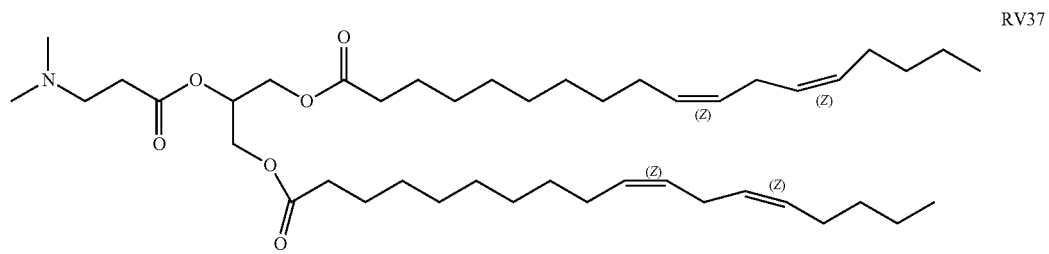 [SMILES: CCCC/C=C\C/C=C\CCCCCCCCC(=O)OCC(COC(=O)CCCCCCCC/C=C\C/C=C\CCCC)OC(=O)CCN(C)C]

In an embodiment, the LNP comprises the cationic lipid RV39, i.e., 2,5-bis((9Z,12Z)-octadeca-9,12-dien-1-yloxy) benzyl 4-(dimethylamino)butanoate):

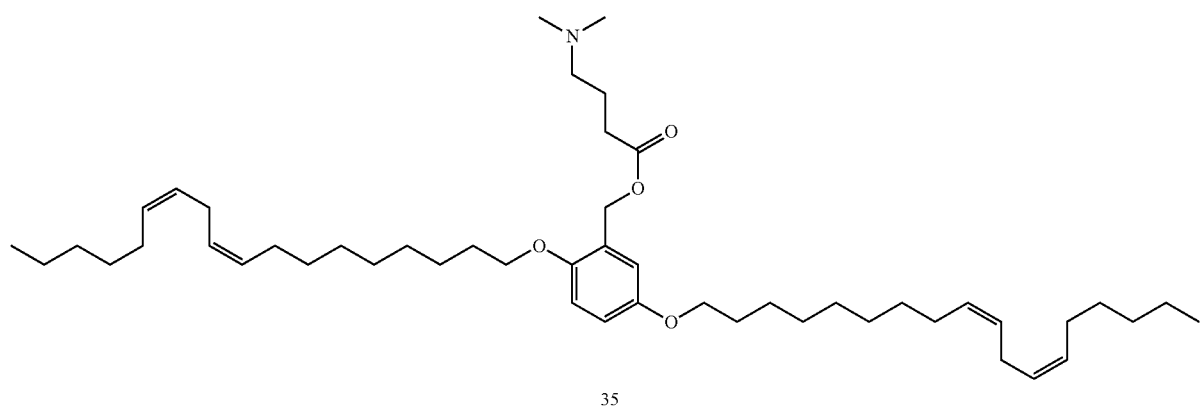

In an embodiment, an exemplary cationic lipid is RV42 having the following structure:

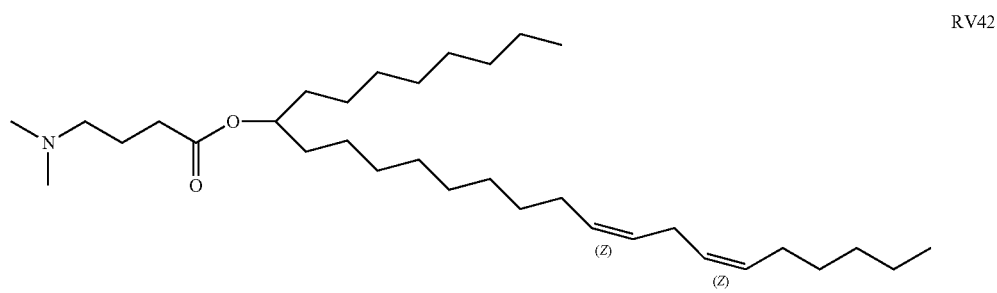 [SMILES: CCCCC/C=C\C/C=C\CCCCCCCCC(CCCCCCCC)OC(=O)CCCN(C)C]

In an embodiment, an exemplary cationic lipid is RV44 having the following structure:

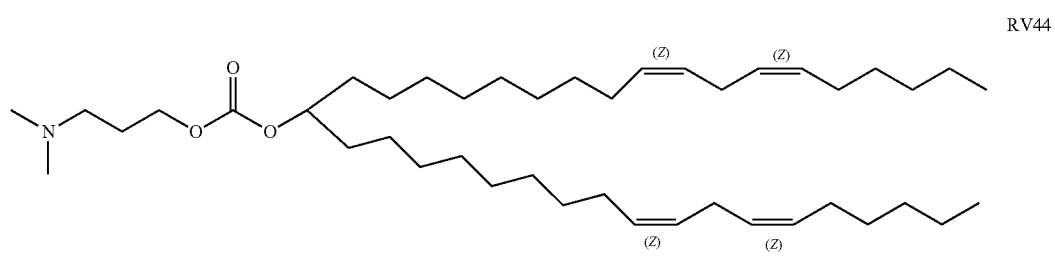 [SMILES: CCCCC/C=C\C/C=C\CCCCCCCCC(CCCCCCCC/C=C\C/C=C\CCCCC)OC(=O)OCCCN(C)C]

In an embodiment, an exemplary cationic lipid is RV73 having the following structure:
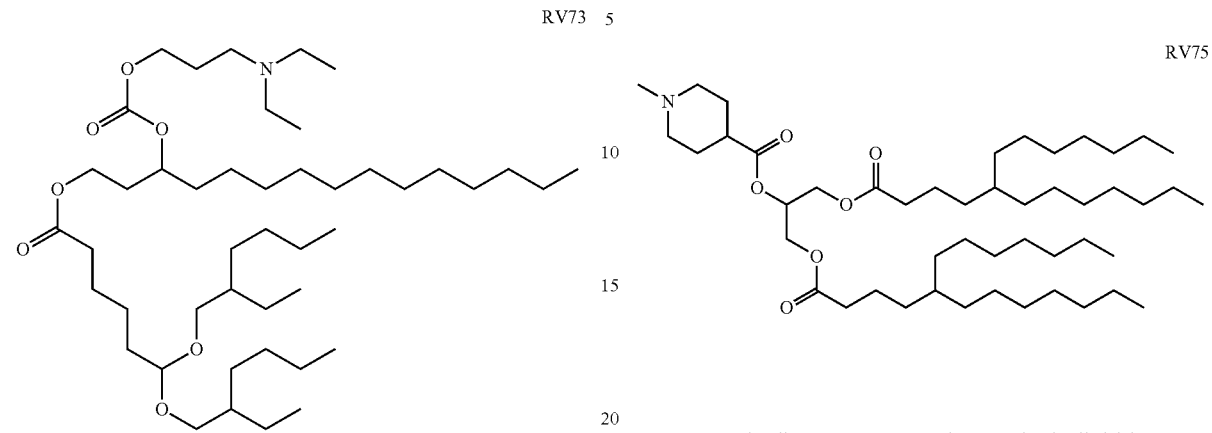
In an embodiment, an exemplary cationic lipid is RV75 having the following structure:
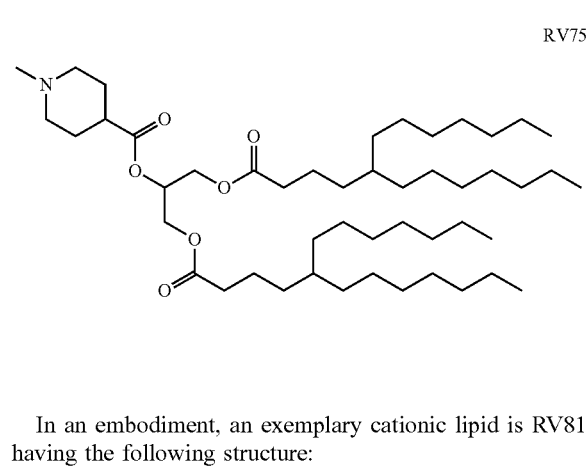
In an embodiment, an exemplary cationic lipid is RV81 having the following structure:
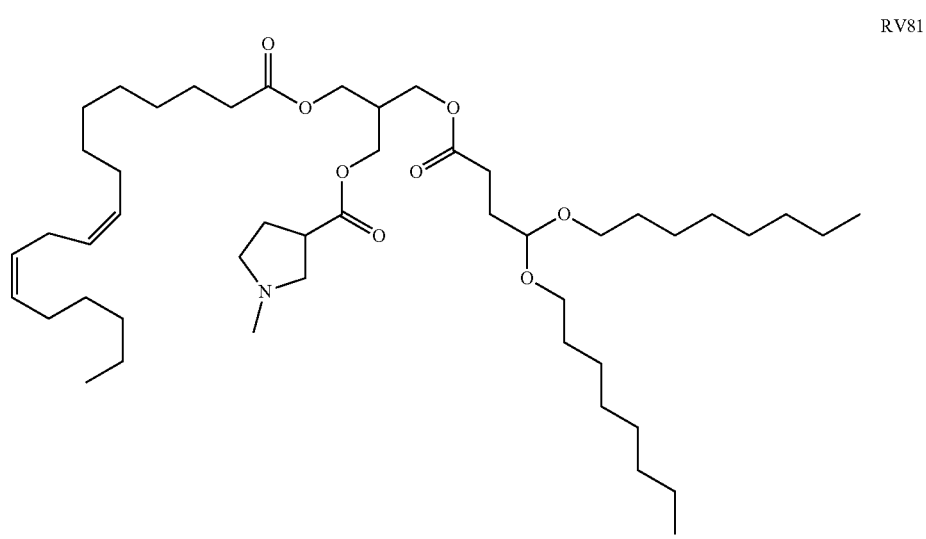 [SMILES: CCCCC/C=C\C/C=C\CCCCCCCC(=O)OCC(COC(=O)CCC(OCCCCCCCC)OCCCCCCCC)COC(=O)C1CCN(C)C1]
In an embodiment, an exemplary cationic lipid is RV84 having the following structure:
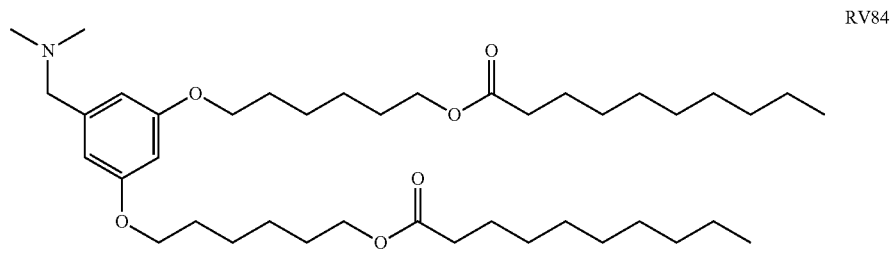 [SMILES: CCCCCCCCCC(=O)OCCCCCCOc1cc(CN(C)C)cc(OCCCCCCOC(=O)CCCCCCCCC)c1]

In an embodiment, an exemplary cationic lipid is RV85 having the following structure:
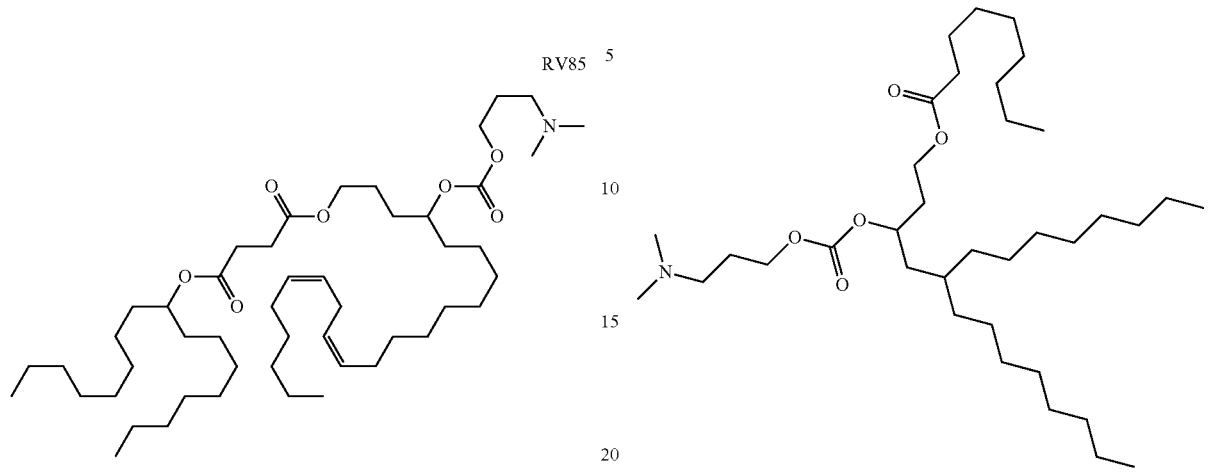
In an embodiment, an exemplary cationic lipid is RV86 having the following structure:
In an embodiment, an exemplary cationic lipid is RV88 having the following structure:
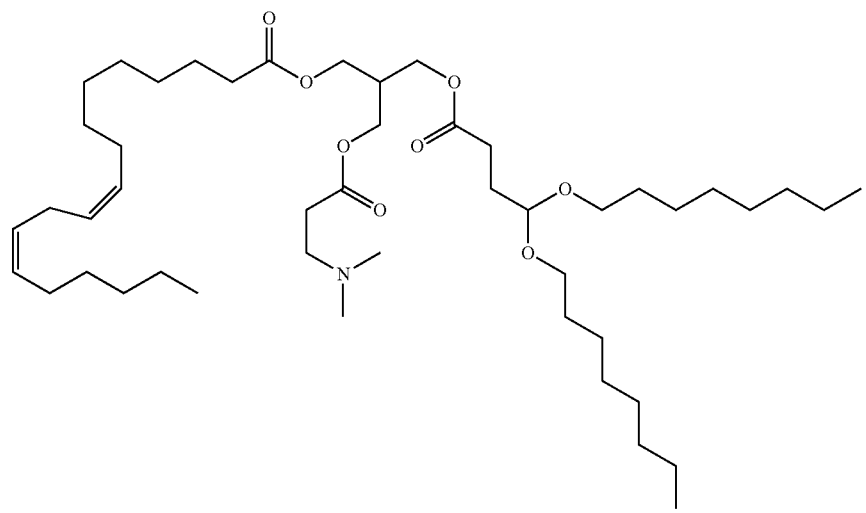
In an embodiment, an exemplary cationic lipid is RV91 having the following structure:
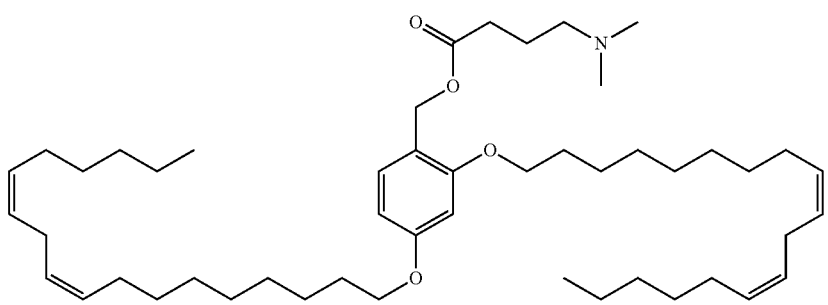

In an embodiment, an exemplary cationic lipid is RV92 having the following structure:

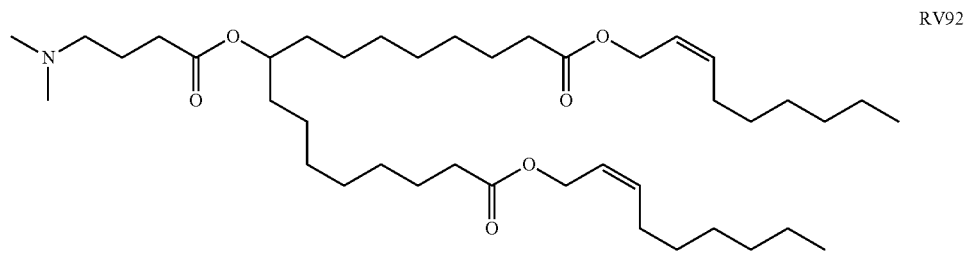 [SMILES: CCCCCC/C=C\COC(=O)CCCCCCCC(CCCCCCCC(=O)OC/C=C\CCCCCC)OC(=O)CCCN(C)C]

In an embodiment, an exemplary cationic lipid is RV93 having the following structure:

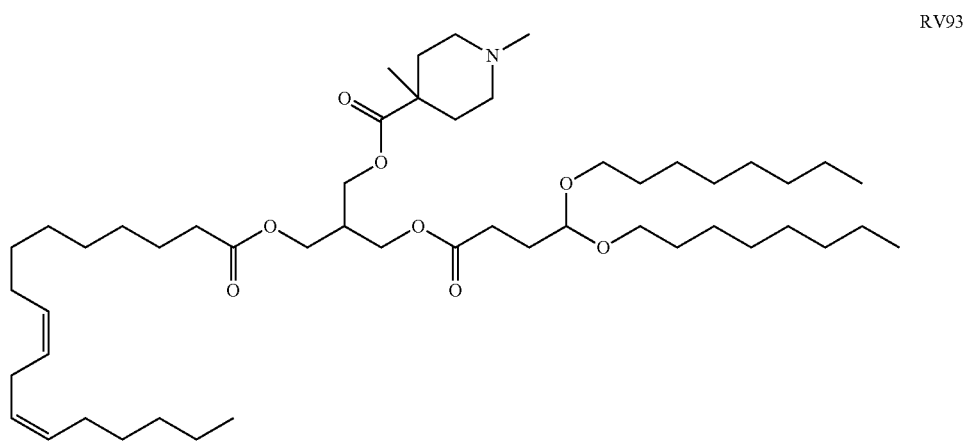 [SMILES: CCCCC/C=C\C/C=C\CCCCCCCC(=O)OCC(COC(=O)CCC(OCCCCCCCC)OCCCCCCCC)COC(=O)C1(C)CCN(C)CC1]

In an embodiment, an exemplary cationic lipid is 2-(5-((4-((1,4-dimethylpiperidine-4-carbonyl)oxy)hexadecyl)oxy)-5-oxopentyl)propane-1,3-diyl dioctanoate (RV94), having the following structure:

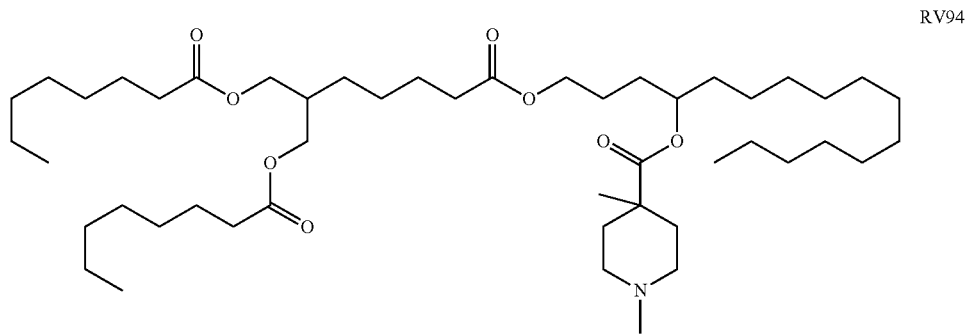 [SMILES: CCCCCCCCCCCCC(CCCOC(=O)CCCCC(COC(=O)CCCCCCC)COC(=O)CCCCCCC)OC(=O)C1(C)CCN(C)CC1]

In an embodiment, an exemplary cationic lipid is RV95 having the following structure:

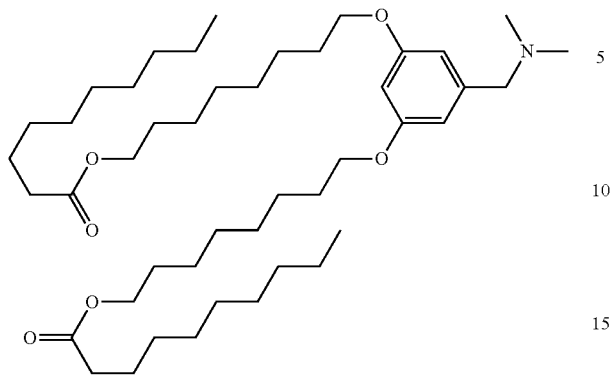
RV95
In an embodiment, an exemplary cationic lipid is RV96 having the following structure:
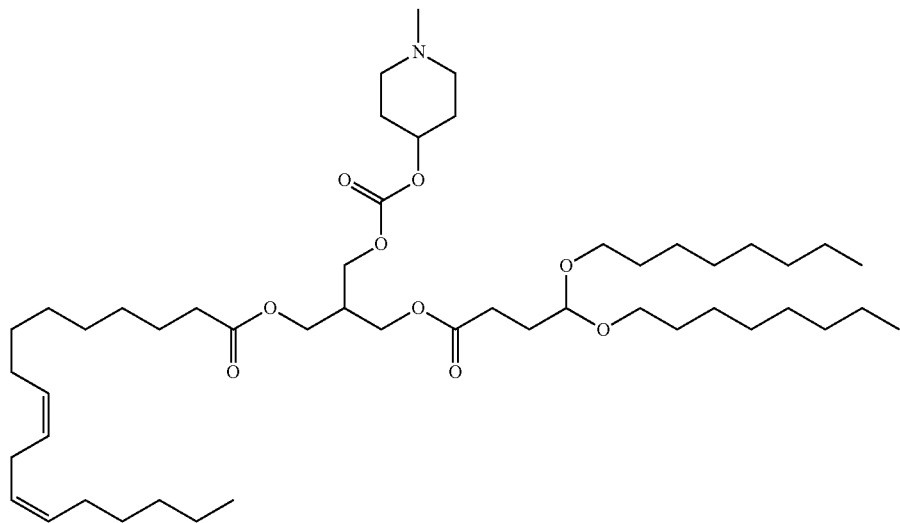
RV96
In an embodiment, an exemplary cationic lipid is RV97 having the following structure:
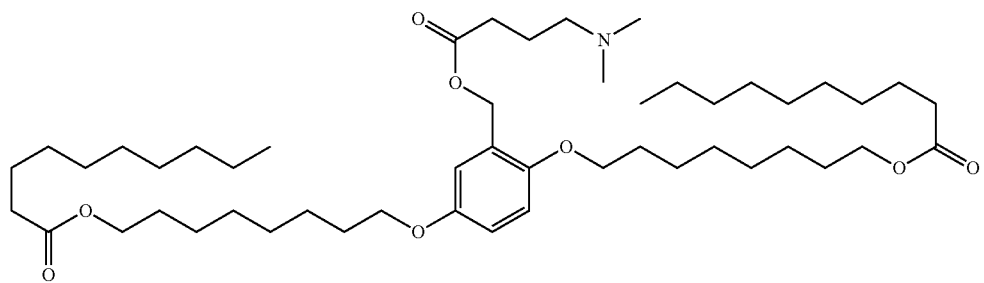
RV97
In an embodiment, an exemplary cationic lipid is RV99 having the following structure:

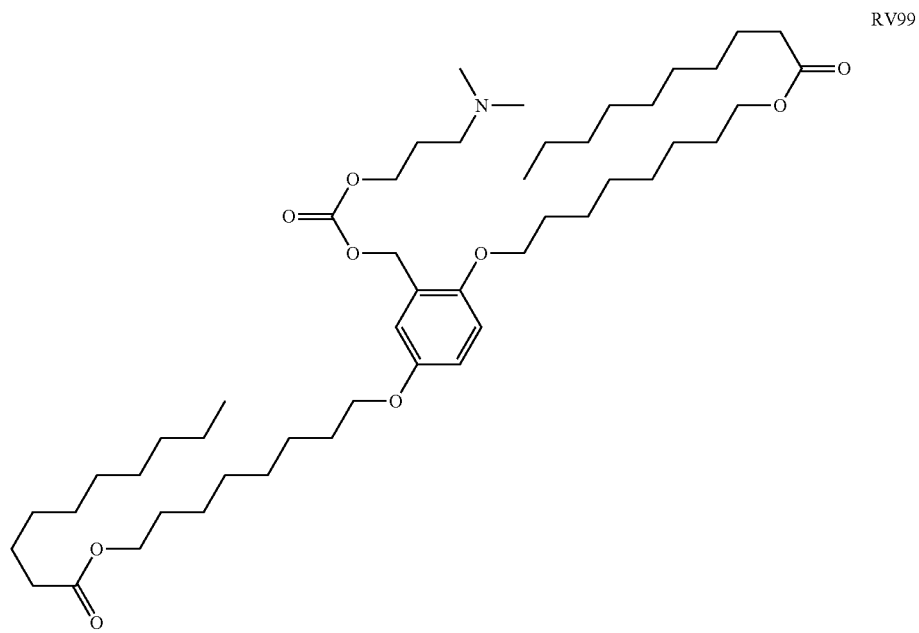 [SMILES: CCCCCCCCCC(=O)OCCCCCCCCOc1ccc(OCCCCCCCCOC(=O)CCCCCCCCC)c(COC(=O)OCCCN(C)C)c1]

In an embodiment, an exemplary cationic lipid is RV101 having the following structure:

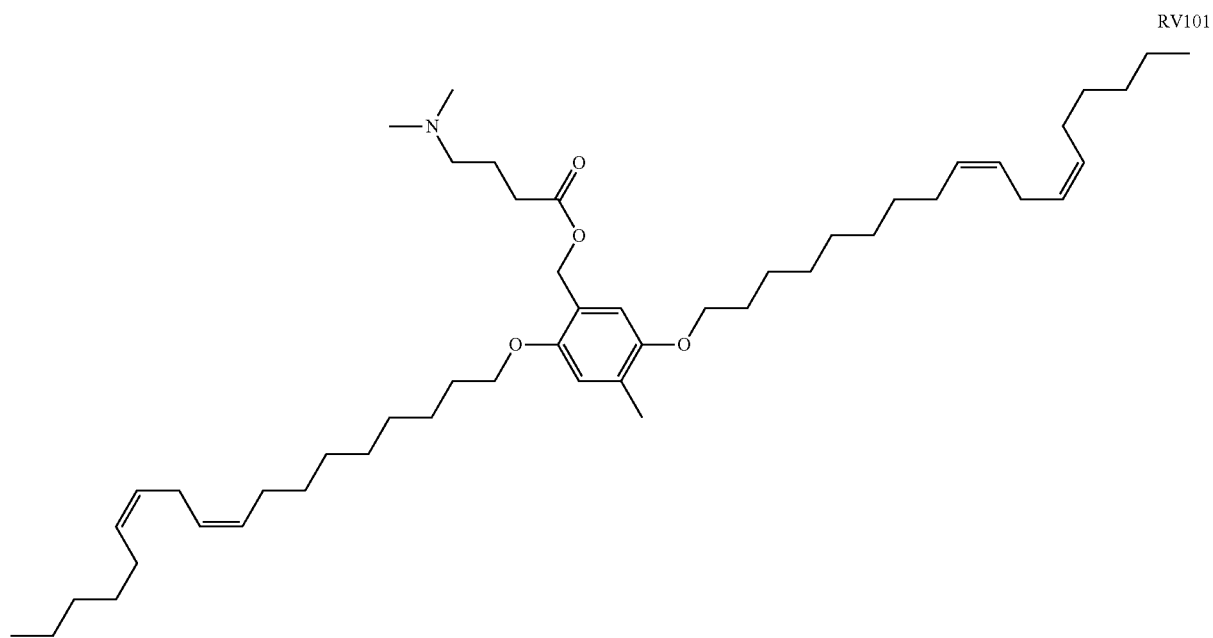 [SMILES: CCCCC/C=C\C/C=C\CCCCCCCCOc1cc(COC(=O)CCCN(C)C)c(OCCCCCCCC/C=C\C/C=C\CCCCC)cc1C]

In an embodiment, the cationic lipid is selected from the group consisting of: RV39, RV88, and RV94.

Compositions and methods for the synthesis of compounds having Formula I and RV28, RV31, RV33, RV37, RV39, RV42, RV44, RV73, RV75, RV81, RV84, RV85, RV86, RV88, RV91, RV92, RV93, RV94, RV95, RV96, RV97, RV99, and RV101 can be found in PCT/US2014/070882 (publication number WO/2015/095340) and PCT/US2014/070891 (publication number WO/2015/095346), filed 17 Dec. 2014; as well as PCT/US2015/048535 (publication number WO/2016/037053), filed 4 Sep. 2015.

The ratio of RNA to lipid can be varied. The ratio of nucleotide (N) to phospholipid (P) can be in the range of, e.g., 1N:1P, 2N:1P, 3N:1P, 4N:1P, 5N:1P, 6N:1P, 7N:1P, 8N:1P, 9N:1P, or 10N:1P. The ratio of nucleotide (N) to phospholipid (P) can be in the range of, e.g., 1N:1P to 10N:1P, 2N:1P to 8N:1P, 2N:1P to 6N:1P or 3N:1P to 5N:1P. Alternatively or additionally, the ratio of nucleotide (N) to phospholipid (P) is 4N:1P.

Alternatively or additionally, the nucleic acid-based vaccine comprises a cationic nanoemulsion (CNE) delivery system. Cationic oil-in water emulsions can be used to deliver negatively charged molecules, such as RNA molecules, to the interior of a cell. The emulsion particles comprise a hydrophobic oil core and a cationic lipid, the latter of which can interact with the RNA, thereby anchoring it to the emulsion particle. In a CNE delivery system, the nucleic acid molecule (e.g., RNA) which encodes the antigen is complexed with a particle of a cationic oil-in-water emulsion.

Thus, in a nucleic acid-based vaccine of the invention, an RNA molecule encoding a *Lyssavirus* antigen may be complexed with a particle of a cationic oil-in-water emulsion. The particles typically comprise an oil core (e.g. a plant oil or squalene) that is in liquid phase at 25° C., a cationic lipid (e.g. phospholipid) and, optionally, a surfactant (e.g. sorbitan trioleate, polysorbate 80); polyethylene glycol can also be included. Alternatively or additionally, the CNE comprises squalene and a cationic lipid, such as 1,2-dioleoyloxy-3-(trimethylammonio)propane (DOTAP). In an embodiment, the CNE is an oil in water emulsion of DOTAP and squalene stabilized with polysorbate The LNP and CNE delivery systems of the invention can be particularly effective in eliciting both humoral and cellular immune responses. Advantages of these delivery systems also include the absence of a limiting anti-vector immune response.

Pharmaceutical Compositions, Immunogenic Compositions

The disclosure provides compositions comprising a nucleic acid comprising a sequence which encodes a *Lyssavirus* polypeptide, for example a *Lyssavirus* antigen. The composition may be a pharmaceutical composition, e.g., an immunogenic composition or a vaccine composition. Accordingly, the composition may also comprise a pharmaceutically acceptable carrier. In some embodiments, the *Lyssavirus* is a rabies virus.

A "pharmaceutically acceptable carrier" includes any carrier that does not itself induce the production of antibodies harmful to the individual receiving the composition. The compositions of the invention may also contain a pharmaceutically acceptable diluent, such as water, sterile pyrogen-free water, saline, phosphate-buffered physiologic saline, glycerol, etc. Additionally, auxiliary substances, such as wetting or emulsifying agents, pH buffering substances, and the like, may be present.

Pharmaceutical compositions may include the constructs, nucleic acid sequences, and/or polypeptide sequences described elsewhere herein in plain water (e.g. water for injection "w.f.i.") or in a buffer e.g. a phosphate buffer, a Tris buffer, a borate buffer, a succinate buffer, a histidine buffer, or a citrate buffer. Buffer salts will typically be included in the 5-20 mM range. Pharmaceutical compositions may have a pH between 5.0 and 9.5, e.g. between 6.0 and 8.0. Compositions may include sodium salts, e.g. sodium chloride, to give tonicity.

A concentration of 10±2 mg/ml NaCl is typical, e.g. about 9 mg/ml. Compositions may include metal ion chelators. These can prolong RNA stability by removing ions which can accelerate phosphodiester hydrolysis. Thus a composition may include one or more of EDTA, EGTA, BAPTA, pentetic acid, etc. Such chelators are typically present at between 10-500 μM, e.g., 0.1 mM. A citrate salt, such as sodium citrate, can also act as a chelator, while advantageously also providing buffering activity.

Pharmaceutical compositions may have an osmolality of between 200 mOsm/kg and 400 mOsm/kg, e.g. between 240-360 mOsm/kg, or between 290-310 mOsm/kg. Pharmaceutical compositions may include one or more preservatives, such as thiomersal or 2-phenoxyethanol. Mercury-free compositions are preferred, and preservative-free vaccines can be prepared. Pharmaceutical compositions may be aseptic or sterile. Pharmaceutical compositions may be non-pyrogenic e.g. containing <1 EU (endotoxin unit, a standard measure) per dose, and preferably <0.1 EU per dose. Pharmaceutical compositions may be gluten free. Pharmaceutical compositions may be prepared in unit dose form. Alternatively or additionally, a unit dose may have a volume of between 0.1-2.0 ml, e.g. about 1.0 or 0.5 ml.

A composition of the invention may be administered with or without an adjuvant. Alternatively or additionally, the composition may comprise, or be administered in conjunction with, one or more adjuvants (e.g. vaccine adjuvants), in particular where the composition comprises an immunologically effective amount of a nucleic acid encoding a *Lyssavirus* antigen.

By "adjuvant" is meant an agent that augments, stimulates, activates, potentiates or modulates the immune response to an active ingredient of the composition. The adjuvant effect may occur at the cellular or humoral level or both. Adjuvants stimulate the response of the immune system to the actual antigen but have no immunological effect themselves. Alternatively or additionally, adjuvented compositions of the invention may comprise one or more immunostimulants. By "immunostimulant" it is meant an agent that induces a general, temporary increase in a subject's immune response, whether administered with the antigen or separately.

Methods of Use/Uses

Methods are provided for inducing an immune response against a disease caused by a *Lyssavirus* in a subject in need thereof comprising a step of administering an immunologically effective amount of a construct or composition as disclosed herein. In some embodiments are provided the use of the constructs or compositions disclosed herein for inducing an immune response to a *Lyssavirus* antigen in a subject in need thereof. In some embodiments are provided use of the construct or composition as disclosed herein in the manufacture of a medicament inducing an immune response to a *Lyssavirus* in a subject.

By "subject" is intended a vertebrate, such as a mammal e.g. a human or a veterinary mammal. In some embodiments the subject is human.

Routes of Administration

Compositions disclosed herein will generally be administered directly to a subject. Direct delivery may be accomplished by parenteral injection, e.g. subcutaneously, intraperitoneally, intravenously, intramuscularly, intradermally, or to the interstitial space of a tissue. Self-amplifying RNA encoding *Lyssavirus* antigens can be given either prophylactically or therapeutically to individuals of all ages. When given prophylactically, e.g., administered to residents of or travelers to areas endemic for rabies, the dosing schedule may consist of three doses, two doses or one dose. Alternatively or additionally, one dose is administered prophylactically. When given therapeutically, e.g., administered after a rabies exposure, the dosing schedule may consist of five doses, four doses, three doses, two doses or one dose. In a preferred embodiment, one or two doses are administered therapeutically.

As used herein, administration of a composition "followed by" administration of a composition indicates that a time interval has elapsed between administration of a first composition and administration of a second composition, regardless of whether the first and second compositions are the same or different.

Processes of Manufacturing and Formulations

Alternatively or additionally, the process of manufacturing a self-amplifying RNA comprises a step of in vitro transcription (IVT). In some embodiments, the process of manufacturing a self-amplifying RNA comprises a step of IVT to produce an RNA, followed by a capping 5' dinucleotide m7G(5')ppp(5')G reaction and further comprises a step of combining the RNA with a non-viral delivery system. Alternatively or additionally, the process of manufacturing a self-amplifying RNA comprises a step of IVT to produce an RNA, and further comprises a step of combining the RNA with a lipid based delivery system.

Sequence Identity

Identity with respect to a sequence is defined herein as the percentage of amino acid residues in the candidate sequence that are identical with the reference amino acid sequence after aligning the sequences and introducing gaps, if necessary, to achieve the maximum percent sequence identity, and not considering any conservative substitutions as part of the sequence identity.

Sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM 250 or swgapdnamt can be used in conjunction with the computer program. In an embodiment, the gap opening penalty is 15, the gap extension penalty is 6.66, the gap separation penalty range is eight and the percent identity for alignment delay is 40. By way of example, the percent identity can be calculated as the total number of identical matches multiplied by 100 and then divided by the sum of the length of the longer sequence within the matched span and the number of gaps introduced into the shorter sequences in order to align the two sequences.

Where the present disclosure refers to a sequence by reference to a UniProt or GenBank accession code, the sequence referred to is the current version as of the filing date of the present application.

The skilled person will recognise that individual substitutions, deletions or additions to a protein which alters, adds or deletes a single amino acid or a small percentage of amino acids is an "immunogenic derivative" where the alteration(s) results in the substitution of an amino acid with a functionally similar amino acid or the substitution/deletion/addition of residues which do not impact the immunogenic function.

Conservative substitution tables providing functionally similar amino acids are well known in the art. In general, such conservative substitutions will fall within one of the amino-acid groupings specified below, though in some circumstances other substitutions may be possible without substantially affecting the immunogenic properties of the antigen. The following eight groups each contain amino acids that are typically conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

Suitably such substitutions do not occur in the region of an epitope, and do not therefore have a significant impact on the immunogenic properties of the antigen.

Immunogenic derivatives may also include those wherein additional amino acids are inserted compared to the reference sequence. Suitably such insertions do not occur in the region of an epitope, and do not therefore have a significant impact on the immunogenic properties of the antigen. One example of insertions includes a short stretch of histidine residues (e.g. 2-6 residues) to aid expression and/or purification of the antigen in question.

Immunogenic derivatives include those wherein amino acids have been deleted compared to the reference sequence. Suitably such deletions do not occur in the region of an epitope, and do not therefore have a significant impact on the immunogenic properties of the antigen.

The skilled person will recognise that a particular immunogenic derivative may comprise substitutions, deletions and additions (or any combination thereof).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "plurality" refers to two or more. Additionally, numerical limitations given with respect to concentrations or levels of a substance, such as solution component concentrations or ratios thereof, and reaction conditions such as temperatures, pressures and cycle times are intended to be approximate. The term "about" used herein is intended to mean the amount±10%.

The present invention will now be further described by means of the following non-limiting examples. The results shown in the Examples below demonstrate that self-amplifying RNA encoding Lyssaviral antigens convey potent and long-lasting immunity when formulated in various lipid compositions. Their ease of manufacture, effectiveness at low doses and superiority to existing vaccines provides a significant breakthrough in rabies prevention and post-exposure treatment.

EXAMPLES

Example 1: Construct Design of SAM with *Lyssavirus* Antigens

The present inventors initiated work on a *Lyssavirus* vaccine using synthetic, self-amplifying mRNA ("SAM") derived from alphavirus replicons. The SAM vector derived from VEE TC-83 (SEQ ID NO: 1) was chosen as the backbone for cloning. Lyssaviral antigens of interest were expressed by this vector and evaluated for robust antigen production, immunogenicity, and efficacy using in vitro and in vivo models.

TABLE 1

SAM-Rabies G Protein Constructs

| | Rabies G Protein | SEQ ID NO |
|---|---|---|
| Construct 1 | Medoid | SEQ ID NO: 2 |
| | Flury HEP | SEQ ID NO: 3 |

TABLE 1-continued

SAM-Rabies G Protein Constructs

| | Rabies G Protein | SEQ ID NO |
|---|---|---|
| Construct 2 | Flury LEP | SEQ ID NO: 4 |
| | RABAVERT | SEQ ID NO: 5 |
| Construct 3 | Codon optimized | SEQ ID NO: 6<br>SEQ ID NO: 7 |
| Construct 4 | Codon pair optimized | SEQ ID NO: 8<br>SEQ ID NO: 9 |

Figure 1A:
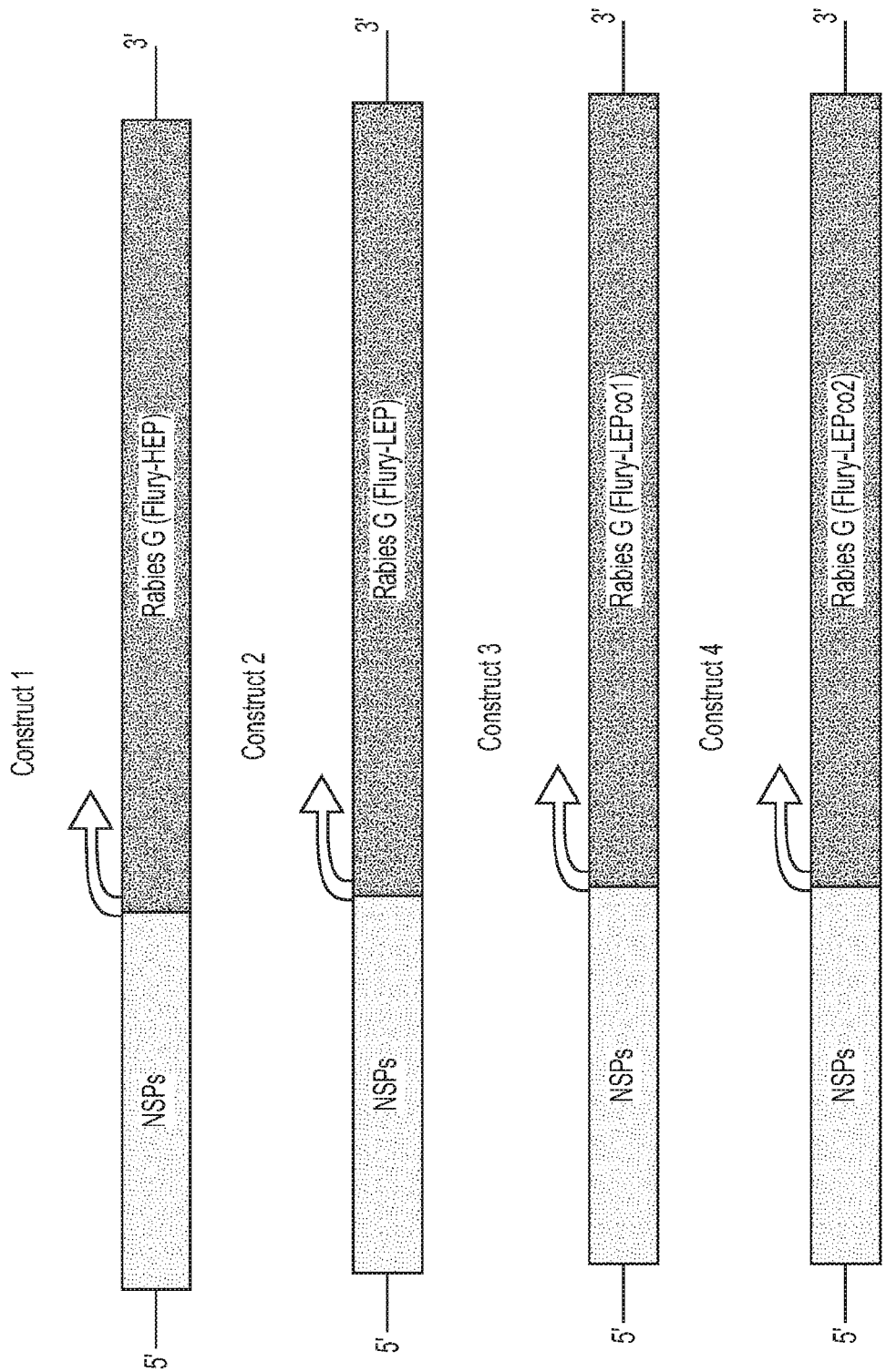
FIG. 1A. Schematic representation of SAM Rabies constructs. "NSP" denotes viral RNA encoding non-structural proteins. The rabies G antigen is encoded 3' to the NSP. Construct 1: Flury HEP Rabies G; Construct 2: Flury LEP Rabies G; Construct 3: codon optimized Flury LEP Rabies G; Construct 4: codon pair optimized Flury LEP Rabies G.
Figure 1B:
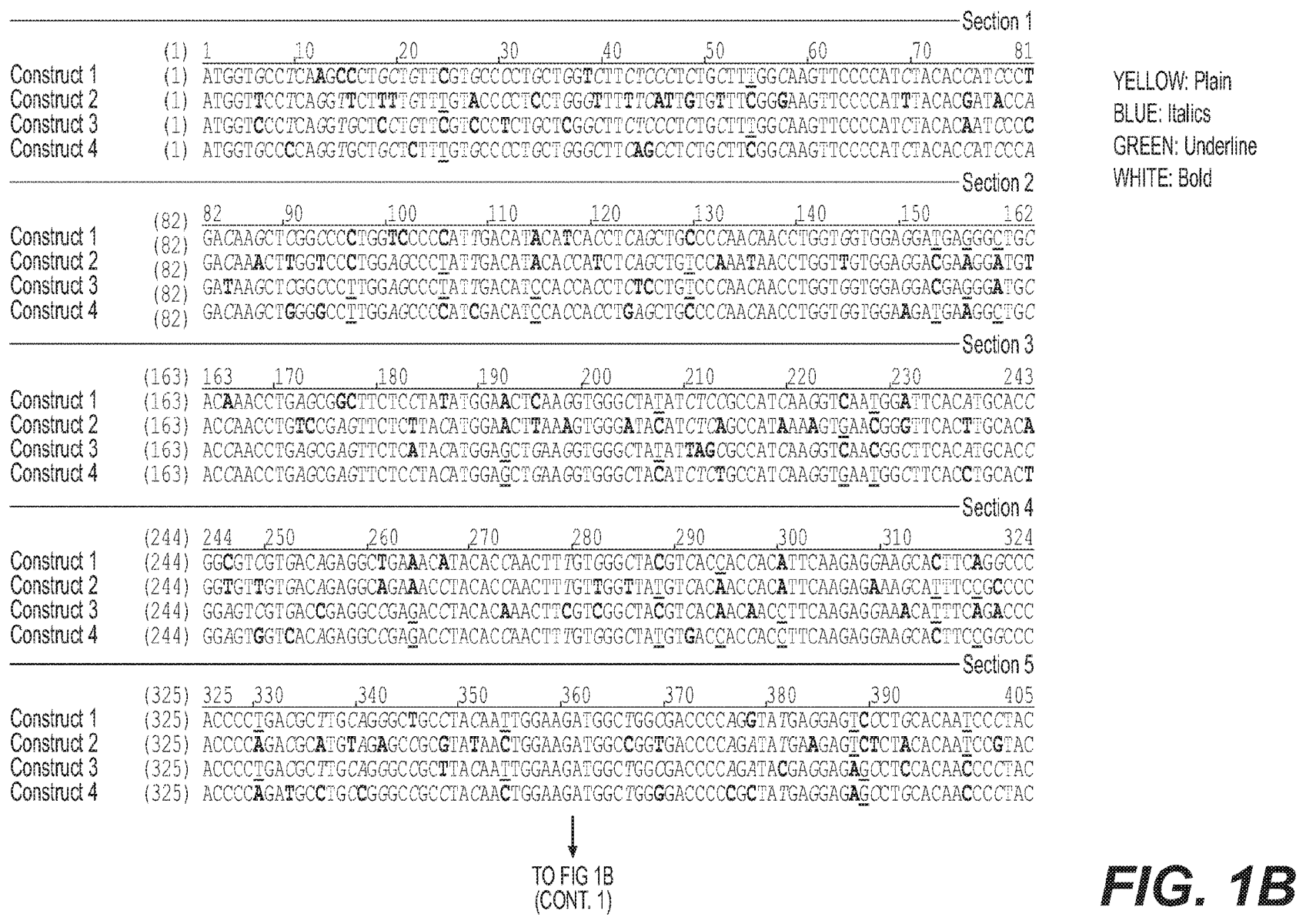
Figure 1B:
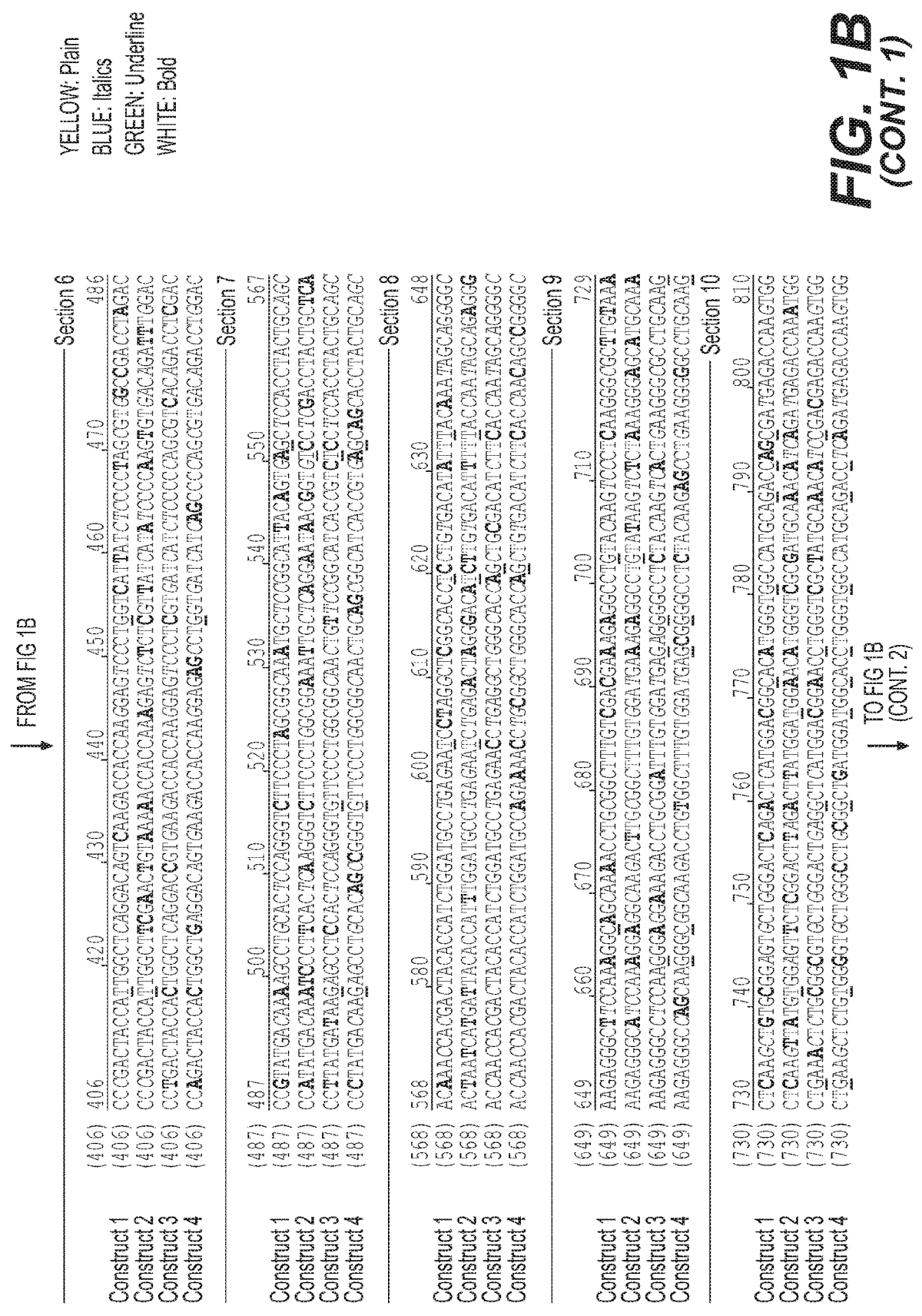
Figure 1B:
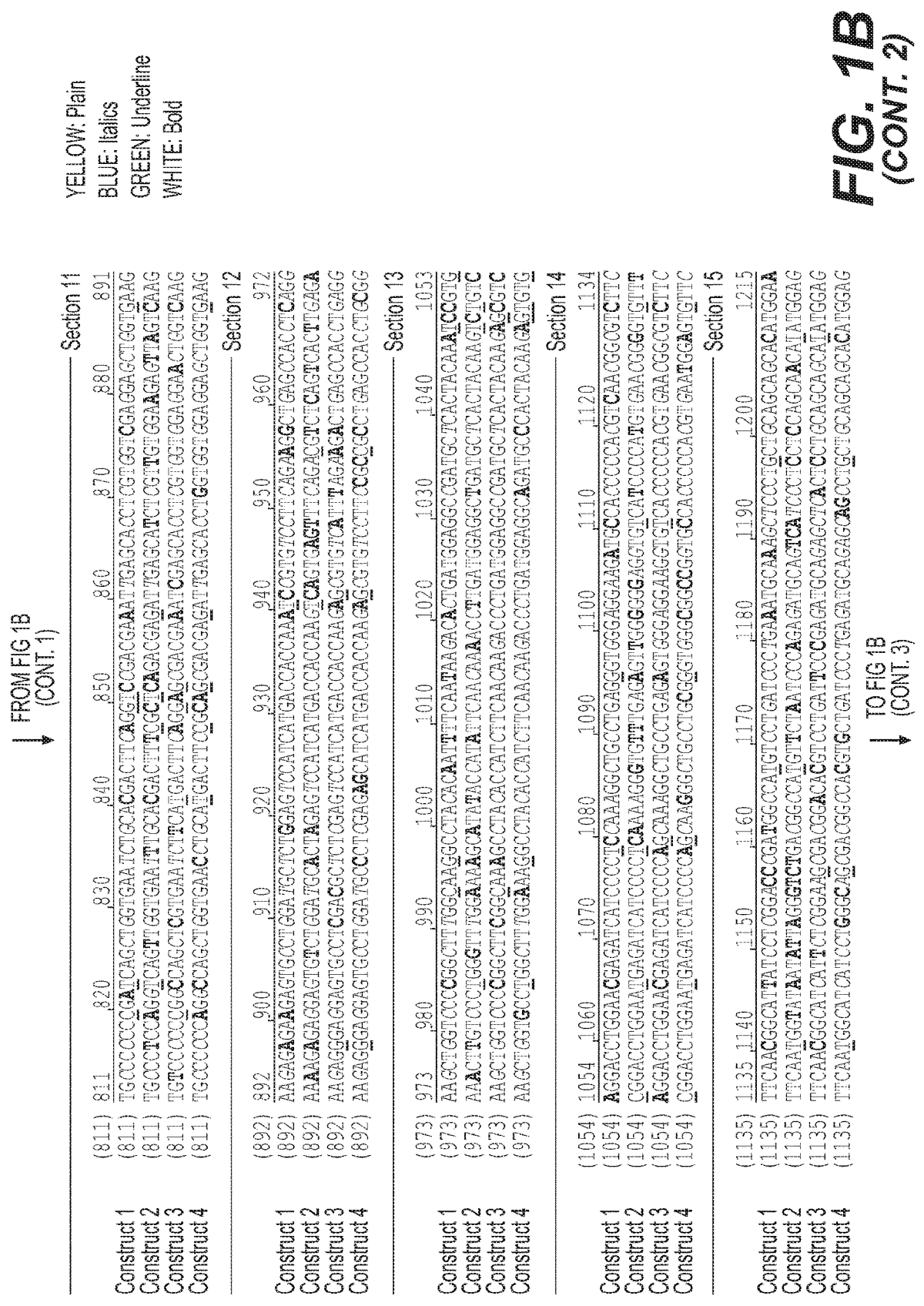
Figure 1B:
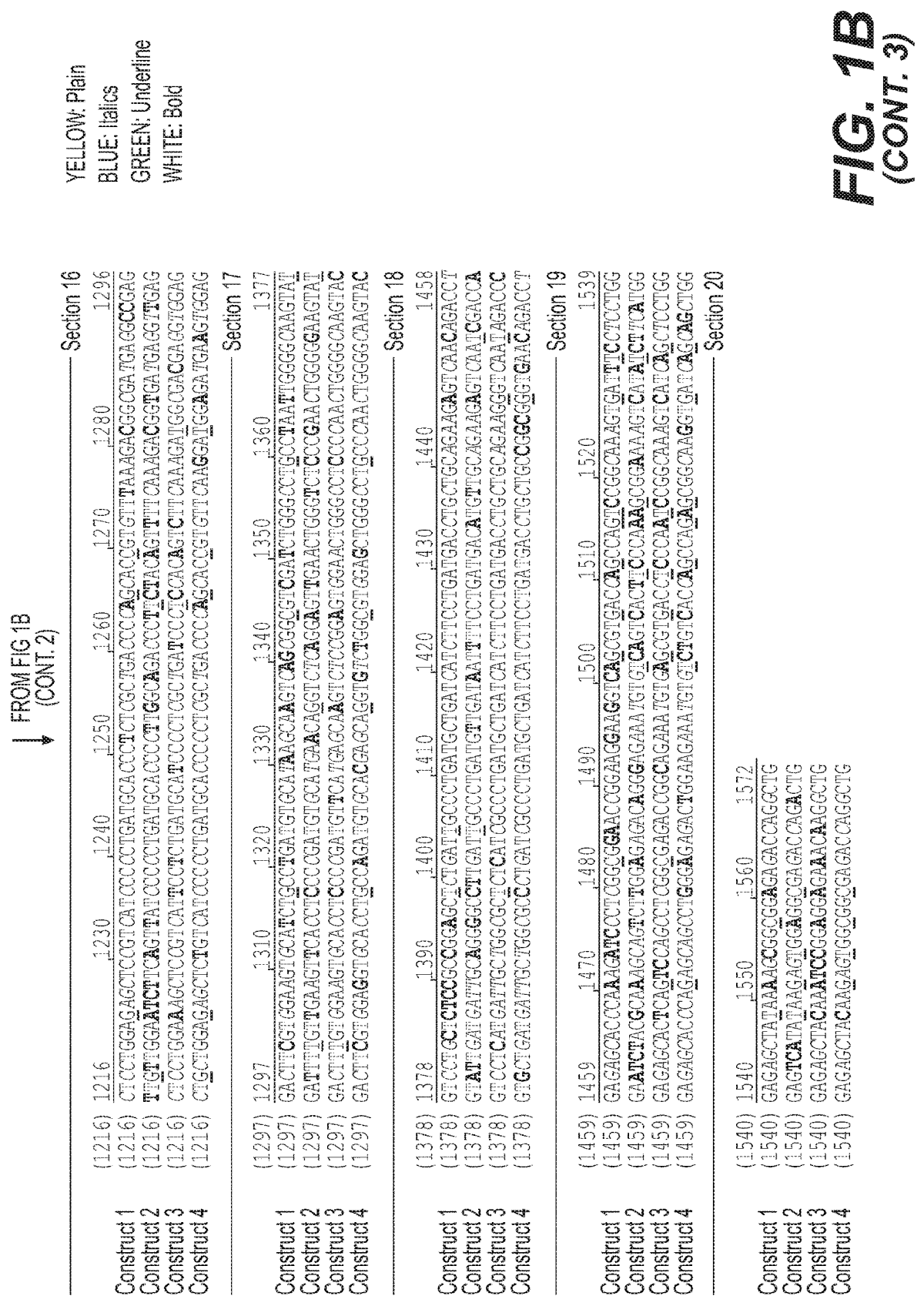

SAM Rabies constructs of the invention are exemplified by the constructs described in Table 1 and FIG. 1A. These constructs all express rabies full length glycoprotein ("G"). Construct 1 encodes a medoid G protein sequence and is closely related to the Flury-HEP and ERA strains of rabies virus. Construct 2 encodes the wild-type sequence of the Flury-LEP strain, which is the strain of the licensed RABAVERT vaccine (GenBank GU565703.1). Constructs 3 and 4 are derived from the wild-type sequence of the Flury-LEP strain. Construct 3 was codon optimized using a proprietary bioinformatics platform provided by GENEWIZ. Construct 4 was codon-pair optimized based on the table used for codon pair de-optimization described by Coleman et al. (2008) Science 320:1784. Codon pair optimization was performed manually without the use of bioinformatics tools or computational algorithms, using the high scores identified by Coleman et al. An aligned comparison of the DNA sequences of Constructs 1-4 is shown in FIG. 1B.

Example 2: In Vitro Expression of SAM Lyssaviral Antigens

Western blot analysis was performed to determine whether the transgenes were expressed from the SAM rabies constructs. BHK cells ($1 \times 10^6$) were transfected with 2.5 ug RNA from Constructs 1-4. After 20 hours, cell extracts were harvested and the production of rabies G protein was analysed by SDS gel electrophoresis followed by western blot analysis with the mouse anti-rabies glycoprotein antibody MAB8727 (Millipore Sigma, Billerica Mass., US). After incubation with primary antibody, the membrane was washed and then incubated with the peroxidase-conjugated anti-mouse antibody 115-035-003 (Jackson ImmunoResearch Laboratories, Inc., West Grove Pa., US). Finally the assay was developed by electrochemiluminescence (ECL) using standard techniques (GE Healthcare RPN2106, Little Chalfont, UK).

Figure 2A:
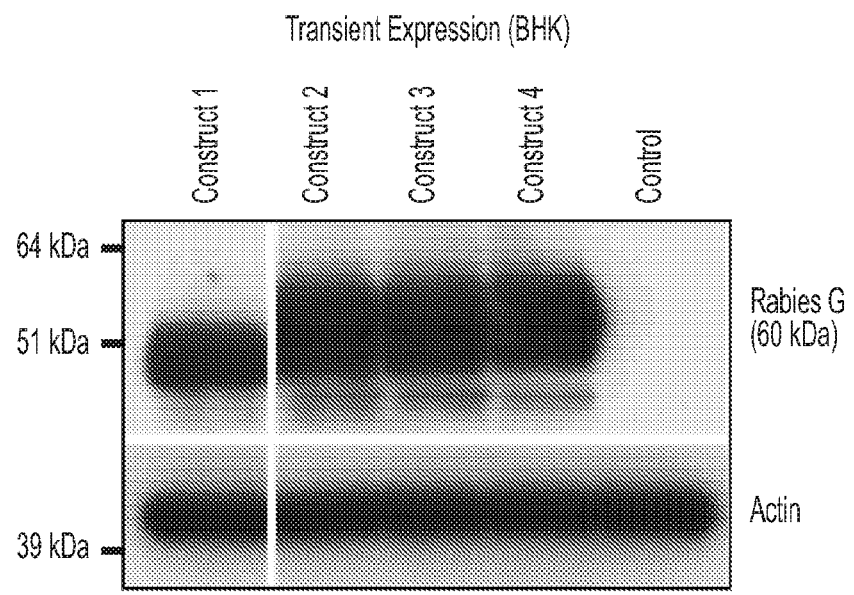
FIG. 2A. Western blot expression of rabies glycoprotein (G) antigen by Constructs 1-4 in BHK cells.

FIG. 2A demonstrates that BHK cells transfected with Constructs 1-4 all expressed rabies G protein. Molecular weight standards showing the location of 39 kDa, 51 kDa and 64 kDa proteins are indicated to the left of the blots. The lower band of 39 kDa is actin protein and was used as a standard for the total amount of protein in each lane. Each of the four constructs expressed rabies G protein, as shown in the first four lanes. The molecular weight of the protein expressed by Construct 1 is lower than that of the protein expressed by Constructs 2-4. This difference was attributed to a potentially different glycosylation pattern. Bioinformatic analysis predicts that Construct 1 contains two N-glycosylation sites and two O-glycosylation sites and that Constructs 2, 3 and 4 contain three or four N-glycosylation sites and five O-glycosylation sites.

Figure 2B:
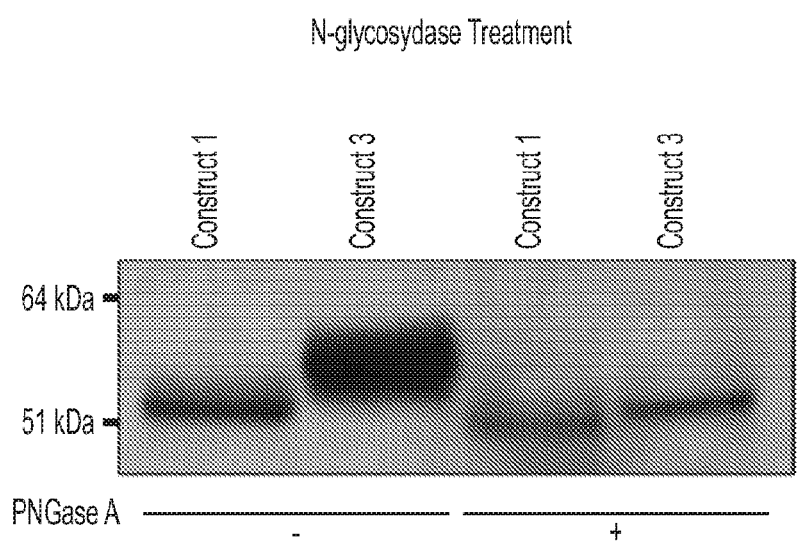
FIG. 2B. Western blot expression of rabies glycoprotein (G) antigen by Constructs 1 and 3 before and after treatment with peptide N-glycosidase A (PNGase A).

FIG. 2B demonstrates that treating these samples with peptide N-glycosidase A (PNGase A) to remove the N-linked carbohydrate chains markedly reduced the difference in molecular weight, indicating that a difference in N-glycosylation accounts for at least some of the observed difference in molecular weight.

Example 3: In Vivo Immunogenicity

Figure 3A:
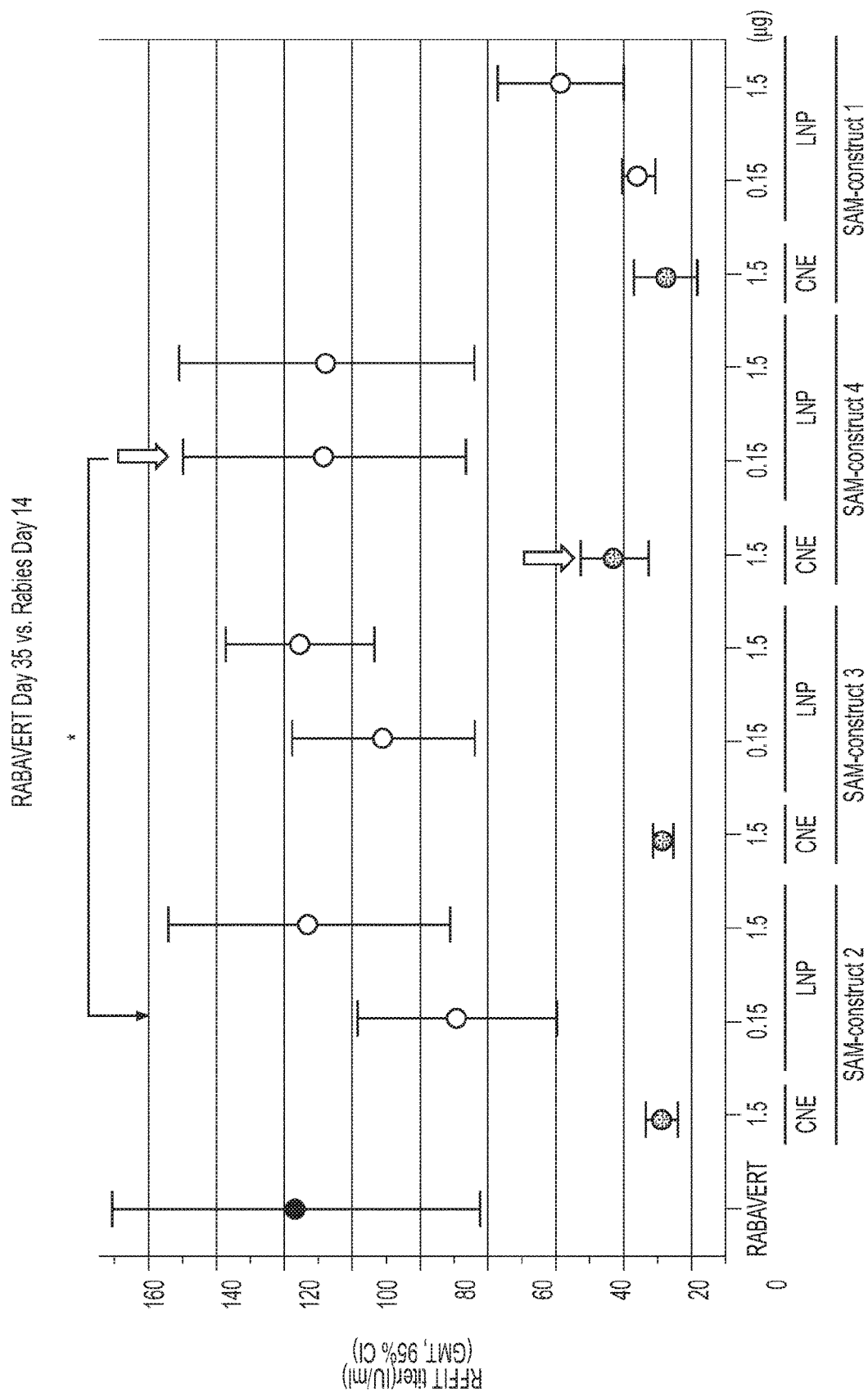
FIG. 3A. Neutralizing antibody (nAb) titers induced in Balb/c mice by SAM constructs 1-4 formulated with CNE or LNP on day 14 compared to RABAVERT at day 35 determined by Rapid Fluorescent Focus Inhibition Test (RFFIT) and expressed as Geometric Mean Titer (GMT).
Figure 3B:
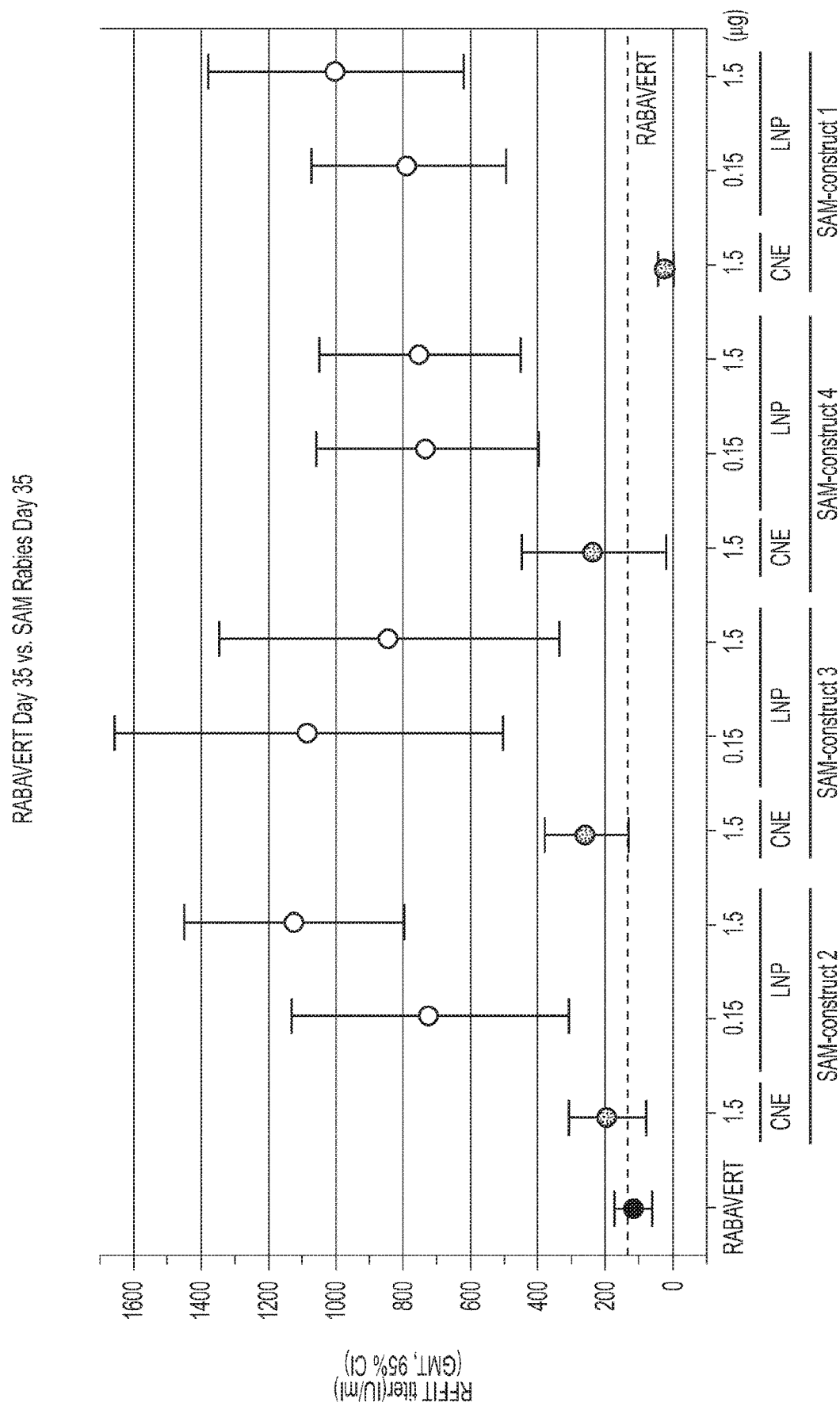
FIG. 3B. Neutralizing antibody (nAb) titers induced in Balb/c mice by SAM constructs 1-4 formulated with CNE or LNP on day 35 compared to RABAVERT at day 35 determined by Rapid Fluorescent Focus Inhibition Test (RFFIT) and expressed as Geometric Mean Titer (GMT).

The immunogenicity of the SAM rabies constructs was evaluated in parallel with RABAVERT in BALB/c mice (FIG. 3A and FIG. 3B). Each of the four constructs shown in FIG. 1A and Table 1 was formulated with either a cationic nanoemulsion (CNE) or a lipid nanoparticle (LNP). The animals were immunized on days 0 and 21 with the SAM vaccine constructs and on days 0, 7 and 21 with RABAVERT, according to the licensed RABAVERT dosing schedule. Each group consisted of 10 mice. Sera were collected on days 14 and 35 to evaluate the animals' immunogenicity against rabies. Serology was performed by the micro rapid Fluorescent Focus Inhibition Test for rabies (RFFIT) to determine the titer of anti-rabies neutralizing antibodies (nAb) (Smith et al. Bull. World Health Organ. 48:535 (1973)). The World Health Organization (WHO) guidelines recommend using the RFFIT to determine nAb titers and considers an Ab titer of 0.5 IU/ml to be an adequate response to a rabies vaccine (WHO Position Paper (2010) Vaccine 28:7140).

FIG. 3A shows the results of the serology test to detect neutralizing anti-rabies antibodies on day 14, i.e., two weeks after a single dose of the SAM rabies vaccines or 35 days after three doses of RABAVERT given on days 0, 7 and 21. Fourteen days post-immunization, one dose of the SAM rabies vaccines comprising constructs 2, 3 and 4 and formulated with LNP were as effective in eliciting neutralizing antibodies as three doses of RABAVERT, i.e. producing nAb titers of approximately 100 IU/ml. At 14 days post-immunization, the nAb titers of all tested constructs rose above the titer of 0.5 IU/ml, a surrogate marker of the threshold of effectiveness for protection against a naturally occurring rabies infection. This immunogenicity threshold has been documented to correlate with protection efficacy in humans and newborn pigs and has also been cited in a recent publication that used a mouse model (Schnee et al. (2016) PLoS Negl. Trop. Dis. 10:e0004746, e.g., at p. 15). The starred line (top of graph) indicates that the 0.15 ug dose of Construct 4 in LNP was statistically significantly more potent than the 0.15 ug dose of Construct 2 in LNP at day 14.

FIG. 3B shows the results of the serology test to detect neutralizing antibodies on day 35, i.e., two weeks following two doses of the SAM rabies vaccine administered on days 0 and 21 or three doses of RABAVERT administered on days 0, 7 and 21. The dotted line indicates the nAb titer in response to RABAVERT (approximately 100 IU/ml). (Note the difference in the scale of the RFFIT titers between FIG. 3A and FIG. 3B.) The 0.15 ug doses of Constructs 1, 2, 3 and 4 were all statistically significantly more potent than RABAVERT at day 35.

Thirty-five days post-immunization, two doses of the SAM rabies vaccines comprising Constructs 2, 3 and 4 formulated with 1.5 ug CNE were as effective in eliciting neutralizing antibodies as three doses of RABAVERT. Two doses of the SAM rabies constructs 2, 3 and 4 formulated with either 0.15 or 1.5 ug LNP RV39 markedly outperformed RABAVERT, producing approximately a ten-fold higher titer of neutralizing antibodies.

Example 4: SAM Rabies Vaccines Provide Long-Term Immunogenicity

Figure 4:
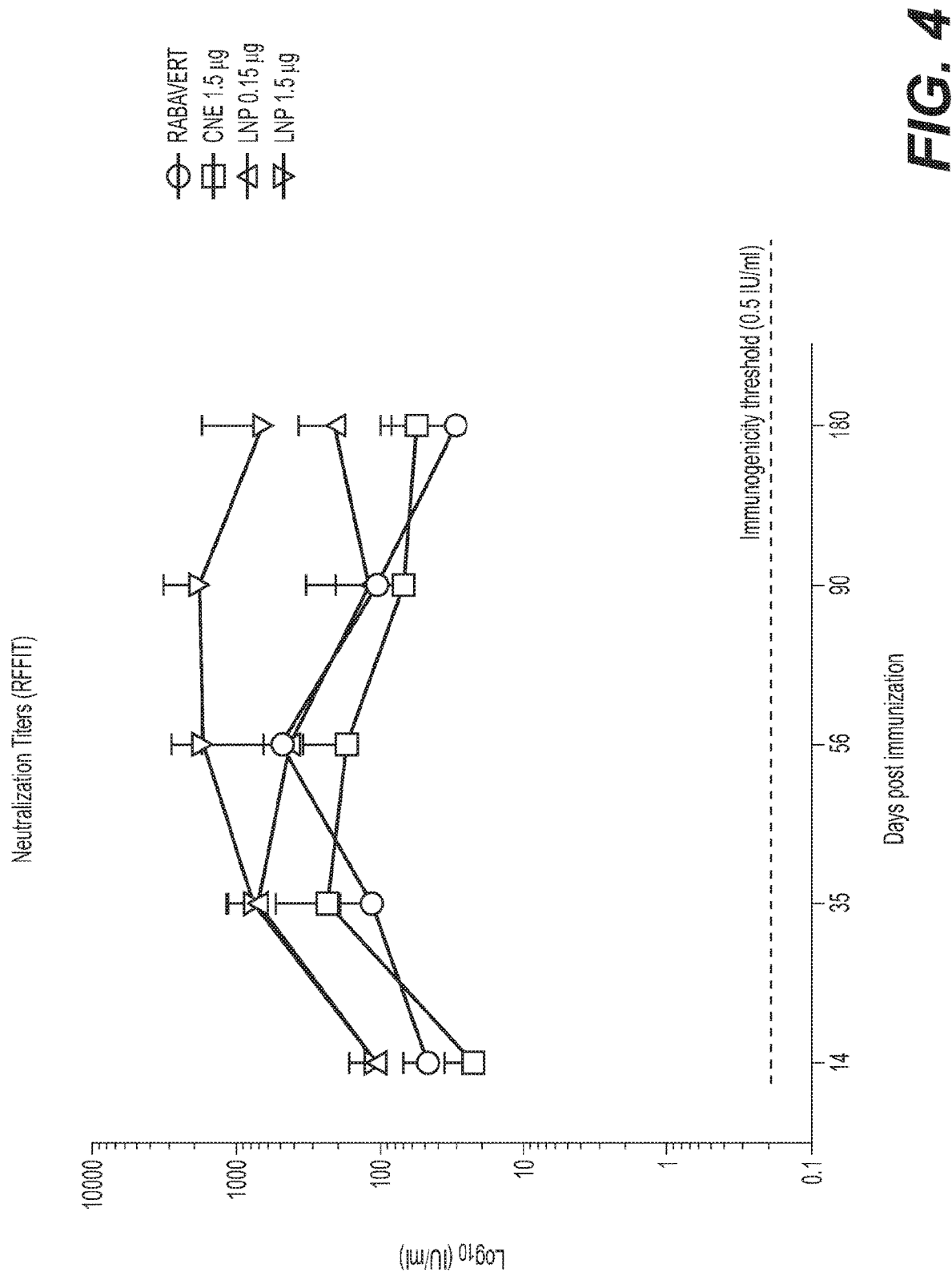
FIG. 4. Neutralizing antibody (nAb) titers determined by RFFIT in Balb/c mice of Construct 4 formulated with CNE or LNP for six months post immunization. RABAVERT (circles); 1.5 ug Construct 4 in CNE (squares); 0.15 ug Construct 4 in LNP (triangles); 1.5 ug Construct 4 in LNP (inverted triangles).

The ability of SAM rabies vaccines to confer long term immunogenicity was examined and the results are shown in FIG. 4. Construct 4 was formulated in amounts of 1.5 ug with CNE (square), 0.15 ug with LNP (triangle) or 1.5 ug with LNP (inverted triangle). RABAVERT (circle) was administered in three doses on days 0, 7 and 21 at a dilution factor of 1/25 of the human clinical dose. Neutralizing antibody titers of mice immunized with each of these formulations were measured by RFFIT at days 56, 90 and 180 days post-immunization. The dotted line denotes the threshold of immunogenicity for a rabies vaccine of 0.5 IU/ml.

At day 14, 1.5 ug Construct 4 RNA formulated with CNE, 0.15 ug Construct 4 RNA formulated with LNP or 1.5 ug Construct 4 RNA formulated with LNP elicited neutralizing antibodies to rabies at levels well above the immunogenicity threshold of effectiveness. By day 35 and at subsequent time points, the LNP-formulated SAM vectors elicited titers equal to or greater than that of RABAVERT. At day 35 and subsequent time points, each of the SAM Construct 4 vectors demonstrated immunogenicity equivalent or superior to RABAVERT. The LNP formulated vectors demonstrated a dose-dependent effect, the 1.5 ug dose formulated with RV39 was more potent than the 0.15 ug dose. By day 56, RABAVERT titers began to decline. In contrast, the titers of the SAM rabies constructs remained constant.

Immunogenicity was further examined in a dose range study and the results are shown in FIG. 5. In this study, decreasing doses of Construct 4 were formulated with either LNP or CNE. Construct 4 was formulated with LNP in decreasing amounts of 4.5 ug, 1.5 ug, 0.5 ug, 0.167 ug, 0.055 ug, 0.0185 ug, 0.006 ug, 0.002 ug or 0.0007 ug RNA or with CNE in amounts of 15 or 1.5 ug RNA. Balb/c mice were immunized either on days 0 and 21 with Construct 4 at the doses shown or on days 0, 7 and 21 with RABAVERT. Each group consisted of 10 mice. Sera were collected on days 14 and 35 and analysed by RFFIT for neutralizing antibodies. The immunogenicity threshold of effectiveness is indicated by the lower dashed line and the historically observed peak RABAVERT titer is indicated by the upper dashed lines in both panels.

Figure 5A:
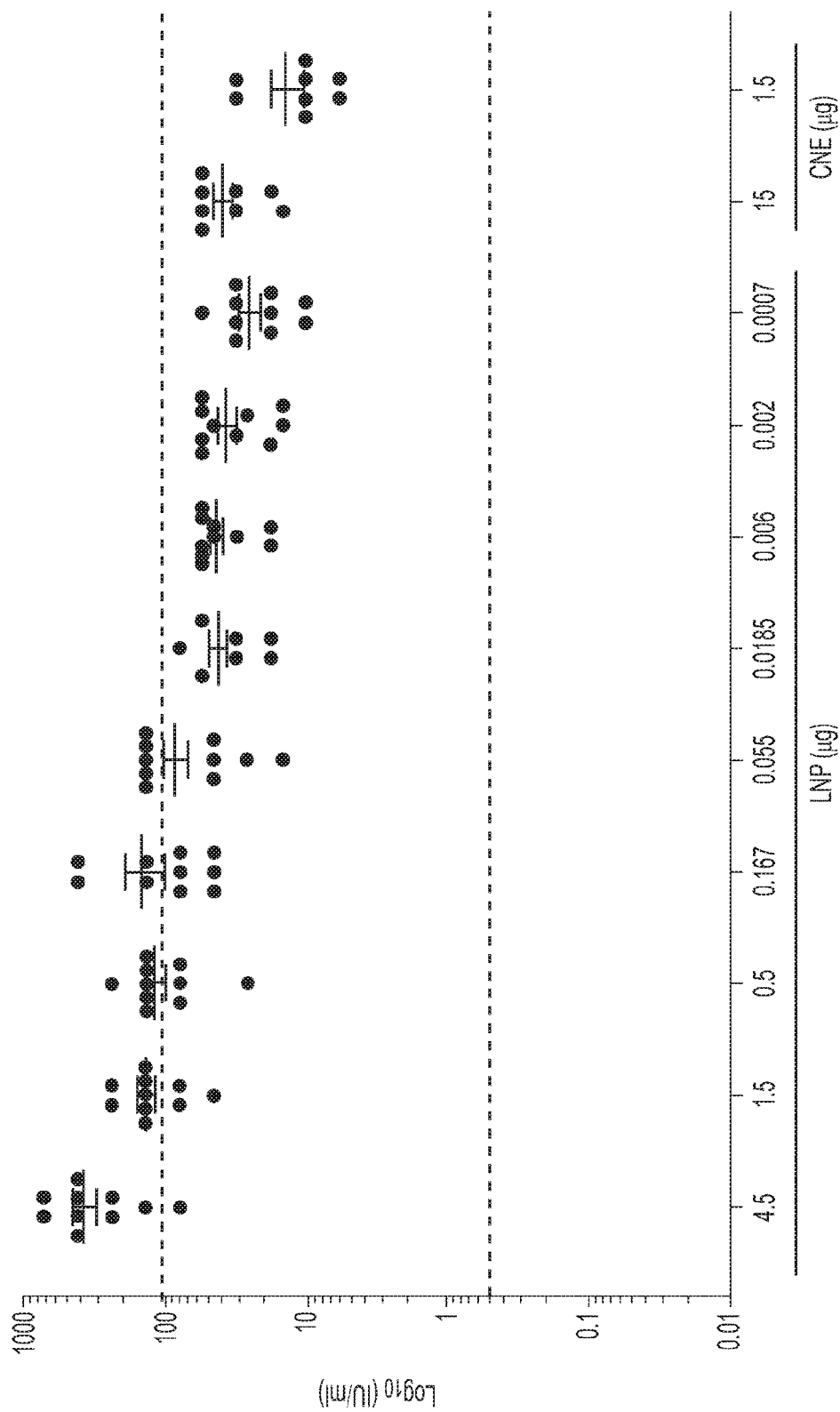
FIG. 5A. Day 14. Neutralizing antibody (nAb) titers determined by RFFIT in Balb/c mice of Construct 4 formulated with CNE or LNP, showing the dose response relationship with immunogenicity. The upper dashed line indicates a benchmark of 100 IU/ml, which is the peak nAb titer observed to be elicited by RABAVERT at high doses. The lower dashed line indicates the immunogenicity threshold of 0.5 IU/ml.

FIG. 5A demonstrates that at 14 days post-immunization, one dose of SAM rabies in amounts of 0.055 to 4.5 ug RNA, formulated with LNP was as effective as RABAVERT. Even at the very low doses of 2.0 ng and 0.7 ng RNA, mice immunized with SAM rabies formulated with LNP produced neutralizing antibodies well above the immunogenicity threshold for effectiveness, as did mice immunized with SAM rabies in amounts of 15 ug or 1.5 ug RNA when formulated with CNE. In contrast, when diluted one-thousand-fold, the effectiveness of RABAVERT fell almost to ineffective levels (data not shown).

Figure 5B:
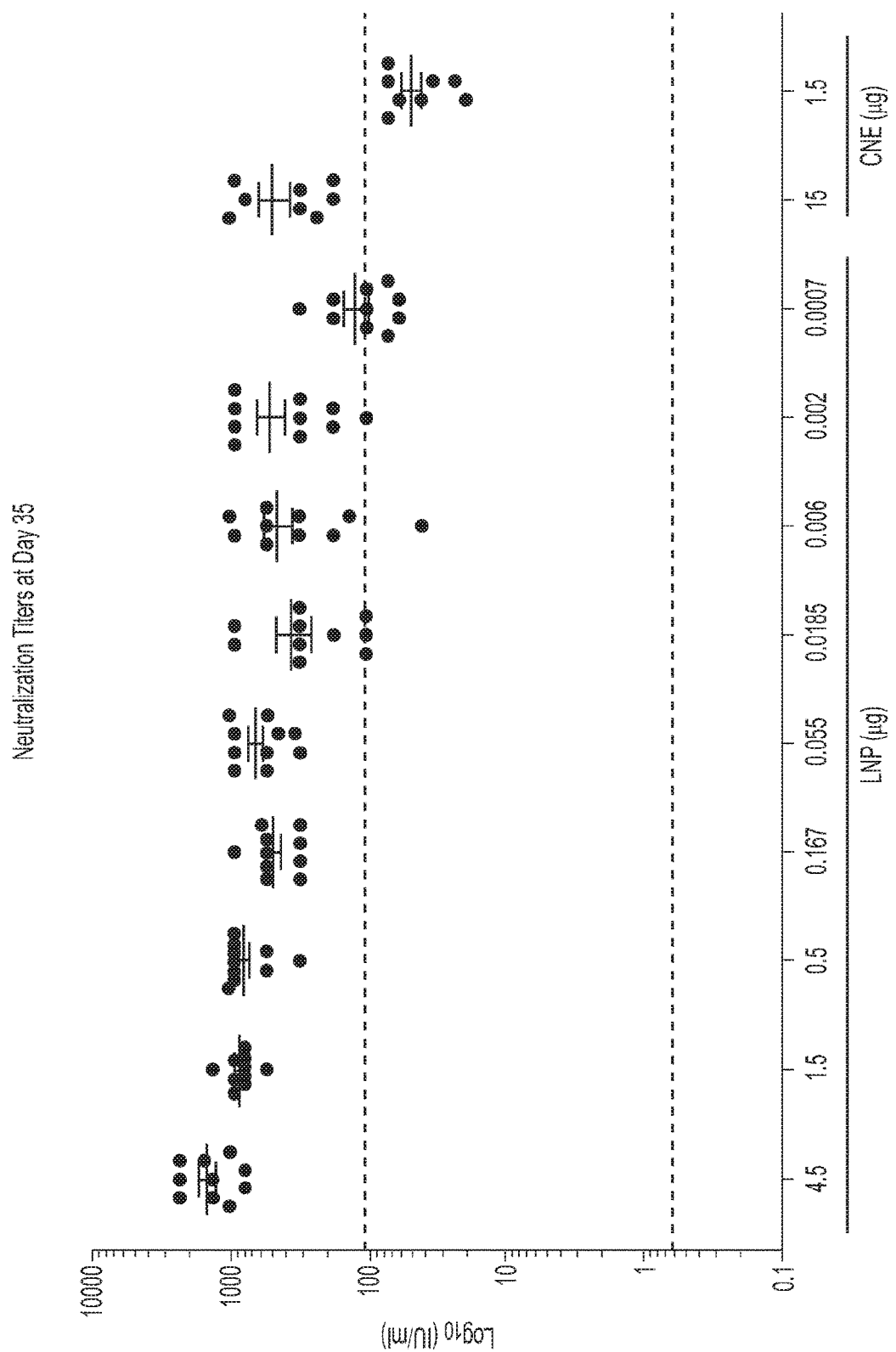
FIG. 5B. Day 35. Neutralizing antibody (nAb) titers determined by RFFIT in Balb/c mice of Construct 4 formulated with CNE or LNP, showing the dose response relationship with immunogenicity. The upper dashed line indicates a benchmark of 100 IU/ml, which is the peak nAb titer observed to be elicited by RABAVERT at high doses. The lower dashed line indicates the immunogenicity threshold of 0.5 IU/ml.

FIG. 5B shows the results of the serology test for detecting neutralizing antibodies on day 35, i.e., following two doses of the SAM rabies vaccine administered on days 0 and 21 or three doses of RABAVERT administered on days 0, 7 and 21. The potency of the SAM rabies vaccine increased at all doses and with both lipid formulations compared to the levels observed on day 14. At day 35, two doses of SAM rabies vaccine formulated in LNP, from the very low amount of 0.7 ng up to 4.5 ug RNA, significantly outperformed the three-dose regimen of RABAVERT. SAM rabies vaccine formulated in CNE at a dose of 15 ug RNA also outperformed RABAVERT.

Example 6: In Vivo Immunogenicity in Non-Human Primates

Both SAM LNP and SAM CNE formulations were well-tolerated and induced functional immune responses in non-human primates. Thirty five female rhesus macaques, between three years and four and one half years of age (>4.3 kg body weight) were immunized intramuscularly with either RABAVERT, Construct 4 formulated with CNE or Construct 4 formulated with LNP in the doses shown in Table 2. The RABAVERT dose was a full human dose and the dosing schedule was the same as that used in humans, i.e., weeks 0, 1 and 3. Serum was collected on days 1, 8, 15, 22, 36, 57, 71, 85, 113, 141, 169, 183 and 197 for RFFIT neutralization studies and measurement of total IgG by ELISA. Peripheral blood mononuclear cells (PBMC) were obtained from whole blood in days 1, 22, 36, 57, 71, 113, 141, 169, 183 and 197 for T cell intracellular cytokine staining (ICS) assays.

TABLE 2

SAM-Rabies G Protein Immunogenicity in Non-human Primates

| Group | No. Animals | Vaccine | Dose | Formulation | Dosing Regimen |
|---|---|---|---|---|---|
| 1 | 4 | RABAVERT | full human dose | N/A | Day 1, 8, 15 (weeks 0, 1, 3) |
| 2 | 4 | Construct 4 | 150 ug RNA | CNE56 | Day 1, 57, 169 (weeks 0, 8, 24) |
| 3 | 4 | Construct 4 | 75 ug RNA | CNE56 | |
| 4 | 4 | Construct 4 | 15 ug RNA | CNE56 | |
| 5 | 4 | Construct 4 | 3 ug RNA | CNE56 | |
| 6 | 5 | Construct 4 | 75 ug RNA | LNP RV39 | |
| 7 | 5 | Construct 4 | 15 ug RNA | LNP RV39 | |
| 8 | 5 | Construct 4 | 3 ug RNA | LNP RV39 | |

Figure 6:
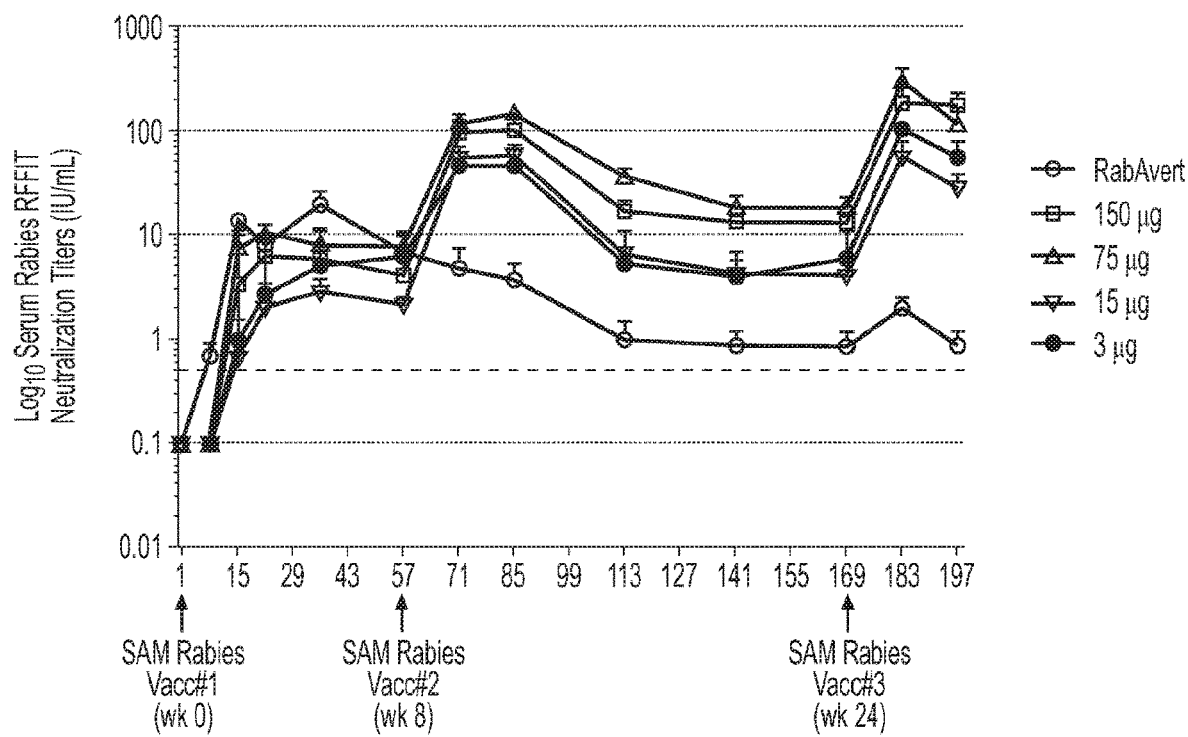
FIG. 6. Neutralizing antibody (nAb) titers determined by RFFIT in non-human primates of Construct 4 immunizations at weeks 0, 8 and 24 compared to a full human dose of RABAVERT immunizations at weeks 0, 1 and 3. The top panel shows the neutralizing anti-rabies antibody titers of four doses of Construct 4 formulated in CNE. 150 ug (squares); 75 ug (triangles); 15 ug (inverted triangles); 3 ug (solid circles); RABAVERT (open circles). The upper dashed line indicates the protective threshold of immunogenicity and the lower dotted line at log 0.1 indicates the lower limits of quantitation (LLOQ).
Figure 6:
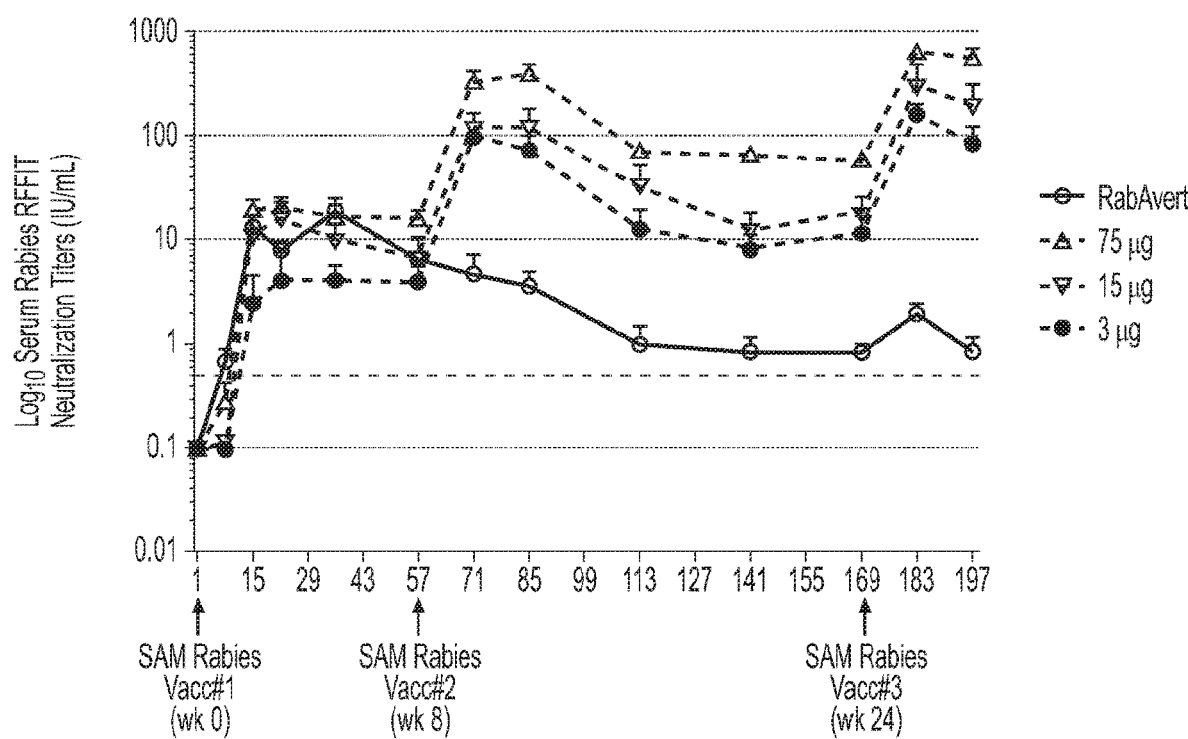

As shown in FIG. 6, both SAM rabies formulated in CNE and SAM rabies formulated in LNP induced high and long-lasting levels of rabies neutralizing antibodies as measured by RFFIT.

The top panel of FIG. 6 shows the neutralizing anti-rabies antibody titers of four doses of Construct 4 formulated in CNE, compared to RABAVERT. All four doses induced antibody levels well above the protective threshold (dashed line). The antibody levels were boosted by the second and third SAM vaccination and the boosted titers were superior to those achieved with RABAVERT. A dose response was observed; the 150 ug (open squares) and 75 ug (open triangles) doses produced higher antibody titers than the 15 (inverted open triangles) and 3 ug (solid circles) doses. Even at the very low dose of 3 ug RNA, Construct 4 formulated in CNE elicited a high and sustained neutralizing anti-rabies antibody titer at higher levels than RABAVERT (open circles).

The bottom panel of FIG. 6 shows the neutralizing anti-rabies antibody titers of four doses of Construct 4 formulated in LNP, compared to RABAVERT. The SAM LNP titers were higher than the SAM CNE titers. All three doses induced antibody levels well above the protective threshold (dashed line). The antibody levels were boosted by the second and third SAM vaccination and the boosted titers were superior to those achieved with RABAVERT. A dose response was observed with the 75 ug (open triangles), 15 ug (inverted open triangles) and 3 ug (solid circles) doses. Even at the very low dose of 3 ug RNA, Construct 4 formulated in LNP elicited a high and sustained neutralizing anti-rabies antibody titer at higher levels than RABAVERT (open circles).

As shown in FIG. 7, both SAM-RG-CNE and SAM-RG-LNP induced high and long-lasting levels of anti-rabies IgG, measured by a standard ELISA method. The IgG response followed a pattern similar to that of the neutralizing antibody response.

The top panel of FIG. 7 shows the rabies IgG binding antibody levels induced by Construct 4 formulated in CNE compared to RABAVERT. All four doses induced IgG levels well above the protective threshold (dashed line). The IgG levels were boosted by the second and third SAM vaccinations and the boosted titers were superior to those achieved with RABAVERT. A dose response was observed; the 150 ug (open squares) and 75 ug (open triangles) doses produced higher antibody titers than the 15 ug (inverted open triangles) and 3 ug (solid circles) doses. Even at the very low dose of 3 ug RNA, SAM-RG-co2 formulated in CNE elicited a high and sustained anti-rabies IgG titer at higher levels than RABAVERT (open circles).

The bottom panel of FIG. 7 shows the anti-rabies IgG titers of four doses of Construct 4 formulated in LNP, compared to RABAVERT. The SAM LNP titers were higher than the SAM CNE titers. All three doses induced antibody levels well above the protective threshold (dashed line). The antibody levels were boosted by the second and third SAM vaccinations and the boosted titers were superior to those achieved with RABAVERT. A dose response was observed with the 75 ug (open triangles), 15 ug (inverted open triangles) and 3 ug (solid circles) doses. Even at the very low dose of 3 ug RNA, Construct 4 formulated in LNP elicited a high and sustained anti-rabies IgG titer at higher levels than RABAVERT (open circles).

Example 7: Dose-Response of Construct 4 by RFFIT and ELISA

Experiment 1

Female Balb/C mice (6-8 weeks old) were vaccinated by intramuscular injection either with one-tenth the clinical dose of RABAVERT on days 1, 8 and 22, with Construct 4 on day 1 or with Construct 4 on days 1 and 22 at the doses shown in Table 3. Serum was collected on days 15, 36, 57, 91 and 181 and an RFFIT virus neutralization assay was performed.

TABLE 3

Dose Response of LNP Compared to CNE

| Group | Vaccine | Dose | Formulation | Injection (day) |
|---|---|---|---|---|
| 1 | RABAVERT | 1/10 clinical | LNP | 1, 8, 22 |
| 2 | Construct 4 | 1.5 ug | LNP | 1 |
| 3 | Construct 4 | 0.15 ug | LNP | 1 |
| 4 | Construct 4 | 0.015 ug | LNP | 1 |
| 5 | Construct 4 | 0.0015 ug | LNP | 1 |
| 6 | Construct 4 | 0.00015 ug | LNP | 1 |
| 7 | Construct 4 | 0.000015 ug | LNP | 1 |
| 8 | Construct 4 | 15 ug | CNE | 1 |
| 9 | Construct 4 | 1.5 ug | LNP | 1, 22 |
| 10 | Construct 4 | 0.15 ug | LNP | 1, 22 |
| 11 | Construct 4 | 0.015 ug | LNP | 1, 22 |
| 12 | Construct 4 | 0.0015 ug | LNP | 1, 22 |
| 13 | Construct 4 | 0.00015 ug | LNP | 1, 22 |
| 14 | Construct 4 | 0.000015 ug | LNP | 1, 22 |
| 15 | Construct 4 | 15 ug | CNE | 1, 22 |

The results of the RFFIT assay are shown in FIG. 8. The upper dotted line shows the protective threshold of 0.5 IU/ml neutralizing antibodies and the lower dotted line shows the lower limit of quantitation (LLOQ) of the assay (below log 0.1). A dose-response relationship was observed with both the one and two dose regimens. A single immunization with very low doses of SAM RNA, at least as low as 15 picograms, induced very high and stable levels of neutralizing antibodies (top panel). The levels were boosted by the second immunization and remained significantly higher than the neutralizing antibody levels induced by three doses of RABAVERT (bottom panel).

The results of the ELISA assay are shown in FIG. 8 and are similar to those observed with the RFFIT. The upper dotted line shows the protective threshold of 0.5 IU/ml neutralizing antibodies and the lower dotted line shows the lower limit of quantitation (LLOQ) of the assay (below log 0.1). A dose-response relationship was observed with both the one and two dose regimens. A single immunization with very low doses of SAM RNA, at least as low as 15 picograms, induced very high and stable levels of rabies IgG (top panel). The levels were boosted by the second immunization and remained significantly higher than the neutralizing antibody levels induced by three doses of RABAVERT (bottom panel).

Spleens were removed from five mice immunized with one 15 ug dose of Construct 4 formulated in CNE. Splenic T cells were stimulated with brefeldin A and intracellular cytokines were detected by flow cytometry. The cell mediated immune response is shown in FIG. 9. One dose of the SAM rabies CNE vaccine induced high levels of the Th1 cytokines IL2, TNF alpha, interferon gamma and CD107a, predominantly from CD8+ T cells (top panel) and also from CD4+ T cells (bottom panel), thus the T cell response was polyfunctional. The Th2 response (IL-4, IL-13) and the Th17 (IL-17A, IL-17F) responses were negligible.

Experiment 2

Female Balb/C mice (6-8 weeks old) were vaccinated by intramuscular injection either with one-tenth the clinical dose of RABAVERT on days 1, 8 and 22, with Construct 4 on day 1 or with Construct 4 on days 1 and 22 at the doses shown in Table 4 and formulated with either LNP RV29 or LNP RV94. Serum was collected on days 15, 36, 57, 91 and 181 and both an RFFIT virus neutralization assay and an ELISA assay for total IgG were performed.

TABLE 4

Dose Response of LNP RV29 and LNP RV94

| Group | Vaccine | Dose | Formulation | Injection (day) |
|---|---|---|---|---|
| 1 | RABAVERT | 1/10 clinical | | 1, 8, 22 |
| 2 | Construct 4 | 0.15 ug | LNP RV29 | 1, 22 |
| 3 | Construct 4 | 0.0015 ug | LNP RV29 | 1, 22 |
| 4 | Construct 4 | 0.000015 ug | LNP RV29 | 1, 22 |
| 5 | Construct 4 | 0.15 ug | LNP RV94 | 1, 22 |
| 6 | Construct 4 | 0.0015 ug | LNP RV94 | 1, 22 |
| 7 | Construct 4 | 0.000015 ug | LNP RV94 | 1, 22 |

The results of the RFFIT assay are shown in FIG. 10. The upper dotted line shows the protective threshold of 0.5 IU/ml neutralizing antibodies and the lower dotted line shows the lower limit of quantitation (LLOQ) of the assay (below log 0.1). Similar to the results in Experiment 1, very low doses of SAM RNA, at least as low as 15 picograms, induced very high and stable levels of neutralizing antibodies. The LNP RV39 and the LNP RV94 formulations induced similarly high neutralizing antibody levels.

The results of the ELISA assay are shown in FIG. 11 and, as in Experiment 1, are similar to those observed with the RFFIT. The upper dotted line shows the protective threshold of 0.5 IU/ml neutralizing antibodies and the lower dotted line shows the lower limit of quantitation (LLOQ) of the assay (below log 0.1). Very low doses of SAM RNA, at least as low as 15 picograms, induced very high and stable levels of rabies IgG.

Therapeutics administered by intramuscular injection in animals should be scaled to humans according to relative body weight (FDA Guidance for Industry: Estimating the Maximum Safe Starting Dose in Initial Clinical Trials for Therapeutics in Adult Healthy Volunteers (2005) US Dept. Health and Human Services; Nair et al. J Basic Clin. Pharma. 7:27-31 (2016)). An average adult body weight of 50 kg and an average mouse body weight of 20 grams was used to convert a low dose (i.e. 15 picograms) of mRNA administered using the SAM LNP platform to adult humans based on body weight. Using these average body weights, a scaling factor of 2500 is obtained (50,000 grams/20 grams=2500). Using this scaling factor to convert a mouse dose of vaccine into an equivalent dose in humans based on body weight, the low dose of 15 picograms in the mouse is equivalent to a human dose of 38 nanograms ($3.8 \times 10^1$ grams). The calculation is: 15 picograms×2500=38 nanograms.

Therefore, based on the in vivo data generated in mice shown above and this mouse to human conversion, vaccines using the SAM LNP vaccine platform generate appropriate and effective immune responses at doses in the nanogram range in adult humans.

Example 8: SAM Rabies Vaccine Protects Against a Lethal Rabies Challenge

The capacity of SAM vaccines to protect against a lethal rabies viral challenge was tested and compared to a saline control. The lethal dose of the Ps P4 bat isolate live rabies virus was determined by titration and determined to be a 1:2.5 dilution of a stock virus at a concentration of $1 \times 10^4$ tissue culture infectious dose 50% ($TCID_{50}$/ml), delivered intramuscularly. Clinical signs of rabies were observed from days 7-12 and confirmed by a direct fluorescent antibody (DFA) test of the brains at necropsy on day 12.

Female ICR mice approximately 4-6 weeks old were immunized in groups of eight with SAM rabies vaccines in the formulations and dosage regimens shown in Table 5

TABLE 5

Lethal Rabies Challenge.

| Group | Vaccine | Dose | Formulation | Dosing Regimen (Days) |
|---|---|---|---|---|
| 1 | RABAVERT | 1/10th clinical dose | N/A | 1, 8, 22 |
| 2 | Saline | — | — | 1, 22 |
| 3 | Construct 4 | 1.5 ug | LNP RV39 | 1, 22 |
| 4 | Construct 4 | 1.5 ug | LNP RV94 | 1, 22 |
| 5 | Construct 4 | 1.5 ug | CNE56 | 1, 22 |
| 6 | Construct 4 | 1.5 ug | LNP RV39 | 1 |
| 7 | Construct 4 | 1.5 ug | LNP RV94 | 1 |
| 8 | Construct 4 | 1.5 ug | CNE56 | 1 |

Sixty days after the first immunization, the mice were challenged with a lethal dose of Ps P4 bat isolate live rabies, a 1:2.5 dilution of a stock virus at a concentration of $1 \times 10^4$ tissue culture infectious dose 50% ($TCID_{50}$/ml), delivered intramuscularly. All mice in the saline group showed clinical signs of rabies and 100% mortality was observed by day 8. None of the vaccinated mice showed any clinical signs of rabies and when they were sacrificed at day 31 post-challenge a DFA test confirmed the absence of rabies virus in their brains.

All of the SAM formulations were safe and well tolerated. Body weight was monitored and no significant aberrant changes in were observed. Injection site reaction was monitored at 6, 24 and 48 hours after each dose and graded according to the modified Draize method. All formulations were well tolerated and Draize scores were zero (no edema or erythema and eschar formation) for all of the LNP formulations.

RFFIT and ELISA assays were performed and the results were similar to those shown above. High levels of neutralizing antibodies and IgG were induced by a single immunization. Both LNP RV39 and LNP94 formulations were more potent in inducing neutralizing antibodies than CNE56. LNP RV39 and LNP RV94 induced similar levels of neutralizing antibodies. IgG levels correlated with neutralizing antibody levels.

We claim:

1. A composition comprising a self-amplifying RNA encoding a polypeptide comprising an antigen selected from one or more of a full-length *Lyssavirus* glycoprotein (G), RNA polymerase (L), matrix protein (M), nucleoprotein (N) or phosphoprotein (P), an immunogenic derivative or an immunogenic fragment thereof and a lipid nanoparticle delivery system comprising RV39.

2. The composition of claim 1, wherein the self-amplifying RNA is codon optimized.

3. The composition of claim 1, wherein the self-amplifying RNA is codon pair optimized.

4. The composition of claim 1, wherein the self-amplifying RNA comprises a nucleic acid sequence selected from the group consisting of SEQ ID NO: 2; SEQ ID NO: 4, SEQ ID NO: 6 and SEQ ID NO: 8.

5. The composition of claim 1, wherein the self-amplifying RNA encodes an amino acid sequence selected from the group consisting of SEQ ID NO: 3; SEQ ID NO: 5, SEQ ID NO: 7 and SEQ ID NO: 9.

6. The composition according to claim 1, comprising an RNA-based vaccine.

7. The composition according to claim 1, wherein the composition further comprises a nucleic acid sequence which encodes an additional antigen.

8. The composition according to claim 1, wherein the composition is pharmaceutically acceptable for administration to a subject in combination with a further composition which comprises a nucleic acid comprising a sequence which encodes an additional antigen.

9. The composition according to claim 1, wherein the composition comprises one or more adjuvants.

10. A method of inducing an immune response against a disease caused by a *Lyssavirus* in a subject in need thereof, which comprises administering to the subject an immunologically effective amount of the composition according to claim 1.

11. The method according to claim 10 wherein the subject is human.

* * * * *

SEQUENCE LISTING

<160> NUMBER OF SEQ ID NOS: 10

<210> SEQ ID NO 1
<211> LENGTH: 7746
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 1

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg acaagaaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccaccccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020
tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctattat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tcgacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg atcctccct tccatgaatt cgcctacgag agtctgagaa    2160
cacgaccagc cgctccttac caagtaccaa ccataggggt gtatggcgtg ccaggatcag    2220
```

```
gcaagtctgg catcattaaa agcgcagtca ccaaaaaaga tctagtggtg agcgccaaga    2280
aagaaaactg tgcagaaatt ataagggacg tcaagaaaat gaaagggctg acgtcaatg     2340
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg ttttttttaac atgatgtgcc    2520
tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg     2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg ttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg ccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg ccaccgaag    4080
gagtgattat aaatgctgct aacagcaaag acaacctgg cggagggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
```

```
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta aacgcctga gccgatcatc atcgaagagg   5160
aagaaggaga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt ccacccccgc   5520
caggcgtgaa tagggtgatc actagagagg agctcgaggc gcttacccccg tcacgcactc   5580 ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gcttttcaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
```

-continued

```
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtgataaggc gcgcccaccc agcggccgca tacagcagca attggcaagc tgcttacata   7620
gaactcgcgg cgattggcat gccgccttaa aatttttatt ttatttttct ttcttttcc    7680 gaatcggatt ttgtttttaa tatttcaaaa aaaaaaaaaa aaaaaaaaaa aaaaaaaaaa   7740
aaaaaa                                                              7746
```

<210> SEQ ID NO 2
<211> LENGTH: 1572
<212> TYPE: DNA
<213> ORGANISM: Rabies lyssavirus

<400> SEQUENCE: 2

```
atggtgcctc aagccctgct gttcgtgccc ctgctggtct tctccctctg ctttggcaag     60
ttccccatct acaccatccc tgacaagctc ggcccctggt cccccattga catacatcac    120
ctcagctgcc ccaacaacct ggtggtggag gatgagggct gcacaaacct gagcggcttc    180
tcctatatgg aactcaaggt gggctatatc tccgccatca aggtcaatgg attcacatgc    240
accggcgtcg tgacagaggc tgaaacatac accaactttg tgggctacgt caccaccaca    300
ttcaagagga agcacttcag gcccacccct gacgcttgca gggctgccta caattggaag    360
atggctggcg accccaggta tgaggagtcc ctgcacaatc cctaccccga ctaccattgg    420
ctcaggacag tcaagaccac caaggagtcc ctggtcatta tctcccctag cgtggccgac    480
ctagacccgt atgacaaaag cctgcactcc agggtcttcc ctagcggcaa atgctccggc    540
attacagtga gctccaccta ctgcagcaca aaccacgact acaccatctg gatgcctgag    600
aatcctaggc tcggcacctc ctgtgacata tttacaaata gcaggggcaa gagggcttcc    660
aaaggcagca aaacctgcgg ctttgtcgac gaaagaggcc tgtacaagtc cctcaagggc    720
gcttgtaaac tcaagctgtg cggagtgctg ggactcagac tcatggacgg cacatgggtg    780
gccatgcaga ccagcgatga gaccaagtgg tgcccccccg atcagctggt gaatctgcac    840
gacttcaggt ccgacgaaat tgagcacctc gtggtcgagg agctggtgaa gaagagagaa    900
gagtgcctgg atgctctgga gtccatcatg accaccaaat ccgtgtcctt cagaaggctg    960
agccacctca ggaagctggt ccccggcttt ggcaaggcct acacaatttt caataagaca   1020
ctgatggagg ccgatgctca ctacaaatcc gtgaggacct ggaacgagat catcccctcc   1080
aaaggctgcc tgagggtggg aggaagatgc cacccccacg tcaacggcgt cttcttcaac   1140
ggcattatcc tcggacccga tggccatgtc ctgatccctg aaatgcaaag ctccctgctg   1200
cagcagcaca tggaactcct ggagagctcc gtcatccccc tgatgcaccc tctcgctgac   1260
cccagcaccg tgtttaaaga cggcgatgag gccgaggact tcgtggaagt gcatctgcct   1320
```

```
gatgtgcata agcaagtcag cggcgtcgat ctgggcctgc ctaattgggg caagtatgtc    1380
ctgctctccg ccggagctct gattgccctg atgctgatca tcttcctgat gacctgctgc    1440
agaagagtca acagacctga gcacccaa agatccctcg gcggaaccgg aaggaaggtc      1500
agcgtgacca gccagtccgg caaagtgatt tcctcctggg agagctataa aagcggcgga    1560
gagaccaggc tg                                                       1572
```

<210> SEQ ID NO 3
<211> LENGTH: 524
<212> TYPE: PRT
<213> ORGANISM: Rabies lyssavirus

<400> SEQUENCE: 3

```
Met Val Pro Gln Ala Leu Leu Phe Val Pro Leu Leu Val Phe Ser Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Lys Ser Leu His Ser Arg Val Phe Pro Ser Gly
                165                 170                 175

Lys Cys Ser Gly Ile Thr Val Ser Ser Thr Tyr Cys Ser Thr Asn His
            180                 185                 190

Asp Tyr Thr Ile Trp Met Pro Glu Asn Pro Arg Leu Gly Thr Ser Cys
        195                 200                 205

Asp Ile Phe Thr Asn Ser Arg Gly Lys Arg Ala Ser Lys Gly Ser Lys
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320
```

Ser His Leu Arg Lys Leu Val Pro Gly Phe Gly Lys Ala Tyr Thr Ile
            325                 330                 335

Phe Asn Lys Thr Leu Met Glu Ala Asp Ala His Tyr Lys Ser Val Arg
        340                 345                 350

Thr Trp Asn Glu Ile Ile Pro Ser Lys Gly Cys Leu Arg Val Gly Gly
    355                 360                 365

Arg Cys His Pro His Val Asn Gly Val Phe Phe Asn Gly Ile Ile Leu
370                 375                 380

Gly Pro Asp Gly His Val Leu Ile Pro Glu Met Gln Ser Ser Leu Leu
385                 390                 395                 400

Gln Gln His Met Glu Leu Leu Glu Ser Ser Val Ile Pro Leu Met His
            405                 410                 415

Pro Leu Ala Asp Pro Ser Thr Val Phe Lys Asp Gly Asp Glu Ala Glu
        420                 425                 430

Asp Phe Val Glu Val His Leu Pro Asp Val His Lys Gln Val Ser Gly
    435                 440                 445

Val Asp Leu Gly Leu Pro Asn Trp Gly Lys Tyr Val Leu Leu Ser Ala
450                 455                 460

Gly Ala Leu Ile Ala Leu Met Leu Ile Ile Phe Leu Met Thr Cys Cys
465                 470                 475                 480

Arg Arg Val Asn Arg Pro Glu Ser Thr Gln Arg Ser Leu Gly Gly Thr
            485                 490                 495

Gly Arg Lys Val Ser Val Thr Ser Gln Ser Gly Lys Val Ile Ser Ser
        500                 505                 510

Trp Glu Ser Tyr Lys Ser Gly Gly Glu Thr Arg Leu
    515                 520

<210> SEQ ID NO 4
<211> LENGTH: 1572
<212> TYPE: DNA
<213> ORGANISM: Rabies lyssavirus

<400> SEQUENCE: 4
atggttcctc aggttctttt gtttgtaccc ctcctgggtt tttcattgtg tttcgggaag     60
ttccccattt tacacgatacc agacaaactt ggtccctgga gccctattga catacaccat    120
ctcagctgtc caaataacct ggttgtggag gacgaaggat gtaccaacct gtccgagttc    180
tcttacatgg aacttaaagt gggatacatc tcagccataa agtgaacgg ttcacttgc     240
acaggtgttg tgacagaggc agaaacctac ccaactttg ttggttatgt cacaaccaca    300
ttcaagagaa agcatttccg ccccacccca gacgcatgta gagccgcgta taactggaag    360
atggccggtg accccagata tgaagagtct ctacacaatc cgtaccccga ctaccattgg    420
cttcgaactg taaaaaccac caaagagtct ctcgttatca tatccccaag tgtgacagat    480
ttggacccat atgacaaatc ccttcactca agggtcttcc ctggcggaaa ttgctcagga    540
ataacggtgt cctcgaccta ctgctcaact aatcatgatt acaccatttg gatgcctgag    600
aatctgagac tagggacatc ttgtgacatt tttaccaata gcagagggaa gagggcatcc    660
aaaggaggca agacttgcgg ctttgtggat gaaagaggcc tgtataagtc tctaaaggga    720
gcatgcaaac tcaagttatg tggagttctc ggacttagac ttatggatgg aacatgggtc    780
gcgatgcaaa catcagatga gaccaaatgg tgccctccag gtcagttggt gaatttgcac    840
gactttcgct cagacgagat tgagcatctc gttgtggaag agttagtcaa gaaaagagag    900
gagtgtctgg atgcactaga gtccatcatg accaccaagt cagtgagttt cagacgtctc    960

```
agtcacttga gaaaacttgt ccctgggttt ggaaaagcat ataccatatt caacaaaacc    1020
ttgatggagg ctgatgctca ctacaagtct gtccggacct ggaatgagat catcccctca    1080
aaagggtgtt tgagagttgg ggggaggtgt catccccatg tgaacggggt gtttttcaat    1140
ggtataatat tagggtctga cggccatgtt ctaatcccag agatgcagtc atccctcctc    1200
cagcaacata tggagttgtt ggaatcttca gttatccccc tgatgcaccc cttggcagac    1260
ccttctacag ttttcaaaga cggtgatgag gttaggatt tgttgaagt tcacctcccc     1320 gatgtgcatg aacaggtctc aggagttgaa ctgggtctcc cgaactgggg gaagtatgta    1380
ttgatgattg caggggcctt gattgccctg atgttgataa ttttcctgat gacatgttgc    1440
agaagagtca atcgaccaga atctacgcaa agcagtcttg agagacagg gagaaatgtg     1500 tcagtcactt cccaaagcgg aaaagtcata tcttcatggg agtcatataa gagtggaggc    1560
gagaccagac tg                                                        1572
```

<210> SEQ ID NO 5
<211> LENGTH: 524
<212> TYPE: PRT
<213> ORGANISM: Rabies lyssavirus

<400> SEQUENCE: 5

```
Met Val Pro Gln Val Leu Leu Phe Val Pro Leu Leu Gly Phe Ser Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Glu Phe Ser Tyr Met Glu
    50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Asn Cys Ser Gly Ile Thr Val Ser Ser Thr Tyr Cys Ser Thr Asn His
            180                 185                 190

Asp Tyr Thr Ile Trp Met Pro Glu Asn Leu Arg Leu Gly Thr Ser Cys
        195                 200                 205

Asp Ile Phe Thr Asn Ser Arg Gly Lys Arg Ala Ser Lys Gly Gly Lys
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
```

```
            260                 265                 270
Pro Gly Gln Leu Val Asn Leu His Asp Phe Arg Ser Asp Glu Ile Glu
            275                 280                 285

His Leu Val Val Glu Glu Leu Val Lys Lys Arg Glu Glu Cys Leu Asp
            290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Arg Val Gly Gly
            355                 360                 365

Arg Cys His Pro His Val Asn Gly Val Phe Phe Asn Gly Ile Ile Leu
        370                 375                 380

Gly Ser Asp Gly His Val Leu Ile Pro Glu Met Gln Ser Ser Leu Leu
385                 390                 395                 400

Gln Gln His Met Glu Leu Leu Glu Ser Ser Val Ile Pro Leu Met His
                405                 410                 415

Pro Leu Ala Asp Pro Ser Thr Val Phe Lys Asp Gly Asp Glu Val Glu
            420                 425                 430

Asp Phe Val Glu Val His Leu Pro Asp Val His Glu Gln Val Ser Gly
        435                 440                 445

Val Glu Leu Gly Leu Pro Asn Trp Gly Lys Tyr Val Leu Met Ile Ala
    450                 455                 460

Gly Ala Leu Ile Ala Leu Met Leu Ile Ile Phe Leu Met Thr Cys Cys
465                 470                 475                 480

Arg Arg Val Asn Arg Pro Glu Ser Thr Gln Ser Ser Leu Gly Glu Thr
                485                 490                 495

Gly Arg Asn Val Ser Val Thr Ser Gln Ser Gly Lys Val Ile Ser Ser
            500                 505                 510

Trp Glu Ser Tyr Lys Ser Gly Gly Glu Thr Arg Leu
            515                 520

<210> SEQ ID NO 6
<211> LENGTH: 1572
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atggtccctc aggtgctcct gttcgtccct ctgctcggct ctccctctg ctttggcaag       60 ttccccatct acacaatccc cgataagctc ggcccttgga gccctattga catccaccac      120
ctctcctgtc ccaacaacct ggtggtggag gacgagggat gcaccaacct gagcgagttc      180
tcatacatgg agctgaaggt gggctatatt agcgccatca aggtcaacgg cttcacatgc      240
accggagtcg tgaccgaggc cgagacctac acaaacttcg tcggctacgt cacaacaacc      300
ttcaagagga acatttcag acccaccccct gacgcttgca gggccgctta caattggaag      360
atggctggcg accccagata cgaggagagc ctccacaacc cctaccctga ctaccactgg      420
ctcaggaccg tgaagaccac caaggagtcc ctcgtgatca tctcccccag cgtcacagac      480 ctcgacccttt atgataagag cctccactcc agggtgttcc ctggcggcaa ctgttccggc      540
```

```
atcaccgtct cctccaccta ctgcagcacc aaccacgact acaccatctg gatgcctgag    600
aacctgaggc tgggcaccag ctgcgacatc ttcaccaata gcaggggcaa gagggcctcc    660
aagggaggaa agacctgcgg atttgtggat gagaggggcc tctacaagtc actgaagggc    720
gcctgcaagc tgaaactctg cggcgtgctg ggactgaggc tcatggacgg aacctgggtc    780
gctatgcaaa catccgacga gaccaagtgg tgtcccccg gccagctcgt gaatcttcat     840
gacttcagga gcgacgaaat cgagcacctc gtggtggagg aactggtcaa gagagggag    900 gagtgcctcg acgctctcga gtccatcatg accaccaaga gcgtgtcatt tagaagactg    960
agccacctga ggaagctggt ccccggcttc ggcaaagcct acaccatctt caacaagacc    1020
ctgatggagg ccgatgctca ctacaagagc gtcaggacct ggaacgagat catccccagc    1080
aaaggctgcc tgagagtggg aggaaggtgt caccccacg tgaacggcgt cttcttcaac    1140
ggcatcattc tcggaagcga cggacacgtc ctgattcccg agatgcagag ctcactcctg    1200
cagcagcata tggagctcct ggaaagctcc gtcattcctc tgatgcatcc cctcgctgat    1260
ccctccacag tcttcaaaga tggcgacgag gtggaggact ttgtggaagt gcacctcccc    1320
gatgttcatg agcaagtctc cggagtggaa ctgggcctcc ccaactgggg caagtacgtc    1380
ctcatgattg ctggcgctct catcgccctg atgctgatca tcttcctgat gacctgctgc    1440
agaagggtca atagacccga gagcactcag tccagcctcg gcgagaccgg cagaaatgtg    1500
agcgtgacct cccaatccgg caaagtcatc agctcctggg agagctacaa atccggagga    1560
gaaacaaggc tg                                                        1572
```

<210> SEQ ID NO 7
<211> LENGTH: 524
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Met Val Pro Gln Val Leu Leu Phe Val Pro Leu Leu Gly Phe Ser Leu
1               5                   10                  15

Cys Phe Gly Lys Phe Pro Ile Tyr Thr Ile Pro Asp Lys Leu Gly Pro
                20                  25                  30

Trp Ser Pro Ile Asp Ile His His Leu Ser Cys Pro Asn Asn Leu Val
            35                  40                  45

Val Glu Asp Glu Gly Cys Thr Asn Leu Ser Glu Phe Ser Tyr Met Glu
        50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
                100                 105                 110

Cys Arg Ala Ala Tyr Asn Trp Lys Met Ala Gly Asp Pro Arg Tyr Glu
            115                 120                 125

Glu Ser Leu His Asn Pro Tyr Pro Asp Tyr His Trp Leu Arg Thr Val
        130                 135                 140

Lys Thr Thr Lys Glu Ser Leu Val Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175
```

Asn Cys Ser Gly Ile Thr Val Ser Ser Thr Tyr Cys Ser Thr Asn His
            180                 185                 190

Asp Tyr Thr Ile Trp Met Pro Glu Asn Leu Arg Leu Gly Thr Ser Cys
            195                 200                 205

Asp Ile Phe Thr Asn Ser Arg Gly Lys Arg Ala Ser Lys Gly Gly Lys
            210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
            260                 265                 270

Pro Gly Gln Leu Val Asn Leu His Asp Phe Arg Ser Asp Glu Ile Glu
            275                 280                 285

His Leu Val Val Glu Glu Leu Val Lys Lys Arg Glu Glu Cys Leu Asp
            290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Arg Val Gly Gly
            355                 360                 365

Arg Cys His Pro His Val Asn Gly Val Phe Phe Asn Gly Ile Ile Leu
            370                 375                 380

Gly Ser Asp Gly His Val Leu Ile Pro Glu Met Gln Ser Ser Leu Leu
385                 390                 395                 400

Gln Gln His Met Glu Leu Leu Glu Ser Ser Val Ile Pro Leu Met His
                405                 410                 415

Pro Leu Ala Asp Pro Ser Thr Val Phe Lys Asp Gly Asp Glu Val Glu
            420                 425                 430

Asp Phe Val Glu Val His Leu Pro Asp Val His Glu Gln Val Ser Gly
            435                 440                 445

Val Glu Leu Gly Leu Pro Asn Trp Gly Lys Tyr Val Leu Met Ile Ala
450                 455                 460

Gly Ala Leu Ile Ala Leu Met Leu Ile Ile Phe Leu Met Thr Cys Cys
465                 470                 475                 480

Arg Arg Val Asn Arg Pro Glu Ser Thr Gln Ser Ser Leu Gly Glu Thr
                485                 490                 495

Gly Arg Asn Val Ser Val Thr Ser Gln Ser Gly Lys Val Ile Ser Ser
            500                 505                 510

Trp Glu Ser Tyr Lys Ser Gly Gly Glu Thr Arg Leu
            515                 520

<210> SEQ ID NO 8
<211> LENGTH: 1572
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atggtgcccc aggtgctgct ctttgtgccc ctgctgggct tcagcctctg cttcggcaag     60

```
ttccccatct acaccatccc agacaagctg gggccttgga gccccatcga catccaccac    120
ctgagctgcc ccaacaacct ggtggtggaa atgaaggct gcaccaacct gagcgagttc    180
tcctacatgg agctgaaggt gggctacatc tctgccatca aggtgaatgg cttcacctgc    240
actggagtgg tcacagaggc cgagacctac accaactttg tgggctatgt gaccaccacc    300
ttcaagagga agcacttccg gcccaccccca gatgcctgcc gggccgccta caactggaag    360
atggctgggg accccccgcta tgaggagagc ctcacaaccc ctacccaga ctaccactgg    420 ctgaggacag tgaagaccac caaggagagc ctggtgatca tcagccccag cgtgacagac    480
ctggacccct atgacaagag cctgcacagc cgggtgttcc ctggcggcaa ctgcagcggc    540
atcaccgtga gcagcaccta ctgcagcacc aaccacgact acaccatctg gatgccagaa    600
aacctgcggc tgggcaccag ctgtgacatc ttcaccaaca gccggggcaa gagggccagc    660
aagggcggca agacctgtgg ctttgtggat gagcggggcc tctacaagag cctgaagggg    720
gcctgcaagc tgaagctctg tggggtgctg ggcctgcggc tgatggatgg cacctgggtg    780
gccatgcaga cctcagatga gaccaagtgg tgcccccag gccagctggt gaacctgcat    840
gacttccgca gcgacgagat tgagcacctg gtggtggagg agctggtgaa gaagagggag    900
gagtgcctgg atgccctcga gagcatcatg accaccaaga gcgtgtcctt ccgccgcctg    960
agccacctgc ggaagctggt gcctggcttt ggaaaggcct acaccatctt caacaagacc   1020
ctgatggagg cagatgccca ctacaagagt gtgcggacct ggaatgagat catccccagc   1080
aagggctgcc tgcgggtggg cggccggtgc caccccacg tgaatggagt gttcttcaat   1140
ggcatcatcc tgggcagcga cggccacgtg ctgatccctg agatgcagag cagcctgctg   1200
cagcagcaca tggagctgct ggagagctct gtcatccccc tgatgcaccc cctcgctgac   1260
cccagcaccg tgttcaagga tggagatgaa gtggaggact cgtggaggt gcacctgcca   1320 gatgtgcacg agcaggtgtc tggcgtggag ctgggcctgc ccaactgggg caagtacgtg   1380
ctgatgattg ctggcgccct gatcgccctg atgctgatca tcttcctgat gacctgctgc   1440
cggcgggtga acagacctga gagcacccag agcagcctgg agagactgg aagaaatgtg   1500 tctgtcacca gccagagcgg caaggtgatc agcagctggg agagctacaa gagtggcggc   1560
gagaccaggc tg                                                       1572
```

<210> SEQ ID NO 9
<211> LENGTH: 524
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Val Pro Gln Val Leu Leu Phe Val Pro Leu Leu Gly Phe Ser Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Glu Phe Ser Tyr Met Glu
    50                  55                  60

Leu Lys Val Gly Tyr Ile Ser Ala Ile Lys Val Asn Gly Phe Thr Cys
65                  70                  75                  80
```

```
Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Asn Cys Ser Gly Ile Thr Val Ser Ser Thr Tyr Cys Ser Thr Asn His
            180                 185                 190

Asp Tyr Thr Ile Trp Met Pro Glu Asn Leu Arg Leu Gly Thr Ser Cys
        195                 200                 205

Asp Ile Phe Thr Asn Ser Arg Gly Lys Arg Ala Ser Lys Gly Gly Lys
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
            260                 265                 270

Pro Gly Gln Leu Val Asn Leu His Asp Phe Arg Ser Asp Glu Ile Glu
        275                 280                 285

His Leu Val Val Glu Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Ser Asp Gly His Val Leu Ile Pro Glu Met Gln Ser Ser Leu Leu
385                 390                 395                 400

Gln Gln His Met Glu Leu Leu Glu Ser Ser Val Ile Pro Leu Met His
                405                 410                 415

Pro Leu Ala Asp Pro Ser Thr Val Phe Lys Asp Gly Asp Glu Val Glu
            420                 425                 430

Asp Phe Val Glu Val His Leu Pro Asp Val His Glu Gln Val Ser Gly
        435                 440                 445

Val Glu Leu Gly Leu Pro Asn Trp Gly Lys Tyr Val Leu Met Ile Ala
    450                 455                 460

Gly Ala Leu Ile Ala Leu Met Leu Ile Ile Phe Leu Met Thr Cys Cys
465                 470                 475                 480

Arg Arg Val Asn Arg Pro Glu Ser Thr Gln Ser Ser Leu Gly Glu Thr
                485                 490                 495

Gly Arg Asn Val Ser Val Thr Ser Gln Ser Gly Lys Val Ile Ser Ser
```

```
                500              505              510
Trp Glu Ser Tyr Lys Ser Gly Gly Glu Thr Arg Leu
        515              520

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: This sequence may encompass 2-6 residues

<400> SEQUENCE: 10

His His His His His His
1               5
```